(12) United States Patent
Shelton, IV et al.

(10) Patent No.: US 10,898,219 B2
(45) Date of Patent: Jan. 26, 2021

(54) ELECTRICALLY-POWERED SURGICAL SYSTEMS FOR CUTTING AND WELDING SOLID ORGANS

(71) Applicant: Ethicon LLC

(72) Inventors: Frederick E. Shelton, IV, Hillsboro, OH (US); Cortney E. Henderson, Loveland, OH (US); Jason L. Harris, Lebanon, OH (US); David C. Yates, West Chester, OH (US); Jeffrey D. Messerly, Cincinnati, OH (US); Cara Shapiro, Milford, OH (US); Kevin D. Felder, Cincinnati, OH (US); Joshua Dean Young, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 397 days.

(21) Appl. No.: 15/689,694

(22) Filed: Aug. 29, 2017

(65) Prior Publication Data
US 2019/0059931 A1 Feb. 28, 2019

(51) Int. Cl.
*A61B 18/12* (2006.01)
*A61B 17/32* (2006.01)
(Continued)

(52) U.S. Cl.
CPC .. *A61B 17/320092* (2013.01); *A61B 18/1445* (2013.01); *A61B 34/30* (2016.02); *A61B 34/37* (2016.02); *A61B 2017/00017* (2013.01); *A61B 2017/00022* (2013.01); *A61B 2017/00309* (2013.01); *A61B 2017/00398* (2013.01); *A61B 2017/00402* (2013.01); *A61B 2017/00778* (2013.01); *A61B 2017/22015* (2013.01); *A61B 2017/22018* (2013.01); *A61B 2017/320074* (2017.08); *A61B 2017/320095* (2017.08); *A61B 2018/0063* (2013.01); *A61B 2018/00404* (2013.01); *A61B 2018/00589* (2013.01); *A61B 2018/00595* (2013.01); *A61B 2018/00607* (2013.01); *A61B 2018/00988* (2013.01);
(Continued)

(58) Field of Classification Search
CPC ........ A61B 17/320092; A61B 18/1445; A61B 2017/00022; A61B 2017/00309; A61B 2017/00402; A61B 2017/00778; A61B 2018/00595; A61B 2018/00607; A61B 2018/0063; A61B 2018/00988
See application file for complete search history.

(56) References Cited

U.S. PATENT DOCUMENTS 5,322,055 A 6/1994 Davison et al.
5,558,671 A 9/1996 Yates
(Continued)

FOREIGN PATENT DOCUMENTS

WO WO-2014151621 A1 9/2014
WO WO-2014151952 A1 9/2014

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — Daniel W Fowler
(74) *Attorney, Agent, or Firm* — Mintz Levin Cohn Ferris Glovsky and Popeo, P.C.

(57) ABSTRACT

Surgical systems and methods are provided for controlling actuation and movement of various surgical devices.

20 Claims, 30 Drawing Sheets

(51) Int. Cl.
*A61B 34/30* (2016.01)
*A61B 18/14* (2006.01)
*A61B 34/37* (2016.01)
*A61B 18/00* (2006.01)
*A61B 17/00* (2006.01)
*A61B 17/22* (2006.01)
*A61B 90/00* (2016.01)

(52) U.S. Cl.
CPC ... *A61B 2090/061* (2016.02); *A61B 2090/065* (2016.02); *A61B 2090/066* (2016.02); *A61B 2090/067* (2016.02)

(56) References Cited

U.S. PATENT DOCUMENTS

| | | |
|---|---|---|
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,063,098 A | 5/2000 | Houser et al. |
| 6,066,137 A | 5/2000 | Greep |
| 6,132,368 A | 10/2000 | Cooper |
| 6,168,605 B1 | 1/2001 | Measamer et al. |
| 6,231,565 B1 | 5/2001 | Tovey et al. |
| 6,325,811 B1 | 12/2001 | Messerly |
| 6,352,532 B1 | 3/2002 | Kramer et al. |
| 6,364,888 B1 | 4/2002 | Niemeyer et al. |
| 6,500,176 B1 | 12/2002 | Truckai et al. |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 | 6/2013 | Holcomb et al. |
| 8,602,286 B2 | 12/2013 | Crainich et al. |
| 8,684,253 B2 | 4/2014 | Giordano et al. |
| 8,771,270 B2 | 7/2014 | Burbank |
| 8,986,302 B2 | 3/2015 | Aldridge et al. |
| 9,023,071 B2 | 5/2015 | Miller et al. |
| 9,072,536 B2 | 7/2015 | Shelton, IV et al. |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,393,037 B2 | 7/2016 | Olson et al. |
| 9,445,816 B2 | 9/2016 | Swayze et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 2003/0129382 A1* | 7/2003 | Treat ............... A61B 18/085 428/316.6 |
| 2005/0256522 A1* | 11/2005 | Francischelli ...... A61B 18/1442 606/41 |
| 2006/0079874 A1 | 4/2006 | Faller et al. |
| 2006/0224158 A1* | 10/2006 | Odom ................ A61B 18/1445 606/51 |
| 2007/0191713 A1 | 8/2007 | Eichmann et al. |
| 2007/0276255 A1 | 11/2007 | Leban |
| 2007/0282332 A1* | 12/2007 | Witt ..................... B25B 23/142 606/50 |
| 2007/0282333 A1 | 12/2007 | Fortson et al. |
| 2008/0039836 A1 | 2/2008 | Odom et al. |
| 2008/0200940 A1 | 8/2008 | Eichmann et al. |
| 2010/0049187 A1* | 2/2010 | Carlton ............... A61B 5/0059 606/34 |
| 2010/0191282 A1 | 7/2010 | Harris et al. |
| 2010/0198248 A1 | 8/2010 | Vakharia |
| 2010/0228250 A1 | 9/2010 | Brogna |
| 2010/0286691 A1* | 11/2010 | Kerr ................... A61B 18/1206 606/51 |
| 2011/0015627 A1 | 1/2011 | DiNardo et al. |
| 2011/0015631 A1 | 1/2011 | Wiener et al. |
| 2011/0015632 A1 | 1/2011 | Artale |
| 2011/0087218 A1 | 4/2011 | Boudreaux et al. |
| 2011/0087256 A1 | 4/2011 | Wiener et al. |
| 2011/0196401 A1 | 8/2011 | Robertson et al. |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1* | 5/2012 | Yates ................ A61B 17/00234 606/33 |
| 2012/0292367 A1 | 11/2012 | Morgan et al. |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0261648 A1 | 10/2013 | Laurent et al. |
| 2013/0325034 A1 | 12/2013 | Schena et al. |
| 2014/0005701 A1 | 1/2014 | Olson et al. |
| 2014/0005718 A1 | 1/2014 | Shelton, IV et al. |
| 2014/0114334 A1 | 4/2014 | Olson et al. |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0263541 A1 | 9/2014 | Leimbach et al. |
| 2014/0276931 A1 | 9/2014 | Parihar et al. |
| 2015/0209059 A1 | 7/2015 | Trees et al. |
| 2015/0209573 A1 | 7/2015 | Hibner et al. |
| 2015/0272575 A1 | 10/2015 | Leimbach et al. |
| 2015/0282825 A1 | 10/2015 | Trees et al. |
| 2015/0327854 A1 | 11/2015 | Whitman et al. |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089198 A1 | 3/2016 | Arya et al. |
| 2016/0089533 A1 | 3/2016 | Turner et al. |
| 2016/0175060 A1 | 6/2016 | Park |
| 2016/0287252 A1 | 10/2016 | Parihar |
| 2016/0367243 A1 | 12/2016 | Martin et al. |
| 2017/0056038 A1 | 3/2017 | Hess et al. |
| 2017/0196637 A1 | 7/2017 | Shelton, IV et al. |
| 2017/0202609 A1 | 7/2017 | Shelton, IV et al. |
| 2018/0250004 A1 | 9/2018 | Williams et al. |
| 2019/0059930 A1 | 2/2019 | Stulen et al. |
| 2019/0059932 A1 | 2/2019 | Isosaki et al. |
| 2019/0060018 A1 | 2/2019 | Shelton, IV et al. |

OTHER PUBLICATIONS

U.S. Appl. No. 15/237,653 entitled "Methods, Systems, and Devices for Controlling a Motor of a Robotic Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

U.S. Appl. No. 15/674,075 entitled "Clip Retention for Surgical Clip Applier" filed Aug. 10, 2017.

(56) References Cited

OTHER PUBLICATIONS

U.S. Appl. No. 15/674,086 entitled "Surgical Clip Applier Jaw Alignment" filed Aug. 10, 2017.
U.S. Appl. No. 15/674,096 entitled "Surgical Device with Overload Mechanism" filed Aug. 10, 2017.
U.S. Appl. No. 15/674,121 entitled "Jaw for Clip Applier" filed Aug. 10, 2017.
U.S. Appl. No. 15/674,125 entitled "Clip Appliers with Extended Jaw Tip" filed Aug. 10, 2017.
U.S. Appl. No. 15/674,166 entitled "Surgical Clip Applier" filed Aug. 10, 2017.
U.S. Appl. No. 15/689,072 entitled "Methods, Systems, and Devices for Controlling Electrosurgical Tools" filed Aug. 29, 2017.
U.S. Appl. No. 29/613,511 entitled "Clip Applier Rotation Knob" filed Aug. 10, 2017.
International Preliminary Report on Patentability for Application No. PCT/IB2018/056363, dated Mar. 12, 2020, 14 pages.
International Search Report and Written Opinion issued in International Application No. PCT/IB2018/056363, dated Jan. 9, 2019, 20 pages.

* cited by examiner

US 10,898,219 B2

ELECTRICALLY-POWERED SURGICAL SYSTEMS FOR CUTTING AND WELDING SOLID ORGANS

FIELD

Electrically-powered surgical systems and methods for using the same are provided for cutting or dissecting tissue.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation and actuation of an end effector, and one or more generators for delivery of energy.

A common concern with electrically-powered surgical devices is a relative lack of c haptic feedback. Mechanically-powered surgical devices can have articulating features (e.g., jaws, blades, etc.) powered by user actuation of actuatable objects such as triggers, knobs, etc. These mechanically-powered surgical devices can inherently provide a high degree haptic feedback because device actuation is completely reliant upon the movements of the user and mechanical linkages between articulating features and actuatable objects can provide force-feedback. However, this direct connection between user movements and surgical device actuation is not present in electrically-powered devices, where articulating features can be moved by electrically-powered motors in response to actuation of low-feedback actuatable objects, such as buttons. Thus, reliance upon haptic feedback to assess the state of surgical functions (e.g., progress of cutting operations, clamping forces applied to tissue, etc.) can be significantly impaired in electrically-powered surgical devices as compared to mechanically-powered surgical devices.

Accordingly, there remains a need for improved devices and methods that address current issues with electrically-powered surgical devices.

SUMMARY

Surgical systems and methods for using the same are provided herein.

In one exemplary embodiment, a surgical system is provided and can include a surgical tool and a control system. The surgical tool can include a shaft and an end effector formed at a distal end thereof. The end effector can have a clamping element and an ultrasonic blade and it can be configured to clamp and treat tissue disposed between the clamping element and the ultrasonic blade. The control system can be configured to variably control a clamping force applied to tissue disposed between the clamping element and the ultrasonic blade according to one or more control modes before transmission of ultrasonic vibrations to the ultrasonic blade to coagulate and/or cut the tissue. The clamping force can range between a maximum clamping force ($F_{max}$) and a minimum clamping force ($F_{min}$).

Embodiments of the control system can have a variety of configurations. In one aspect, the control system can be configured to apply the clamping force to tissue over a first predetermined clamping time ($t_{c1}$) in a first control mode. The first control mode can occur before transmission of ultrasonic vibrations to the ultrasonic blade and it can include gradually increasing the clamping force from $F_{min}$ to $F_{max}$. In another aspect, the control system can be configured to maintain application of $F_{max}$ to tissue for a second predetermined clamping time ($t_{c2}$) in a second control mode. The second control mode can occur immediately after the first control mode and prior to transmission of ultrasonic vibrations to the ultrasonic blade. In another aspect, the control system can be configured to concurrently apply the clamping force to tissue and ultrasonic vibrations to the blade for a predetermined treatment time ($t_t$) in a third control mode. The third control mode can occur immediately after the second control mode and it can include applying a treatment clamping force ($F_{treat}$) between $F_{min}$ and $F_{max}$. In another aspect, the control system can be configured to vary a peak amplitude of ultrasonic waves transmitted to the ultrasonic blade between a maximum amplitude ($A_{max}$) and a minimum amplitude ($A_{min}$) during the third control mode. In another aspect, an amplitude ($A_1$) between $A_{max}$ and $A_{min}$ can be transmitted for a first portion of the predetermined treatment time $t_{t1}$ and $A_{min}$ can be transmitted immediately thereafter for a second portion of the predetermined treatment time $t_{t2}$. In another aspect, the amplitude can be increased from the $A_1$ to $A_{max}$ immediately following $t_{t2}$.

In another exemplary embodiment, a surgical system is provided and can include a surgical tool and a control system. The surgical tool can include a shaft and an end effector formed at a distal end thereof. The end effector can have a clamping element and an ultrasonic blade and it can be configured to clamp and treat tissue disposed between the clamping element and the ultrasonic blade. The control system can be configured to variably control a clamping force applied to tissue disposed between the clamping element and the ultrasonic blade according to one or more control modes during transmission of ultrasonic vibrations to the ultrasonic blade to coagulate and/or cut the tissue. The clamping force can range between a maximum clamping force ($F'_{max}$) and a minimum clamping force ($F'_{min}$).

Embodiments of the control system can have a variety of configurations. In one aspect, the control system can be configured to apply the clamping force to tissue for a first predetermined clamping time ($t'_{c1}$) in a first control mode. The first control mode can occur before transmission of ultrasonic vibrations to the ultrasonic blade and it can include gradually increasing the clamping force from $F'_{min}$ to a treatment clamping force $F'_{treat}$ between $F'_{min}$ and $F'_{max}$. In another embodiment, the control system can be configured to maintain application of $F'_{treat}$ to tissue for a second predetermined clamping time ($t'_{c2}$) in a second control mode. The second control mode can occur immediately after the first control mode and before transmission of ultrasonic vibrations to the ultrasonic blade. In another aspect, the control system can be configured to apply both the clamping force to tissue and the ultrasonic vibrations to the ultrasonic blade for a predetermined treatment time ($t'_t$) immediately following the second control mode. In another aspect, the control system can be configured to apply $F_{max}$ to tissue for a first portion ($t'_{t1}$) of the predetermined treatment time $t'_t$ in a third control mode. In another aspect, an amplitude ($A'_1$) between a minimum amplitude $A'_{max}$ and a maximum amplitude $A'_{min}$ is transmitted to the blade during the third control mode. In another aspect, the control system can be configured to apply $F'_{treat}$ to tissue in a fourth control mode immediately after third control mode. In another aspect, an amplitude ($A'_2$) greater than $A'_1$ and less than $A'_{max}$ can be transmitted to the ultrasonic blade for a second predetermined treatment time ($t'_{t2}$) immediately after $t'_{t1}$. In another aspect, $A'_{min}$ can be transmitted to the ultrasonic blade for a third predetermined treatment time ($t'_{t3}$) immediately after $t'_{t2}$. In another aspect, $A'_{max}$ can be transmitted to the blade for a fourth predetermined treatment time ($t'_{t4}$) immediately after $t'_{t3}$.

Methods for treating tissue are also provided. In one embodiment, the method can include actuating a motor to cause an end effector of a surgical instrument including a clamping element and an ultrasonic blade to apply a clamping force to tissue disposed between the clamping element and the ultrasonic blade. The method can also include transmitting, by an ultrasonic generator, ultrasonic vibrations to the ultrasonic blade to coagulate or cut the tissue clamped between the clamping element and the ultrasonic blade. The method can also include varying, by the motor, the clamping force applied to tissue disposed between the clamping element and the ultrasonic blade before or during transmission of ultrasonic vibrations to the blade according to one or more control modes, the clamping force ranging between a maximum clamping force ($F_{max}$) and a minimum clamping force ($F_{min}$).

In another embodiment, $F_{max}$ can be applied to the tissue for a predetermined clamping time prior to transmitting ultrasonic vibrations to the blade.

In another embodiment, a treatment clamping force ($F_{treat}$) between $F_{max}$ and $F_{min}$ can be applied to the tissue for a predetermined treatment time during transmission of ultrasonic vibrations to the blade.

In another embodiment, a treatment clamping force ($F'_{treat}$) between $F_{max}$ and $F_{min}$ can be applied to the tissue for a predetermined clamping time before transmission of ultrasonic vibrations to the blade. $F_{max}$ can be applied to the tissue for a first predetermined treatment time during transmission of ultrasonic vibrations to the blade. $F_{treat}$ can be applied to the tissue for a second predetermined treatment time during transmission of ultrasonic vibrations to the blade and after the first predetermined treatment time.

In another exemplary embodiment, a surgical system is provided and can include an end effector, a shaft assembly, an interface assembly, and a control system. The end effector can have an ultrasonic blade and a clamping element, where the ultrasonic blade can be configured to receive ultrasonic vibrations from an ultrasonic transducer and the clamping element can be configured to clamp and treat tissue disposed between the clamping element and the ultrasonic blade as ultrasonic vibrations are applied to the tissue from the ultrasonic blade. The shaft assembly can have a longitudinal axis and the end effector can be disposed at a distal end thereof. The shaft assembly can also include an articulation section operable to deflect the end effector away at the longitudinal axis an articulation angle between a minimum articulation angle of about 0 degrees when the end effector is aligned with the longitudinal axis of the shaft assembly to a maximum non-zero articulation angle in either direction when the end effector is not aligned with the longitudinal axis of the shaft assembly. The interface assembly can have one or more drive shafts coupled to the end effector and the shaft assembly configured to drive movement of the end effector and the shaft assembly. The control system can be configured to control an amplitude of ultrasonic vibrations received by the ultrasonic blade such that the amplitude increases with an increase in the articulation angle of the end effector.

Embodiments of the control system can have a variety of configurations. In one aspect, the control system can be configured to measure rotation of a first drive shaft that is operable to adjust the articulation angle of the end effector. In another aspect, the control system can be configured to control the amplitude of the ultrasonic vibrations based upon the measured rotation of the first drive shaft. In another aspect, the control system can be configured to control the amplitude of the ultrasonic vibrations during articulation of the end effector.

In another embodiment, the control system can be configured to control a rate of change of the amplitude of the ultrasonic vibrations with respect to the articulation of the end effector between the minimum and maximum articulation angles. The rate of change of the amplitude can be approximately constant between the minimum and maximum articulation angles. Alternatively, the rate of change of the amplitude can vary between the minimum and maximum articulation angles.

Methods for treating tissue are also provided. In one embodiment, the method can include actuating a motor to cause a shaft assembly having a longitudinal axis and an end effector disposed at a distal end thereof having a clamping element and an ultrasonic blade, to deflect at an articulation angle between a minimum articulation angle of about 0 degrees when the end effector is aligned with the longitudinal axis of the shaft assembly and a maximum non-zero articulation angle in either direction when the end effector is not aligned with the longitudinal axis of the shaft. The method can also include transmitting, by an ultrasonic generator, ultrasonic vibrations to the ultrasonic blade to coagulate or cut tissue clamped between the clamping element and the ultrasonic blade. The method can additionally include varying, by the ultrasonic generator, an amplitude of the ultrasonic vibrations such that the amplitude increases with an increase in the articulation of the end effector.

In another embodiment, the method can include measuring a rotation of a drive shaft coupled to the shaft assembly and configured to drive articulation of the end effector between the minimum and maximum articulation angles. The amplitude of the ultrasonic vibrations can be varied based upon the measured rotation of the drive shaft. The amplitude of the ultrasonic vibrations can be varied during articulation of the end effector.

In another embodiment, the method can include varying a rate of change of the amplitude of the ultrasonic vibrations with respect to the articulation of the end effector between the minimum and maximum articulation angles. The rate of change of the amplitude can be approximately constant between the minimum and maximum articulation angles. Alternatively, the rate of change of the amplitude can vary between the minimum and maximum articulation angles.

In another exemplary embodiment, a surgical system is provided and can include a surgical tool, a closure mechanism, and a control system. The surgical tool can include a shaft and an end effector formed at a distal end thereof. The end effector can have a clamping element and an ultrasonic blade. The clamping element can be movable relative to the ultrasonic blade to clamp and treat tissue disposed between the clamping element and the ultrasonic blade. The closure mechanism can be configured to selectively move the clamping element towards the ultrasonic blade from an open configuration to a closed configuration at a predetermined clamping velocity ($v_c$). The control system can be configured to maintain $v_c$ at a first clamping velocity ($v_{c1}$) greater than a minimum clamping velocity ($v_{min}$) until a predetermined clamping force threshold ($F_o$) is achieved. The control system can also be configured to determine a closure parameter including at least one of an amount of time required to reach $F_o$ and an amount of displacement of the clamping element required to achieve $F_o$. The control system can additionally be configured to determine a tissue characteristic based upon the closure parameter. The control system can also be configured to deliver energy to the ultrasonic blade to treat tissue in a feathering treatment according to a feathering treatment protocol based upon the determined tissue characteristic.

In another embodiment, $F_o$ can be a force resulting from contact of the clamping element with a tissue disposed between the clamping element and the ultrasonic blade.

In another embodiment, the feathering treatment can be effective to coagulate a tissue disposed between the clamp arm and the ultrasonic blade.

In another embodiment, the tissue characteristic can be a thickness of a tissue disposed between the clamping element and the ultrasonic blade.

In another embodiment, when the tissue thickness is less than a predetermined thickness, the control system can be configured to operate in the feathering treatment protocol by maintaining $v_c$ at a third clamping velocity ($v_{c3}$) while a clamping force applied to tissue disposed between the clamp arm and the ultrasonic blade is less than a predetermined second treatment force ($F_2$). The control system can also be configured to operate in the feathering treatment protocol by decreasing $v_c$ from $v_{c3}$ to a fourth clamping velocity ($v_{c4}$) for the remainder of the feathering treatment in response to the clamping force rising to $F_2$, where $v_{c4}$ can be configured to maintain the clamping force below $F_2$. $v_{c3}$ and $v_{c4}$ can each be approximately constant.

In another embodiment, when the tissue thickness is greater than a predetermined thickness, the control system can be configured to operate in the feathering treatment protocol by applying a clamping force to tissue disposed between the clamp arm and the ultrasonic blade at an approximately constant first treatment force ($F_1$). The control system can also be configured to allow $v_c$ to decrease to a level approximately equal to $v_{min}$ and increase the clamping force to a level between $F_1$ and a less than a second treatment force ($F_2$) for the remainder of the feathering treatment. $F_1$ can be based upon the determined tissue characteristic.

In another embodiment, the system can include an electrode configured to deliver radiofrequency energy to a tissue disposed between the clamping element and the ultrasonic blade. The control system can be configured to deliver at least one of ultrasonic energy to the ultrasonic blade and radiofrequency energy to the electrode according to a sealing treatment protocol occurring after the feathering treatment for coagulating and cutting a tissue disposed a tissue disposed between the clamping element and the ultrasonic blade.

In another embodiment, the control system can be configured to perform the sealing treatment in response to detection that a preselected trigger condition is satisfied. In one aspect, the trigger condition can be movement of the clamping element to a predetermined distance from the ultrasonic blade. In another aspect, the trigger condition can be deviation of $v_c$ from a velocity set point by a predetermined velocity threshold. In another aspect, the trigger condition can be application of a clamping force at a predefined amount of a maximum clamping force $F_{max}$.

Methods for treating tissue are also provided. In one embodiment, the method can include actuating a motor of a surgical tool including a shaft and an end effector. The end effector can be formed at a distal end of the shaft and it can have a clamping element and an ultrasonic blade coupled to an ultrasonic transducer. The clamping element can be moveable relative to the ultrasonic blade to a tissue clamping position between an open position and a closed position of the clamping element at a predetermined clamping velocity ($v_c$). The method can also include maintaining $v_c$ at a first clamping velocity ($v_{c1}$) greater than a minimum clamping velocity ($v_{min}$) until a predetermined clamping force threshold ($F_o$) is achieved. The method can also include determining a closure parameter including at least one of an amount of time ($t_c$) required to reach $F_o$ and an amount of displacement of the clamping element $\delta_c$ required to achieve $F_o$. The method can also include determining a tissue characteristic based upon the closure parameter. The method can also include delivering energy to the ultrasonic blade to treat tissue in a feathering treatment according to a feathering treatment protocol based upon the determined tissue characteristic.

In another embodiment, $F_o$ can be a force resulting from contact of the clamping element with a tissue disposed between the clamping element and the ultrasonic blade.

In another embodiment, the feathering treatment can be effective to cauterize a tissue disposed between the clamp arm and the ultrasonic blade.

In another embodiment, the tissue characteristic can be a thickness of a tissue disposed between the clamping element and the ultrasonic blade.

In another embodiment, the method can include determining the tissue thickness to be less than a predetermined thickness. The method can also include maintaining $v_c$ at a third clamping velocity ($v_{c3}$) while a clamping force applied to tissue disposed between the clamp arm and the ultrasonic blade is less than a predetermined second treatment force ($F_2$). The method can also include decreasing $v_c$ from $v_{c3}$ to a fourth clamping velocity ($v_{c4}$) for the remainder of the feathering treatment in response to the clamping force rising to $F_2$, wherein $v_{c4}$ is configured to maintain the clamping force below $F_2$. $v_{c3}$ and $v_{c4}$ can each be approximately constant.

In another embodiment, the method can include determining the tissue thickness to be greater than a predetermined thickness and applying a first treatment force $F_1$ to tissue disposed between the clamp arm and the ultrasonic blade. The method can also include allowing $v_c$ to decrease to a level approximately equal to $v_{min}$ and increasing the first treatment force to a level between $F_1$ and a second treatment force $F_2$ for the remainder of the feathering treatment. $F_1$ can be based upon the determined tissue characteristic.

In another embodiment, the method can include delivering radiofrequency energy to a tissue disposed between the clamping element and the ultrasonic blade during the feathering treatment. An amplitude of each of the ultrasonic and radiofrequency energies can be approximately constant during the feathering treatment. The method can also include delivering at least one of ultrasonic energy and radiofrequency energy to treat the tissue in a sealing treatment occurring after the feathering treatment according to a sealing treatment protocol, the sealing treatment configured to coagulate and cut the tissue.

In another embodiment, the method can include performing the sealing treatment in response to detection that a preselected trigger condition is satisfied. In one aspect, the trigger condition can be movement of the closure mechanism to a predetermined distance from the ultrasonic blade. In another aspect, the trigger condition can be deviation of $v_c$ from a velocity set point by a predetermined velocity threshold. In another aspect, the trigger condition can be application of a clamping force at a predefined amount of a maximum clamping force $F_{max}$.

In another exemplary embodiment, a surgical system is provided and can include a surgical tool, a closure mechanism, a motor, and a control system. The surgical tool can include a shaft and an end effector formed at a distal end thereof. The end effector can have a clamping element and an ultrasonic blade operably coupled to an ultrasonic transducer. The clamping element can be movable relative to the ultrasonic blade to clamp tissue disposed between the clamping element and the ultrasonic blade such that a first tissue treatment is effected upon energizing the ultrasonic blade. The closure mechanism can be configured to selectively displace the clamping element from an initial, open position to a tissue clamping position. The motor can be operably coupled to the closure mechanism. The control system can be in communication with the motor and it can be configured to dynamically control a predetermined tissue clamping force applied to a tissue disposed between the clamping element and the ultrasonic blade within a desired range between a minimum treatment force and a maximum treatment force during the first tissue treatment to respond to changes in the tissue as a result of the first tissue treatment.

In another embodiment, the control system can be configured to control a position of the clamping element in response to receipt of a commanded position when the clamping force applied to tissue is less than the minimum treatment force and the clamping element is distanced by greater than a predetermined minimum amount from the closed position.

In another embodiment, the control system can be configured to dynamically control the position of the clamping element to maintain the predetermined tissue clamping force when the clamping force applied to tissue exceeds the minimum treatment force or the clamping element is distanced by less than a predetermined minimum amount from the closed position. The control system can also be configured to control a motor torque within a predetermined range to maintain the tissue clamping force within the desired range during the first tissue treatment. The control system can also be configured to control an amount of current delivered to the motor to control the motor torque.

In another embodiment, the system can include an electrode coupled to the clamping element and operatively coupled to a radiofrequency generator. The electrode can be configured to provide a second tissue treatment to the tissue disposed between the clamping element and the ultrasonic blade when receiving radiofrequency energy from the radiofrequency generator.

In another embodiment, the control system can be configured to determine a position of the clamping element with respect to the closed position and allow delivery of radiofrequency energy less than a predetermined threshold energy to the electrode when the position of the clamping element is distanced by greater than a predetermined amount from the closed position.

In another embodiment, the control system can be configured to determine a position of the clamping element with respect to the closed position and allow delivery of radiofrequency energy greater than a predetermined threshold energy to the electrode when the position of the clamping element is distanced by less than a predetermined amount from the closed position.

In another embodiment, the control system can be configured to determine a position of the clamping element with respect to the closed position and inhibit delivery of radiofrequency energy greater than a predetermined threshold energy to the electrode when the clamping element is distanced by greater than a predetermined minimum distance from the closed position. The control system can also be configured to trigger an alert to position the clamping element at a distance less than the predetermined minimum distance to allow delivery of radiofrequency energy greater than the predetermined threshold energy to the electrode.

Methods for treating tissue are also provided. In one embodiment, the method can include actuating a motor of a surgical tool including a shaft and an end effector. The end effector can be formed at a distal end of the shaft and it can include a clamping element and an ultrasonic blade coupled to an ultrasonic transducer. The clamping element can be moveable relative to the ultrasonic blade to a tissue clamping position between an open position and a closed position of the clamping element in response to the motor actuation. The method can also include adjusting the position of the clamping element using the motor to a first tissue clamping position where the clamping element applies a clamping force approximately equal to a predetermined minimum treatment clamping force. The method can also include transmitting ultrasonic energy from the ultrasonic transducer to the ultrasonic blade after the applied clamping force is greater than or equal to the minimum treatment clamping force. The method can also include adjusting the position of the clamping element using the motor to apply a target clamping force between the minimum treatment clamping force and a predetermined maximum treatment clamping force while ultrasonic energy is transmitted to the ultrasonic blade.

In another embodiment, the method can include controlling a position of the clamping element in response to receipt of a commanded position when the clamping force applied to tissue is less than the minimum treatment force and the position of the clamping element is distanced by greater than a predetermined minimum amount from the closed position.

In another embodiment, the method can include dynamically controlling the position of the clamping element to maintain the target clamping force when the clamping force exceeds the minimum treatment force or the clamping element is distanced by less than a predetermined minimum amount from the closed position. The method can also include controlling a motor torque within a predetermined range to maintain the tissue clamping force within the desired range during the first tissue treatment. The method can also include controlling an amount of current delivered to the motor to control the motor torque.

In another embodiment, the method can include delivering radiofrequency energy to an electrode coupled to the clamping element.

In another embodiment, the method can include determining a position of the clamping element with respect to the closed position and delivering radiofrequency energy less than a predetermined threshold energy to the electrode when the position of the clamping element is distanced by greater than a predetermined amount from the closed position.

In another embodiment, the method can include determining a position of the clamping element with respect to the closed position and delivering of radiofrequency energy greater than a predetermined threshold energy to the electrode when the position of the clamping element is distanced by less than a predetermined amount from the closed position.

In another embodiment, the method can include determining a position of the clamping element with respect to the closed position and inhibiting delivery of radiofrequency energy greater than a predetermined threshold energy to the electrode when the clamping element is distanced by greater than a predetermined minimum distance from the closed position. The method can also include triggering an alert to position the clamping element at a distance less than the predetermined minimum distance to allow delivery of radiofrequency energy greater than the predetermined threshold energy to the electrode.

BRIEF DESCRIPTION OF THE DRAWINGS

Embodiments of the disclosure can be more fully understood from the following detailed description taken in conjunction with the accompanying drawings, in which.

DETAILED DESCRIPTION

Figure 1:
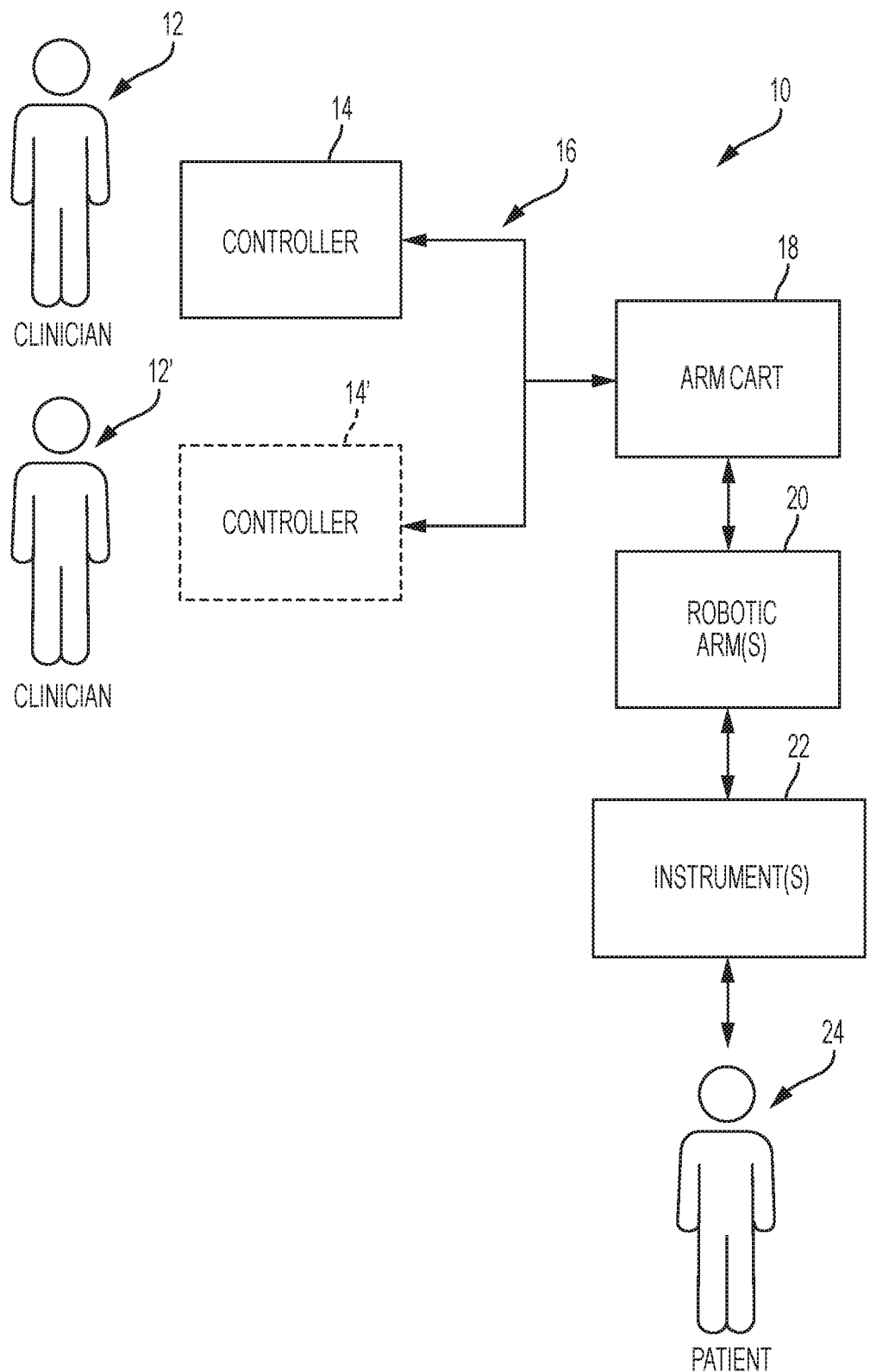
FIG. 1 is a block diagram illustrating one exemplary embodiment of a robotic surgical system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In general, embodiments of surgical systems are provided and can include at least an electromechanical tool having an end effector and a control system. The end effector can be designed for cutting tissue, e.g., a single cutting blade or a pair of cutting blades, or for dissecting tissue. Depending on the design of the end effector, the surgical system can include one or more motors that actuate the electromechanical tool and/or one or more generators (e.g., ultrasound, radiofrequency, etc.) can be configured to deliver energy to tissue for treatment.

Embodiments of the control system can be configured to perform protocols that facilitate tissue treatments (e.g., clamping, cutting, cauterizing, etc.) by implementing limits and triggers on monitored parameters of an end effector engaging tissue. Examples of monitored parameters can include, but are not limited to, clamping forces applied to tissue, clamping velocity, clamping displacement, and energy supplied to end effectors for tissue treatment. As discussed in greater detail below, these control protocols can compensate for reduced haptic feedback and ensure that tissue treatments are performed properly.

Exemplary Robotic Surgical System Overview

FIG. 1 illustrates one exemplary embodiment of a robotic surgical system 10. As shown, system 10 comprises at least one controller 14 and at least one arm cart 18. The arm cart 18 can be mechanically and/or electrically coupled to one or more robotic manipulators or arms 20. Each robotic arm 20 comprises one or more surgical instruments 22 for performing various surgical tasks on a patient 24. Operation of arm cart 18, including arms 20 and surgical instruments 22, can be directed by a user 12 (e.g., a clinician) from controller 14.

Optionally, embodiments of the system 10 can also include a second controller 14' that is configured for operation by a second user 12'. The second controller 14' can direct operation of the arm cart 18 in conjunction with the first user 12'. For example, each of the users 12, 12' can control different arms 20 of the arm cart 18 or, in some cases, complete control of arm cart 18 can be passed between the users 12, 12'. In certain embodiments, additional arm carts (not shown) can be utilized on the patient 24. These additional arm carts can be controlled by one or more of the controllers (14, 14').

Arm carts 18 and controllers 14, 14" can be in communication with one another via a communications link 16, which can be any suitable type of wired and/or wireless communications link carrying any suitable type of signal (e.g., electrical, optical, infrared, etc.) according to any suitable communications protocol. Communications link 16 can be an actual physical link or it can be a logical link that uses one or more actual physical links. When the link is a logical link the type of physical link can be a data link, uplink, downlink, fiber optic link, point-to-point link, for example.

Figure 2:
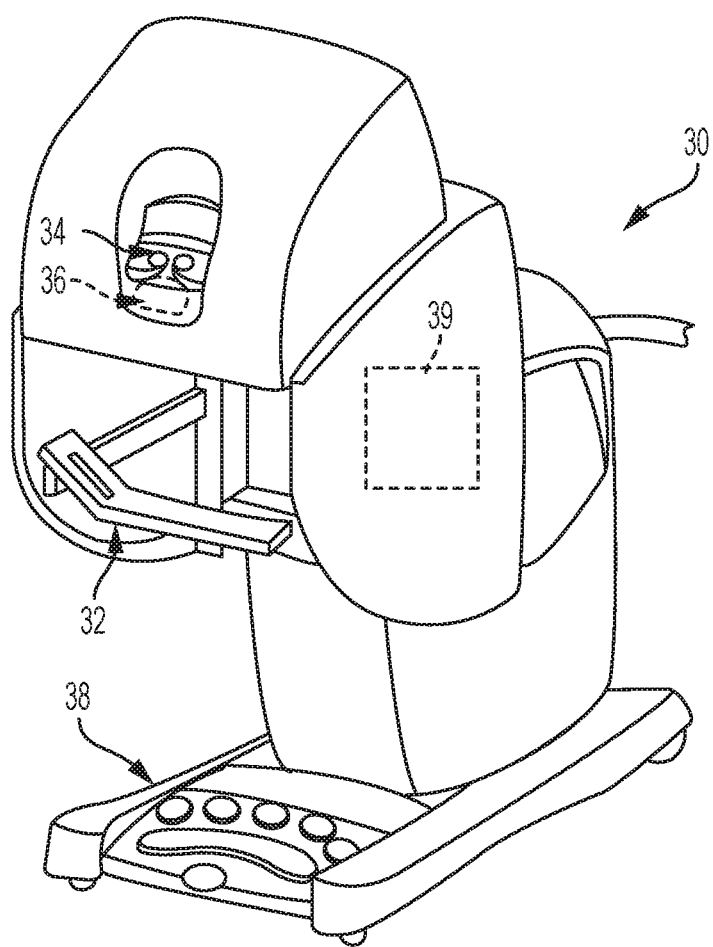
FIG. 2 is a perspective view illustrating an exemplary embodiment of a controller of the robotic surgical system of FIG. 1.

FIG. 2 is a perspective view illustrating one exemplary embodiment of a controller 30 that can serve as a controller 14 of system 10. In this example, controller 30 generally includes a user input assembly 32 having precision user input features (not shown) that can be grasped by the user and manipulated in space while the user views the surgical procedure via a display 34 (e.g., a stereo display). The display 34 can show views from one or more endoscopes viewing the surgical site within the patient and/or any other suitable view(s). In addition, a feedback meter 36 can be viewed through the display 34 and provide the user with a visual indication of the amount of force being applied to a component of the surgical instrument 22 (e.g., a cutting member or clamping member, etc.).

The user input features of user input assembly 32 can also include manual input devices that move with multiple degrees of freedom for intuitively actuating tools (e.g., for closing grasping saws, applying an electrical potential to an electrode, etc.). As an example, manual input devices can include actuatable handles and/or foot switches. As shown in FIG. 2, the controller 30 can include one or more foot switches 38 that are configured to provide additional control of arms 20 and surgical instruments 22 to the user. Other sensor arrangements can be employed to provide controller 30 with one or more indications regarding operational conditions of the surgical instrument 22.

Embodiments of the controller 30 can also include a control system 39 configured to control movement and actuation of one or more of the instruments 22. For example, the control system 39 can include at least one computer system that can include components (e.g. one or more processors) that are configured for running one or more logic functions with respect to a program stored in a memory coupled to the processor. For example, the processor can be coupled to the user input assembly 32 and it can be configured for receiving sensed information, aggregating it, and computing outputs based at least in part on the sensed information. These outputs can be transmitted to motors of the instruments 22 to control the instruments 22 during use, as discussed in greater detail below.

Figure 3:
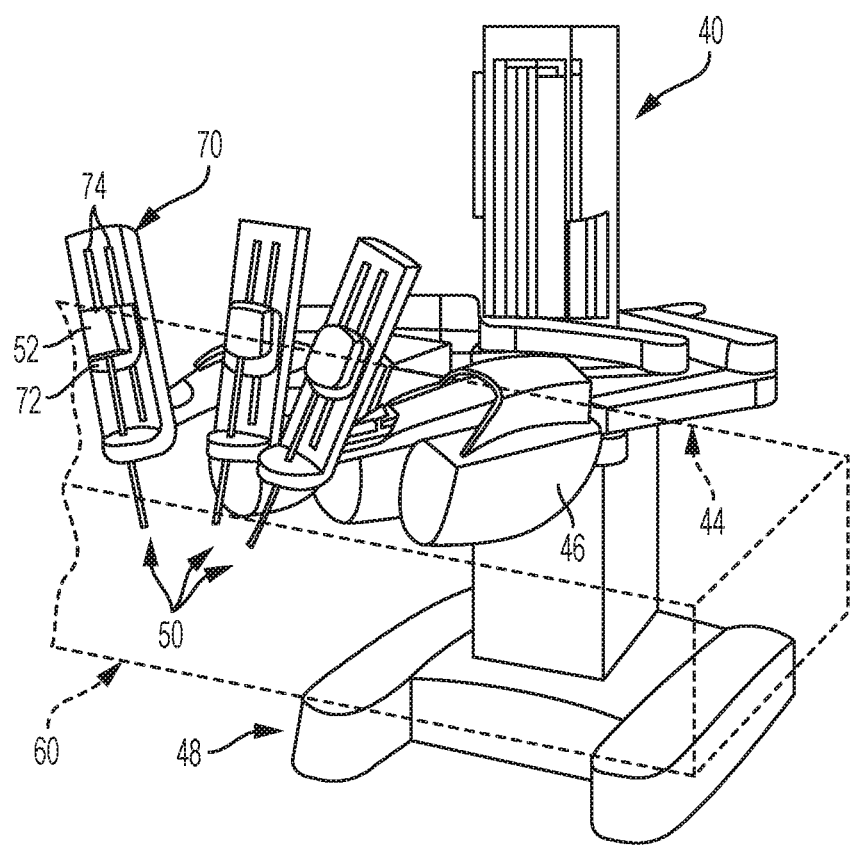
FIG. 3 depicts a perspective view illustrating an exemplary embodiment of a robotic arm cart of the robotic surgical system of FIG. 1.

FIG. 3 is a perspective view illustrating one exemplary embodiment of a robotic arm cart 40 that can serve as the arm cart 18 of the system 10. In this example, the arm cart 40 can be configured to actuate a plurality of surgical instruments 50. While three instruments 50 are shown in this example, it should be understood that arm cart 40 can be operable to support and actuate any suitable number of surgical instruments 50. Each of the surgical instruments 50 can be supported by a series of manually articulatable linkages, generally referred to as set-up joints 44, and a robotic manipulator 46. These structures are herein illustrated with protective covers extending over much of the robotic linkage. These protective covers can be optional, and they can be limited in size or entirely eliminated in some versions to minimize the inertia that can be encountered by the servo mechanisms used to manipulate such devices, to limit the volume of moving components so as to avoid collisions, and to limit the overall weight of arm cart 40.

Each robotic manipulator 46 terminate at an instrument platform 70, which can be pivotable, rotatable, and otherwise movable by the robotic manipulator 46. Each platform include an instrument dock 72 that is slidable along a pair of tracks 74 to further position instrument 50. Such sliding can be motorized in the present example. Each instrument dock 72 can also include mechanical and electrical interfaces that can be coupled with an interface assembly 52 of instrument 50. For example, the dock 72 can include four rotary outputs that couple with complementary rotary inputs of interface assembly 52. Such rotary drive features can drive various functionalities in instrument 50, as is described in various references cited herein and/or described in greater detail below. Electrical interfaces can establish communication via physical contact, inductive coupling, and/or otherwise; and can be operable to provide electrical power to one or more features in instrument 50, provide commands and/or data communication to instrument 50, and/or provide commands and/or data communication from instrument 50. Various suitable ways in which an instrument dock 72 can mechanically and electrically communicate with an interface assembly 52 of an instrument 50 will be apparent to those of ordinary skill in the art in view of the teachings herein. It should also be understood that instrument 50 can include one or more cables that couple with a separate power source and/or control unit, to provide communication of power and/or commands/data to/from instrument 50.

The arm cart 40 can also include a base 48 that can be movable (e.g., by a single attendant to selectively position the arm cart 40 in relation to a patient). The arm cart 40 can generally have dimensions suitable for transporting the arm cart 40 between operating rooms. The arm cart 40 can be configured to fit through standard operating room doors and onto standard hospital elevators. In some versions, an automated instrument reloading system (not shown can also be positioned in or near the work envelope 60 of arm cart 40, to selectively reload components (e.g., staple cartridges, etc.) of instruments 50.

In addition to the foregoing, it can be understood that one or more aspects of system 10 can be constructed in accordance with the teachings from one or more of U.S. Pat. Nos. 5,792,135; 5,817,084; 5,878,193; 6,231,565; 6,783,524; 6,364,888; 7,524,320; 7,691,098; 7,806,891; 7,824,401; and/or U.S. Pub. No. 2013/0012957. The disclosures of each of the foregoing U.S. patents and U.S. patent publication are incorporated by reference in their entirety. Still other suitable features and operabilities that can be incorporated into system 10 will be apparent to those of ordinary skill in the art in view of the teachings herein.

While aspects of the disclosure are explained herein in the context of a robotic surgical system, it is understood that the present disclosure is applicable to powered, non-robotic surgical systems as well.

II. Ultrasonic Surgical Instrument with Articulation Feature

Ultrasonic surgical instruments are finding increasingly widespread applications in surgical procedures by virtue of the unique performance characteristics of such instruments. Depending upon specific instrument configurations and operational parameters, ultrasonic surgical instruments can provide simultaneous or near-simultaneous cutting of tissue and hemostasis by coagulation, desirably minimizing patient trauma. Ultrasonic surgical instruments of this nature can be configured for open surgical use, laparoscopic, or endoscopic surgical procedures including robotic-assisted procedures.

FIGS. 4-18 are schematic diagrams illustrating an embodiment of an ultrasonic surgical instrument 100 that can be used as at least one instrument 50 within system 10. At least part of instrument 100 can be constructed and operable in accordance with the teachings of one or more of U.S. Pat. Nos. 5,322,055; 5,873,873; 5,980,510; 6,325,811; 6,783,524; 8,461,744, 9,023,071, 9,095,367, 9,393,037, U.S. Pub. No. 2006/0079874; U.S. Pub. No. 2007/0191713; U.S. Pub. No. 2007/0282333; U.S. Pub. No. 2008/0200940; and/or U.S. Pat. App. No. 61/410,603. Each of the foregoing patents, publications, and applications are incorporated by reference in their entirety. As described therein and in greater detail below, the instrument 100 can be configured to cut tissue, coagulate tissue, and to seal or weld tissue (e.g., blood vessels) substantially simultaneously. In other words, the instrument 100 operates similar to an endocutter type of stapler, except that the instrument 100 provides tissue welding through application of ultrasonic vibrational energy instead of providing lines of staples to join tissue.

Ultrasonic vibrational energy can separate tissue similar to severing of tissue by a translating blade positioned at the distal end of the surgical instrument. Vibrating at high frequencies (e.g., about 55,500 times per second), the ultrasonic blade can denature proteins in the tissue to form a sticky coagulum. Pressure exerted on tissue by the blade surface can collapse blood vessels and allow the coagulum to form a hemostatic seal. The precision of cutting and coagulation can be controlled by the surgeon's technique and adjusting one or more of the amplitude of the ultrasonic vibrations, the blade edge, tissue traction, and ultrasonic blade pressure.

As an example, the instrument 100 can have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instrument 100 can have various structural and functional similarities with the devices taught in any of the other references that are cited and incorporated by reference herein.

Figure 4:
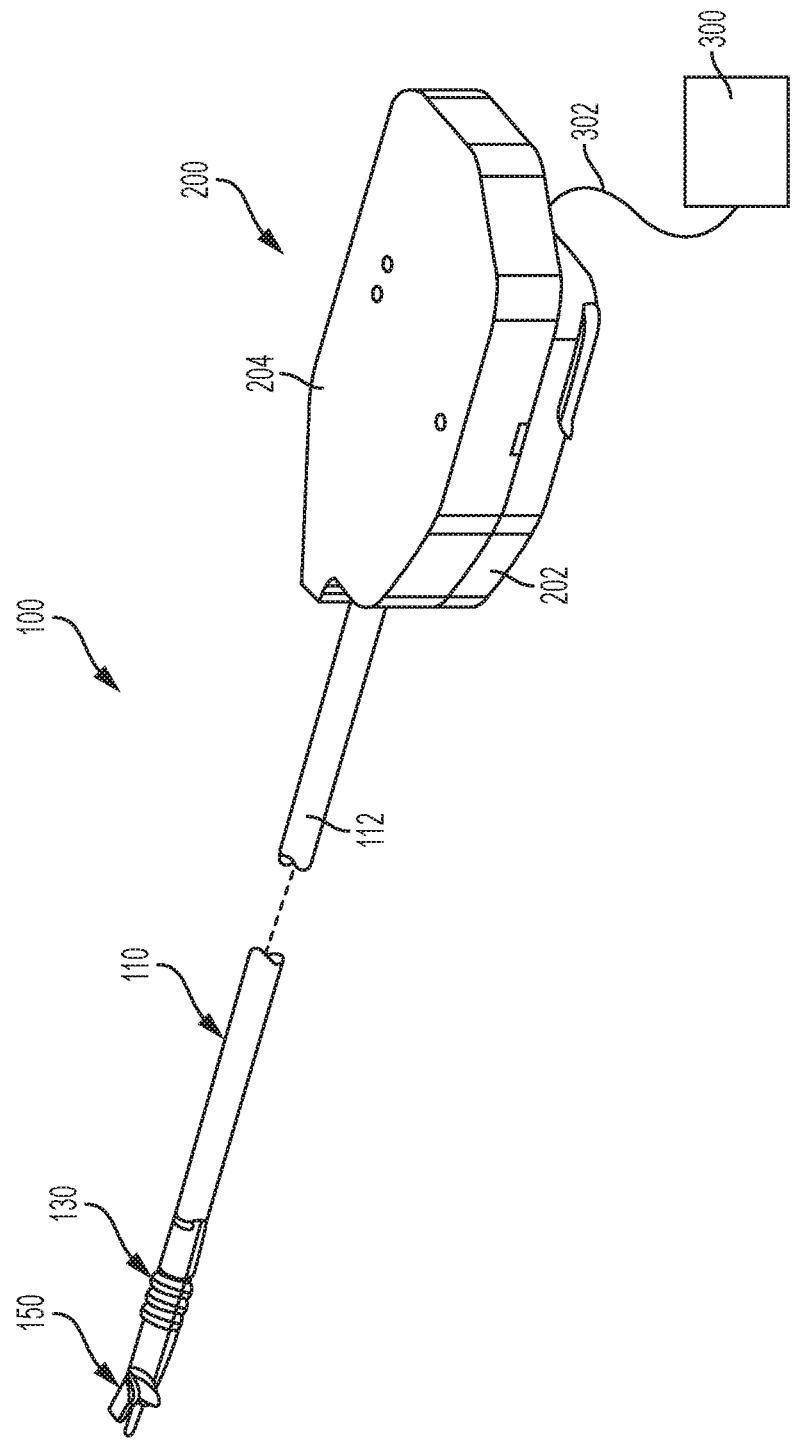
FIG. 4 is a perspective view illustrating an exemplary embodiment of a surgical instrument suitable for use with the robotic surgical system of FIG. 1.

As shown in FIG. 4, the instrument 100 includes an interface assembly 200, a shaft assembly 110, an articulation section 130, and an end effector 150. The interface assembly 200 can be configured to couple with the instrument dock 72 of the robotic arm cart 40 and it can be configured to drive the articulation section 130 and the end effector 150 as described in greater detail below. As also described in greater detail below, the instrument 100 can be configured to articulate end effector 150 to provide a desired positioning relative to tissue (e.g., a large blood vessel, etc.), then apply ultrasonic vibrational energy and/or RF energy to the tissue with end effector 150 to thereby cut, coagulate, and seal the tissue.

The instrument 100 includes an ultrasonic transducer 120, which can be operable to convert electrical power into ultrasonic vibrations. In some instances, the ultrasonic transducer 120 can receive power directly through dock 72. In some other instances, the transducer 120 can include a cable 302 that directly couples the ultrasonic transducer 120 with a generator 300. The generator 300 can include a power source and control module that can be configured to provide a power profile to transducer 120 that is suitable for the generation of ultrasonic vibrations through transducer 120. Optionally, the generator 300 can also be suitable for generation of RF signals.

In an embodiment, the generator 300 can include a GEN 300 sold by Ethicon Endo-Surgery, Inc. of Cincinnati, Ohio. In addition or in the alternative, the generator 300 can be constructed in accordance with at least some of the teachings of U.S. Pat. No. 8,986,302, entitled "Surgical Generator for Ultrasonic and Electrosurgical Devices," published Apr. 14, 2011, which is incorporated by reference in its entirety. Still other suitable forms that generator 300 can take, as well as various features and operabilities that generator 300 can provide, will be apparent to those of ordinary skill in the art in view of the teachings herein.

In an embodiment, at least part of the functionality of generator 300 can be incorporated directly into the interface assembly 200. As an example, the interface assembly 200 can include an integral battery or other integral power source, as well as any circuitry needed to condition power from a battery or other integral power source to drive ultrasonic transducer 120.

A. End Effector and Acoustic Drivetrain

Figure 6:
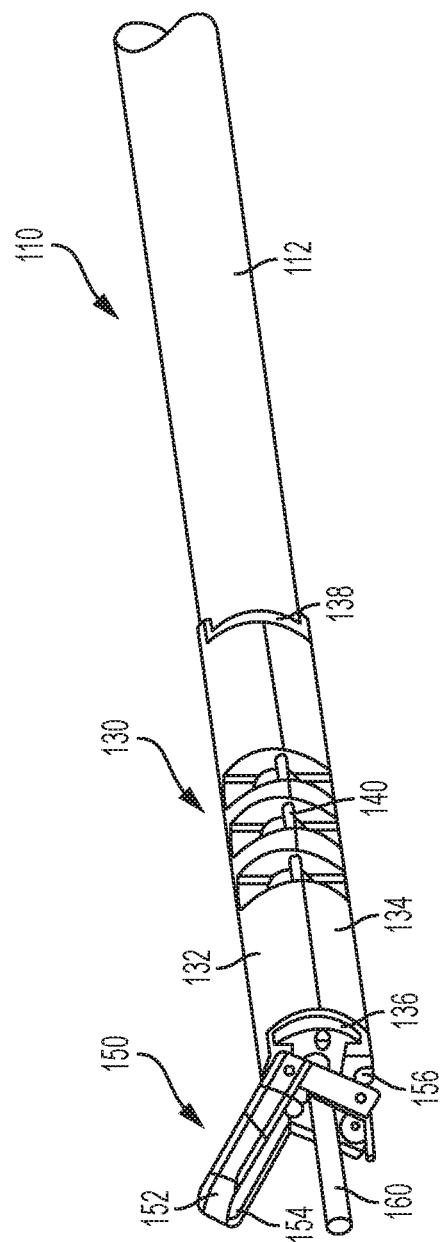
FIG. 6 is a perspective view illustrating exemplary embodiments of an end effector and a shaft assembly articulation section of the surgical instrument of FIG. 4.
Figure 7:
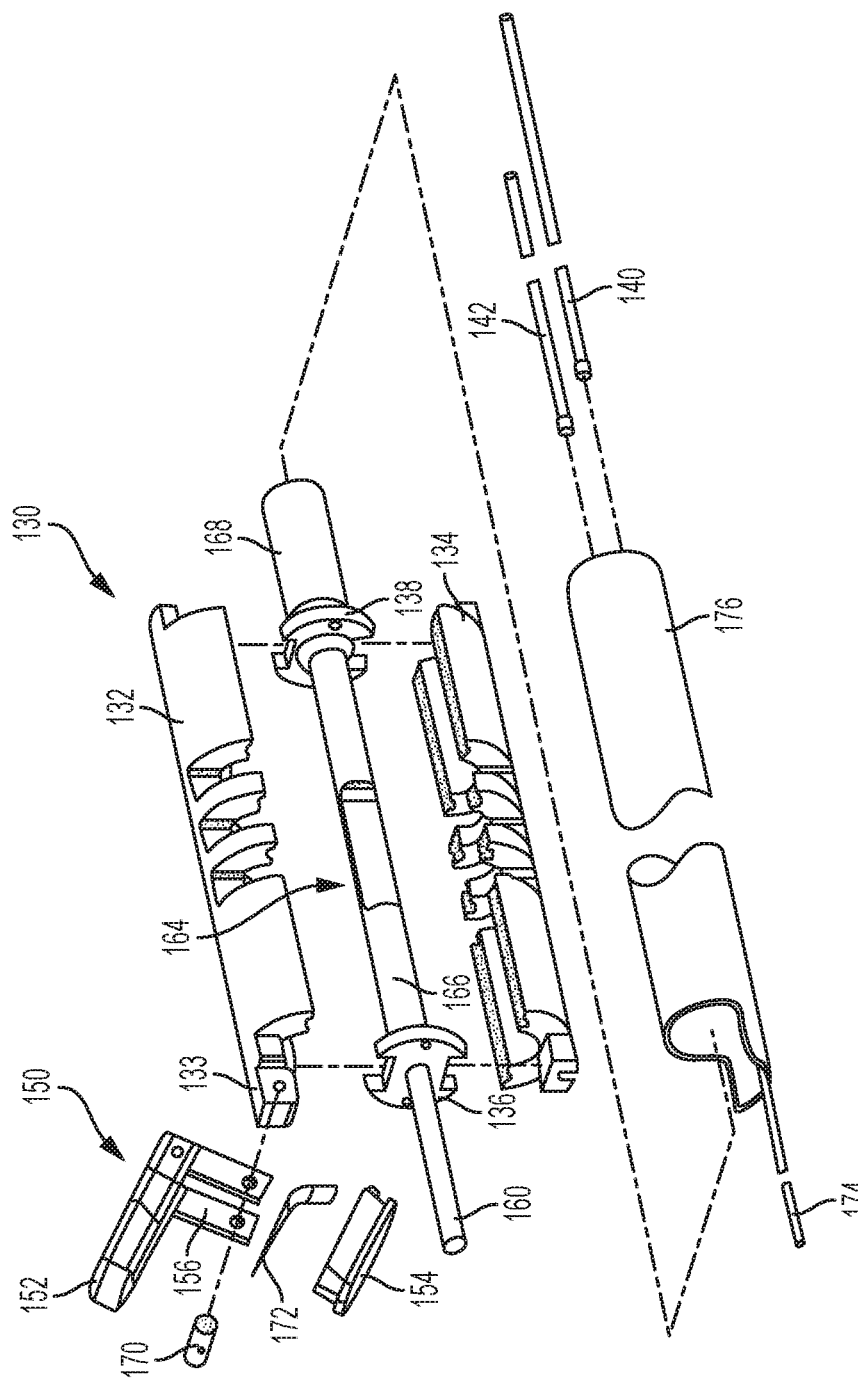
FIG. 7 is an exploded view the end effector and articulation section of FIG. 6.
Figure 8:
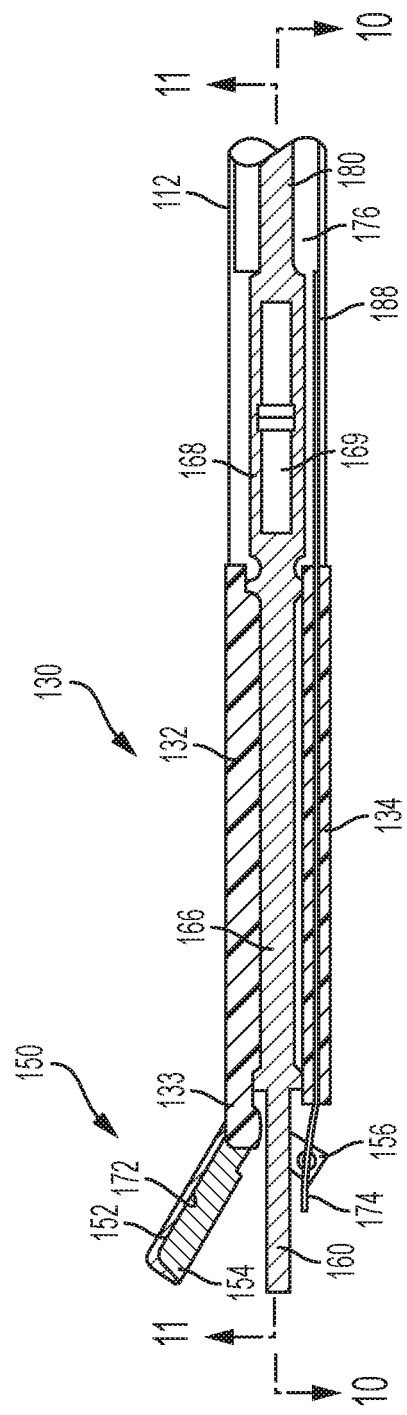
FIG. 8 is a lateral cross-sectional view of the end effector and articulation section of FIG. 6.
Figure 9:
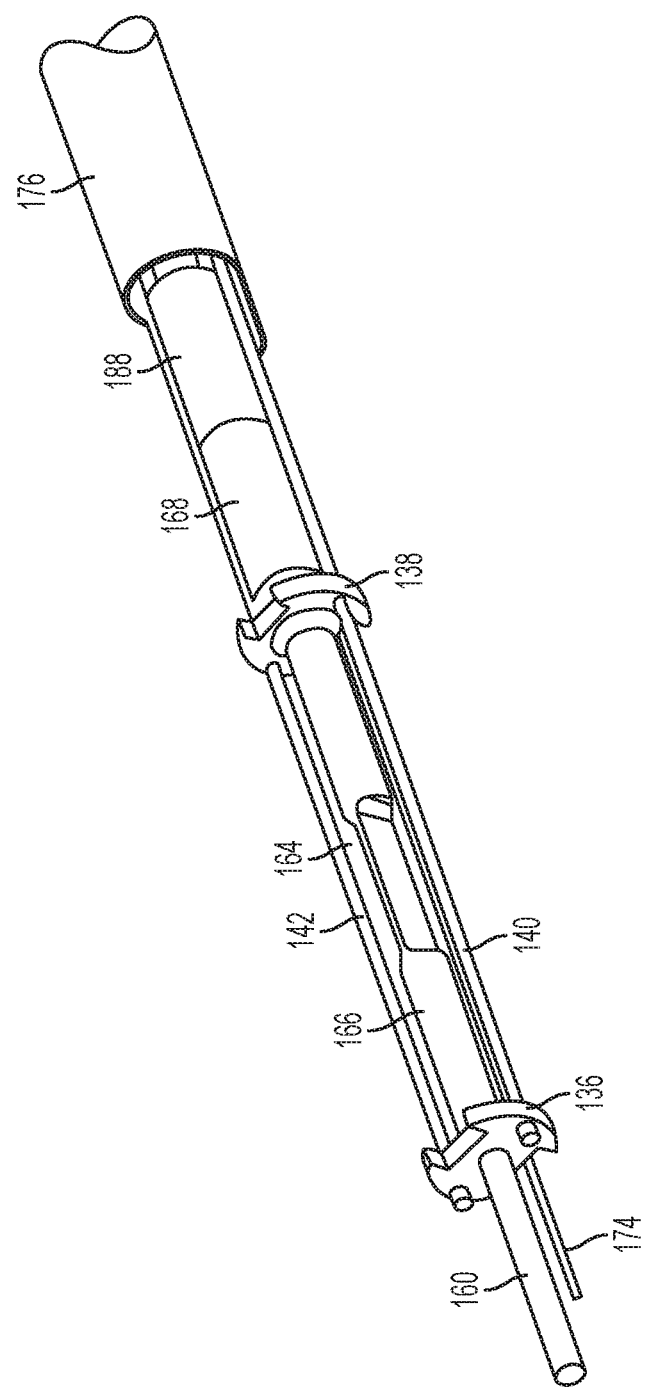
FIG. 9 is a perspective view of the end effector and articulation section of FIG. 6, omitting an outer sheath and clamp pad features for clarity.
Figure 10:
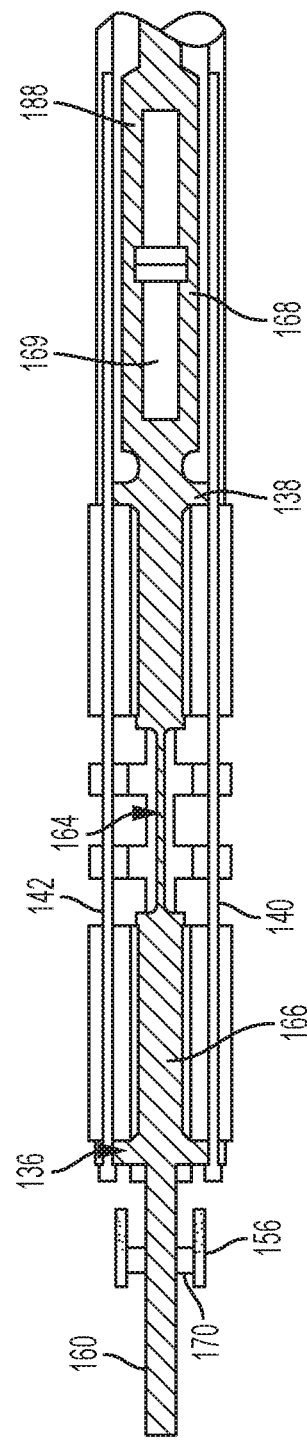
FIG. 10 is a cross-sectional view of the end effector and articulation section of FIG. 6, taken along line 10-10 of FIG. 8.
Figure 11:
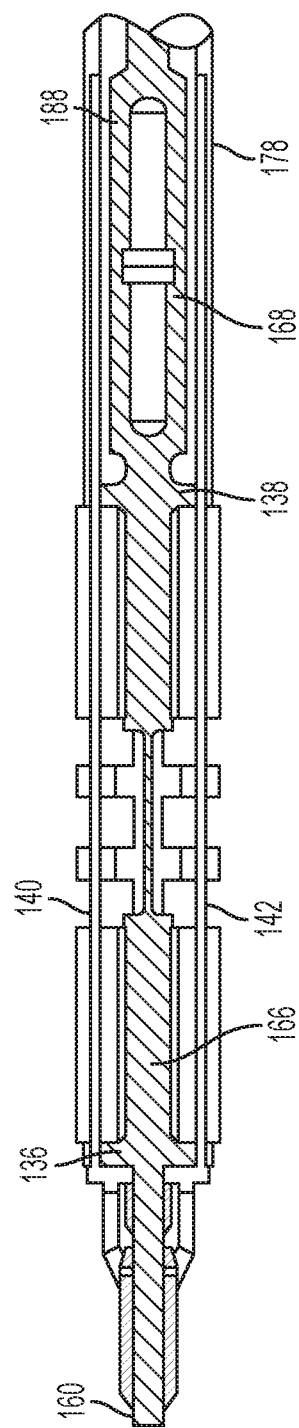
FIG. 11 is a cross-sectional view of the end effector and articulation section of FIG. 6, taken along line 11-11 of FIG. 8.
Figure 12:
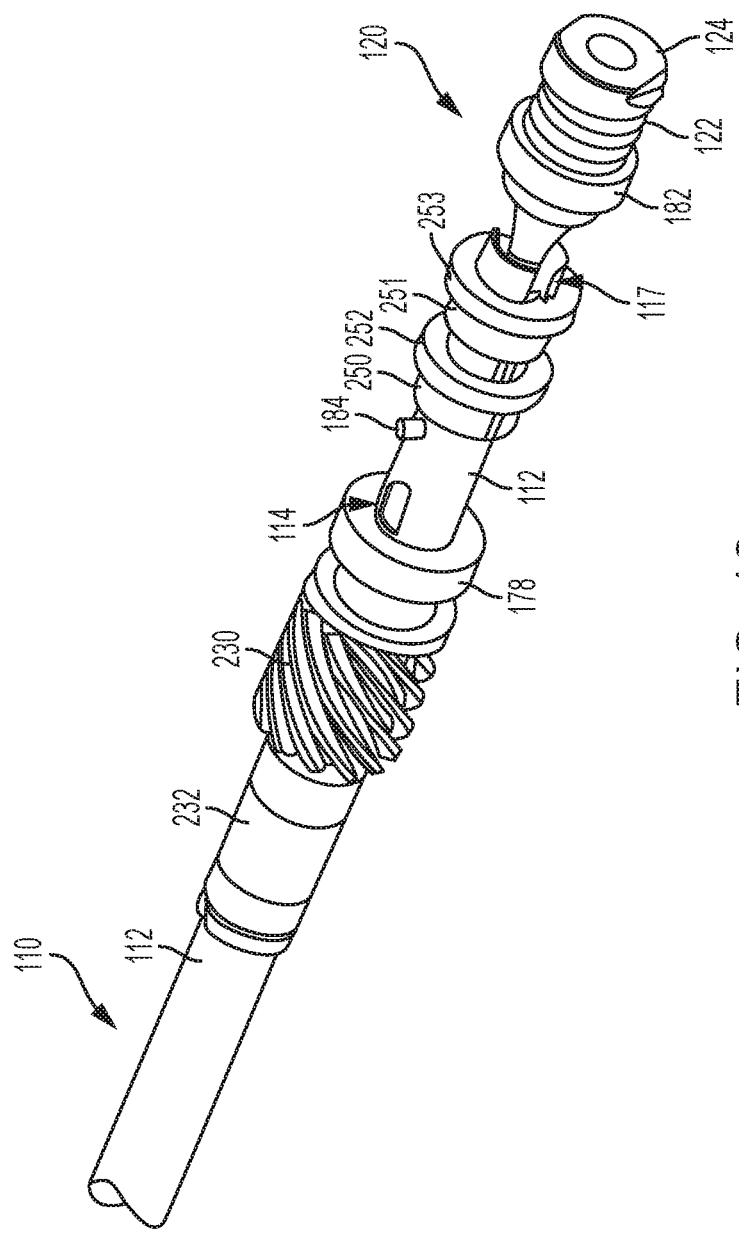
FIG. 12 is a perspective view of a proximal end of the shaft assembly of the surgical instrument of FIG. 4.

As illustrated in FIGS. 6-8, the end effector 150 can include a clamp arm 152 and an ultrasonic blade 160. The clamp arm 152 includes a clamp pad 154 that is secured to the underside of clamp arm 152, facing the ultrasonic blade 160. The clamp arm 152 can be pivotally secured to a distally projecting tongue 133 (FIGS. 7-8) of a first ribbed body portion 132. The first ribbed body portion 132 can form part of the articulation section 130, as described in greater detail below. The clamp arm 152 is operable to selectively pivot toward and away from the ultrasonic blade 160 to selectively clamp tissue between the clamp arm 152 and the ultrasonic blade 160. A pair of arms 156 extend transversely to clamp arm 152 and are secured to a pin 170 that extends laterally between arms 156. A rod 174 is secured to pin 170. Rod 174 extends distally from a closure tube 176 and is unitarily secured to closure tube 176.

Figure 13:
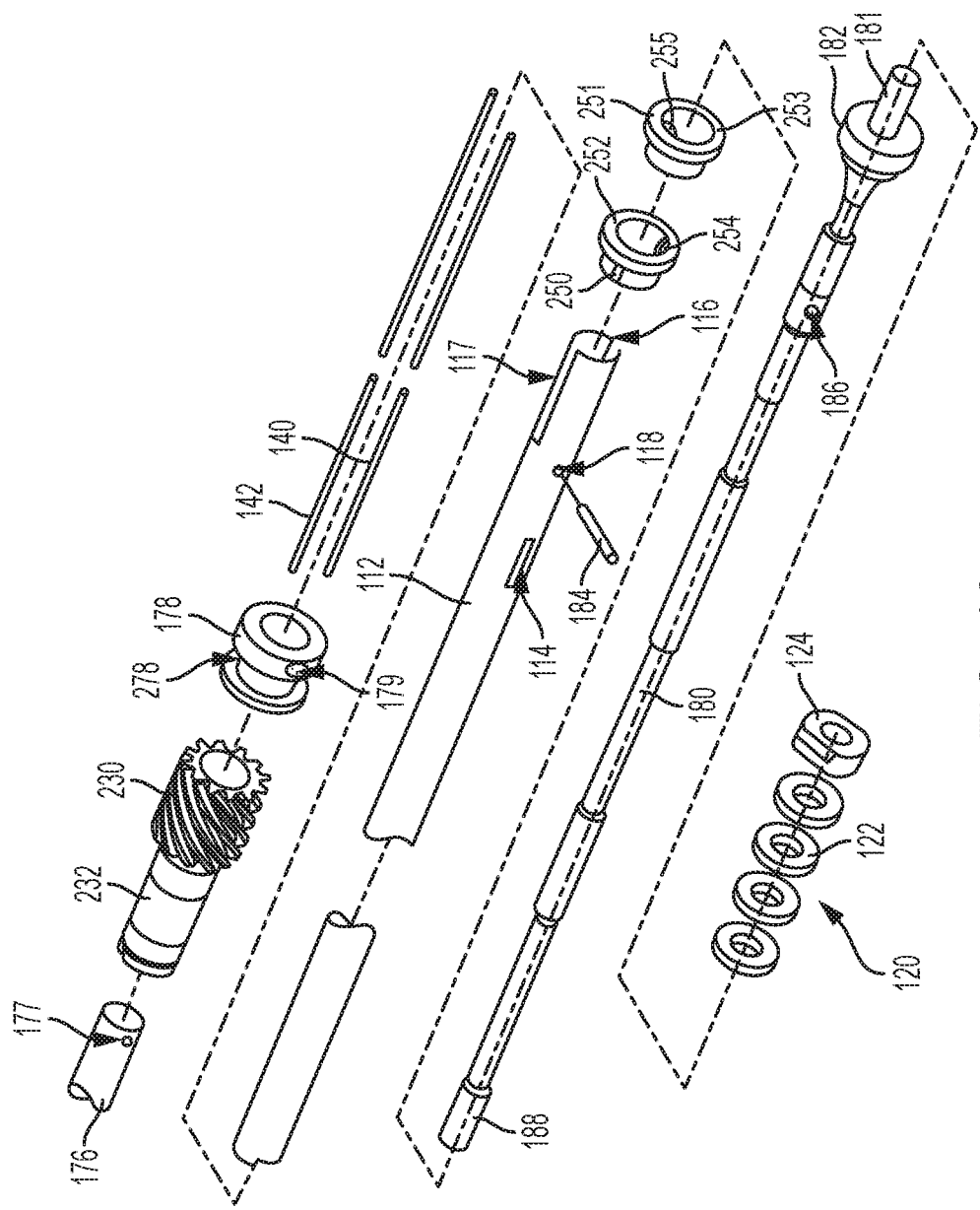
FIG. 13 is an exploded view of the proximal end of the shaft assembly of the instrument of FIG. 4.

A driving ring 178 can be secured to the proximal end of closure tube 176. In particular, and as illustrated in FIG. 13, the proximal end of closure tube 176 can include a transverse opening 177 that can be configured to align with a transverse opening 179 of the driving ring 178. The openings 177, 179 are configured to receive a set screw (not shown) or other feature that can secure the driving ring 178 to the closure tube 176. The driving ring 17$ is slidably and coaxially disposed about the exterior of the outer sheath 112; while the closure tube 176 is slidably and coaxially disposed within the interior of the outer sheath 112. However, the outer sheath 112 can include a longitudinally extending slot 114 that can be configured to receive the set screw and it can secure the driving ring 178 to the closure tube 176. Thus, the slot 114 can allow the driving ring 178 and the closure tube 176 to translate together relative to the outer sheath 112. The positioning of the set screw in the slot 114 can also provide rotation of the closure tube 176 and the driving ring 178 about the longitudinal axis of outer sheath 112 when the outer sheath 112 is rotated about its longitudinal axis, as described in greater detail below.

As also described in greater detail below, the interface assembly 200 can include features that are operable to drive the driving ring 178, the closure tube 176, and the rod 174 longitudinally relative to the outer sheath 112 and relative to the articulation section 130. It can be understood that this translation of the driving ring 178, the closure tube 176, and the rod 174 can provide pivoting of the clamp arm 152 toward the ultrasonic blade 160 when the ring 178, the tube 176, and the rod 174 are translated proximally; or away from the ultrasonic blade 160 when the ring 178, the tube 176, and the rod 174 are translated distally. The rod 174 can be sufficiently flexible to bend with the articulation section 130. However, the rod 174 can have sufficient tensile and compressive strength to drive the clamp arm 152 when the rod 174 is translated, regardless of whether the articulation section 130 is in a straight or bent configuration.

As illustrated in FIGS. 7-8 a leaf spring 172, is captured between the clamp arm 152 and the clamp pad 154 and it abuts the distal face of tongue 133. The leaf spring 172 can be resiliently biased to drive the clamp arm 152 away from the ultrasonic blade 160 to the open position, shown in FIGS. 4, 6, and 8. The leaf spring 172 can therefore further bias the tube 176 and the rod 174 distally. Of course, like other components described herein, the leaf spring 172 can be omitted if desired. Furthermore, the clamp arm 152 and the clamp pad 154 can be omitted if desired.

Embodiments of the ultrasonic blade 160 can be configured to vibrate at ultrasonic frequencies in order to effectively cut through and seal tissue, particularly when the tissue is being clamped between the damp pad 154 and the ultrasonic blade 160. The ultrasonic blade 160 can be positioned at the distal end of an acoustic drivetrain.

This acoustic drivetrain includes the ultrasonic transducer 120, a rigid acoustic waveguide 180, and a flexible acoustic waveguide 166. As best seen in FIGS. 5 and 12-17, ultrasonic transducer 120 includes a set of piezoelectric discs 122 located proximal to a horn 182 of rigid acoustic waveguide 180. Piezoelectric discs 122 are coaxially positioned along a proximally extending bolt 181, which is a unitary feature of acoustic waveguide 180 located proximal to horn 182. An endmass nut 124 is secured to bolt 181, thereby securing piezoelectric discs 122 to rigid acoustic waveguide 180. As noted above, piezoelectric discs 122 are operable to convert electrical power into ultrasonic vibrations, which are then transmitted along rigid acoustic waveguide 180 to the ultrasonic blade 160. The rigid acoustic waveguide 180 is illustrated FIGS. 13 and 17-18. As shown in FIG. 13, rigid acoustic waveguide 180 includes a transverse opening 186 that complements a transverse opening 118 formed in outer sheath 112. A pin 184 is disposed in openings 118, 186 to couple outer sheath 112 with rigid acoustic waveguide 180. This coupling provides rotation of acoustic waveguide 180 and the rest of the acoustic drivetrain about the longitudinal axis of outer sheath 112 when outer sheath 112 is rotated about its longitudinal axis as will be described in greater detail below. As an example, the opening 186 can be located at a position corresponding to a node associated with resonant ultrasonic vibrations communicated through rigid acoustic waveguide 180.

The rigid acoustic waveguide 180 distally terminate in a coupling 188, which can be seen in FIGS. 8-11 and 13. The coupling 188 is secured to the coupling 168 by a double-threaded bolt 169. The coupling 168 is located at the proximal end of the flexible acoustic waveguide 166. As illustrated in FIGS. 7-11, the flexible acoustic waveguide 166 includes a distal flange 136, a proximal flange 138, and a narrowed section 164 located between flanges 138. As an example, the flanges 136, 138 can be located at positions corresponding to nodes associated with resonant ultrasonic vibrations communicated through the flexible acoustic waveguide 166. The narrowed section 164 can be configured to allow flexible acoustic waveguide 166 to flex without significantly affecting the ability of flexible acoustic waveguide 166 to transmit ultrasonic vibrations. The narrowed section 164 can be configured in accordance with one or more teachings of U.S. patent application Ser. No. 13/538,588 and/or U.S. patent application Ser. No. 13/657,553, each of which are incorporated by reference in their entirety. Either of the waveguides 166, 180 can be configured to amplify mechanical vibrations transmitted through the waveguides 166, 180. Furthermore, either of the waveguides 166, 180 can include features operable to control the gain of the longitudinal vibrations along the waveguides 166, 180 and/or features to tune the waveguides 166, 180 to the resonant frequency of the system.

The distal end of the ultrasonic blade 160 can be located at a position corresponding to an anti-node associated with resonant ultrasonic vibrations communicated through the flexible acoustic waveguide 166, in order to tune the acoustic assembly to a preferred resonant frequency $f_o$ when the acoustic assembly is not loaded by tissue. When the ultrasonic transducer 120 is energized, the distal end of the ultrasonic blade 160 can be configured to move longitudinally in the range from, for example, approximately 10 to 500 microns peak-to-peak, and in some instances in the range from about 20 microns to about 200 microns at a predetermined vibratory frequency $f_o$ (e.g., about 55.5 kHz). When the ultrasonic transducer 120 is activated, these mechanical oscillations are transmitted through the waveguides 180, 166 to reach the ultrasonic blade 160, thereby providing oscillation of the ultrasonic blade 160 at the resonant ultrasonic frequency. Thus, when tissue is secured between the ultrasonic blade 160 and the clamp pad 154, the ultrasonic oscillation of the ultrasonic blade 160 can simultaneously sever the tissue and denature the proteins in adjacent tissue cells, thereby providing a coagulative effect with relatively little thermal spread. In some versions, an electrical current can also be provided through the ultrasonic blade 160 and the clamp arm 152 to also cauterize the tissue.

While some configurations for an acoustic transmission assembly and ultrasonic transducer 120 have been described, still other suitable configurations for an acoustic transmission assembly and the ultrasonic transducer 120 will be apparent to one or ordinary skill in the art in view of the teachings herein. Similarly, other suitable configurations for the end effector 150 will be apparent to those of ordinary skill in the art in view of the teachings herein.

B. Exemplary Shaft Assembly and Articulation Section

The shaft assembly 110 can extend distally from the interface assembly 200. The articulation section 130 can be located at the distal end of the shaft assembly 110, with the end effector 150 being located distal to articulation section 130. The shaft assembly 110 can include an outer sheath 112 that encloses drive features and the above-described acoustic transmission features that couple the interface assembly 200 with the articulation section 130 and the end effector 150. The shaft assembly 110 can be rotatable about the longitudinal axis defined by the outer sheath 112, relative to interface assembly 200. Such rotation can provide rotation of the end effector 150, the articulation section 130, and the shaft assembly 110 unitarily. Of course, rotatable features can simply be omitted if desired.

The articulation section 130 is operable to selectively position the end effector 150 at various lateral deflection angles relative to the longitudinal axis defined by the outer sheath 112. The articulation section 130 can take a variety of forms. As an example, the articulation section 130 can be configured in accordance with one or more teachings of U.S. Patent Publication. No. 2012/0078247, the entirety of which is incorporated by reference. Alternatively or additionally, the articulation section 130 can be configured in accordance with one or more teachings of U.S. patent application Ser. No. 13/538,588 and/or U.S. patent application Ser. No. 13/657,553, each of which are incorporated by reference in their entirety. Various other suitable forms that the articulation section 130 can take will be apparent to those of ordinary skill in the art in view of the teachings herein. It should also be understood that some versions of instrument 100 can omit the articulation section 130.

As illustrated in FIGS. 6-11, the articulation section 130 can include the first ribbed body portion 132 and a second ribbed body portion 134, with a pair of articulation bands 140, 142 extending through channels defined at the interfaces between the ribbed body portions 132, 134. The ribbed body portions 132, 134 can be substantially longitudinally positioned between the flanges 136, 138 of the flexible acoustic waveguide 166. The distal ends of the articulation bands 140, 142 can be unitarily secured to distal flange 136. The articulation bands 140, 142 can also pass through the proximal flange 138, yet articulation bands 140, 142 can be slidable relative to the proximal flange 138.

Figure 17:
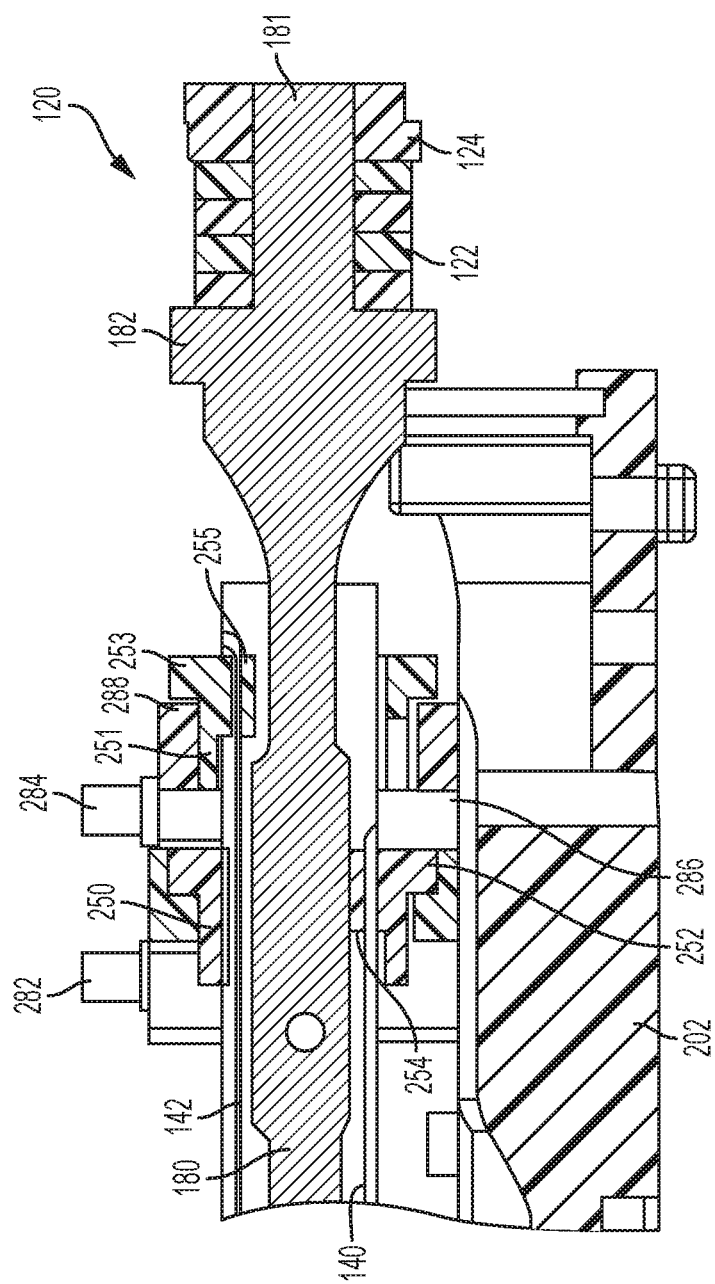
FIG. 17 is a lateral cross-sectional view of a proximal portion of the proximal end of the instrument of FIG. 4, taken along line 17-17 of FIG. 15.
Figure 18:
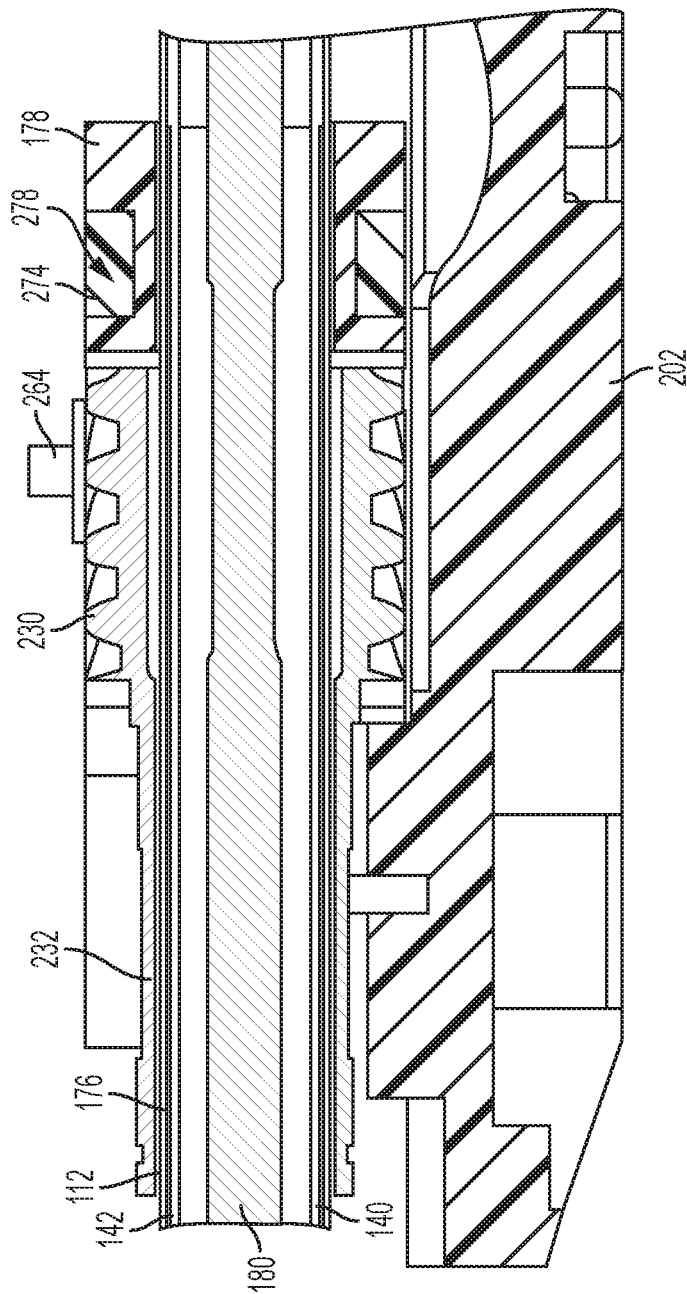
FIG. 18 is a lateral cross-sectional view of a distal portion of the proximal end of the instrument of FIG. 4, taken along line 18-18 of FIG. 15

The proximal end of the articulation band 140 can be secured to a first drive ring 250; while the proximal end of articulation band 142 can be secured to a second drive ring 251. As illustrated in FIGS. 13 and 17, the first drive ring 250 includes an annular flange 252 and an inwardly projecting anchor feature 254; while the second drive ring 251 also includes an annular flange 253 and an inwardly projecting anchor feature 255. The proximal end of articulation band 140 can be fixedly secured within the anchor feature 254 while the proximal end of articulation band 142 can be fixedly secured within the anchor feature 255. The drive rings 250, 251 can be slidably disposed about the proximal end of outer sheath 112. The outer sheath 112 can include a pair of longitudinally extending slots 116, 117 that are configured to respectively receive the anchor features 254, 255. The slots 116, 117 can allow the drive rings 250, 251 to translate relative to outer sheath 112. The positioning of the anchor features 254, 255 in the slots 116, 117 can also provide rotation of the rings 250, 251 and the articulation bands 140, 142 about the longitudinal axis of the outer sheath 112 when the outer sheath 112 is rotated about its longitudinal axis as described in greater detail below.

As described in greater detail below, the interface assembly 200 is operable to selectively pull one of the articulation bands 140, 142 proximally by pulling proximally on the drive ring 250; while simultaneously allowing the other one of the articulation bands 140, 142 and the drive ring 251 to translate distally. It should be understood that, as one of the articulation bands 140, 142 is pulled proximally, this will cause articulation section 130 to bend, thereby laterally deflecting the end effector 150 away from the longitudinal axis of the shaft assembly 110 at an articulation angle. In particular, the end effector 150 will be articulated toward the one of the articulation bands 140, 142 that is being pulled proximally. During such articulation, the other of the articulation bands 140, 142 will be pulled distally by the flange 136. The ribbed body portions 132, 134 and the narrowed section 164 can all be sufficiently flexible to accommodate the above-described articulation of the end effector 150.

C. Exemplary Robotic Arm Interface Assembly

The interface assembly 200 is illustrated in greater detail in FIGS. 5 and 14-48. As shown, the interface assembly 200 comprises a base 202 and a housing 204. For clarity, the housing 204 is only shown in FIG. 4 and is omitted from FIGS. 5 and 14-18. The housing 204 can include a shell that encloses drive components. In certain embodiments, the housing 204 can also include an electronic circuit board, chip, and/or other features that can be configured to identify the instrument 100.

The base 202 is configured to engage the dock 72 of the robotic arm cart 40. While not shown, it should be understood that the base 202 can also include one or more electrical contacts and/or other features operable to establish electrical communication with a complementary features of the dock 72. A shaft support structure 206 extends upwardly from the base 202 and it can provide support to the shaft assembly 110 while still allowing the shaft assembly 110 to rotate. By way of example only, the shaft support structure 206 can include a busing, bearings, and/or other features that facilitate rotation of the shaft assembly 110 relative to the support structure 206.

Figure 5:
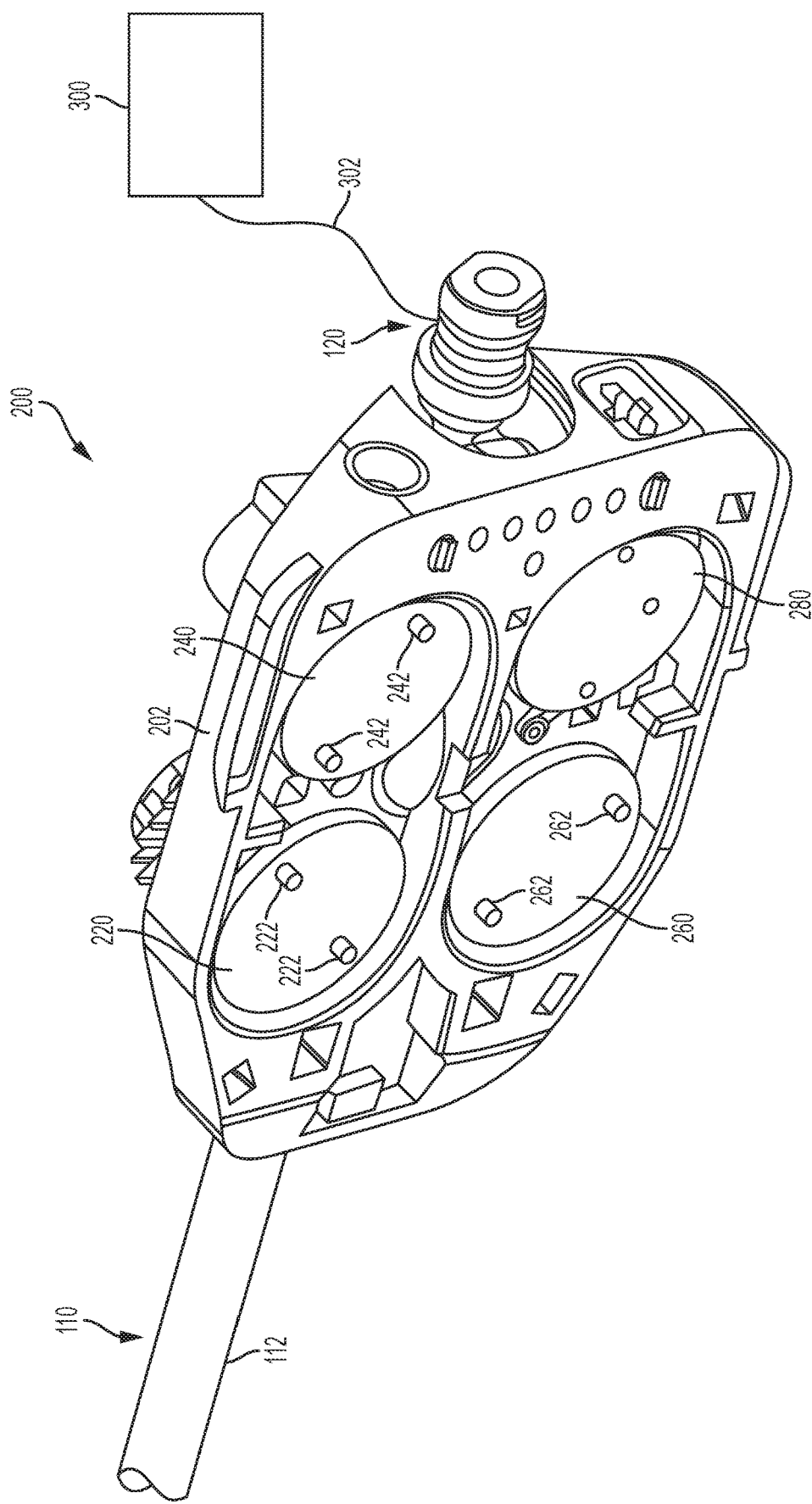
FIG. 5 is a perspective view illustrating an underside of a base assembly of the surgical instrument of FIG. 4.

As shown in FIG. 5, the base 202 further include three drive discs 220, 240, 260 that are rotatable relative to the base 202. Each of the discs 220, 240, 260 includes a respective pair of unitary pins 222, 242, 262 that couple with complementary recesses not shown in drive elements of dock 72. In certain embodiments, one pin 222, 242 262 of each pair can be closer to the axis of rotation of the corresponding disc 220, 240, 260 to ensure proper angular orientation of discs 220, 240, 260 relative to the corresponding drive element of the dock 72.

Figure 14:
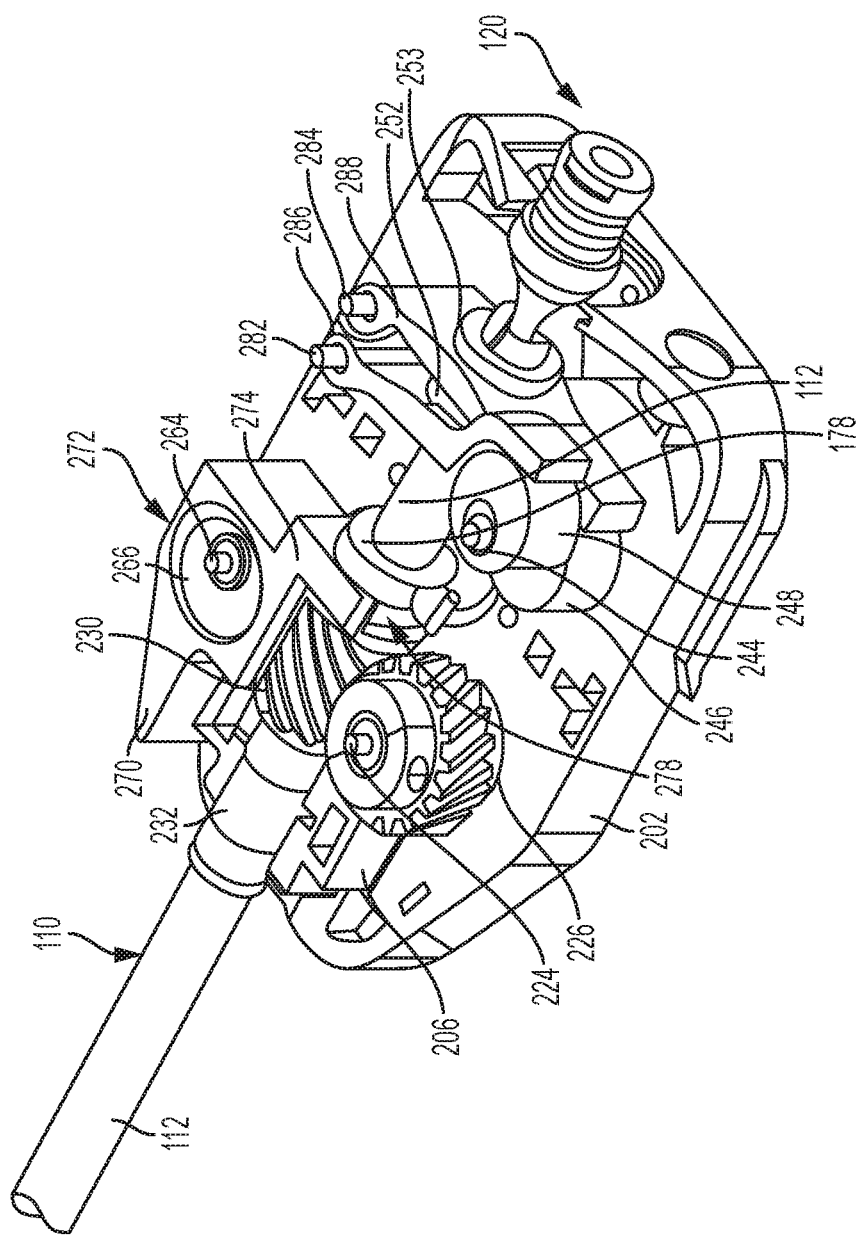
FIG. 14 is a perspective view of the proximal end of the instrument of FIG. 4, with the outer cover omitted.
Figure 15:
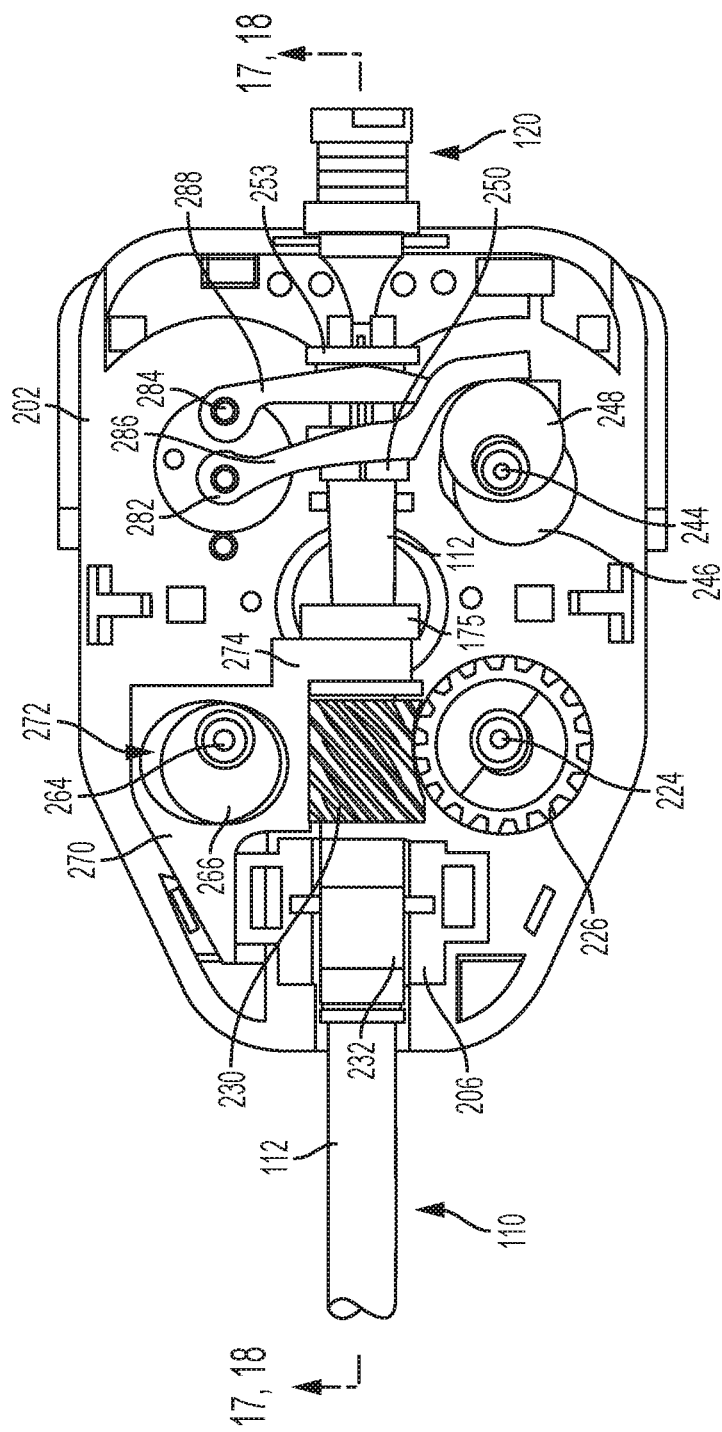
FIG. 15 is a top down view of the proximal end of the instrument of FIG. 4, with the outer cover omitted.
Figure 16:
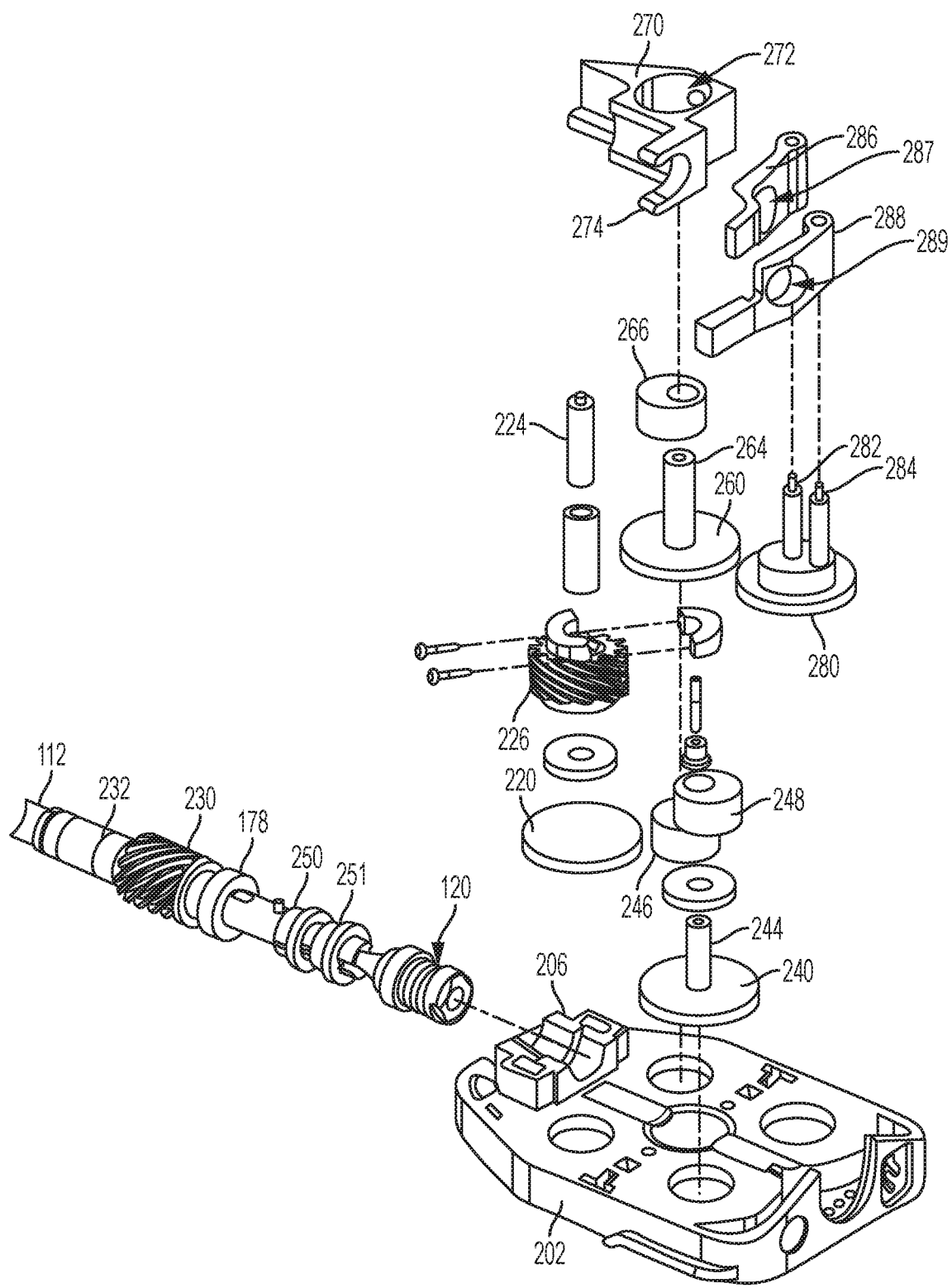
FIG. 16 is an exploded view of the proximal end of the instrument of FIG. 4, with the outer cover omitted.

As illustrated in FIGS. 14-16, a drive shaft 224, 244, 264 extends unitarily upwardly from each of the discs 220, 240, 260. As described in greater detail below, the discs 220, 240, 260 can be independently operable to provide independent rotation of the shaft assembly 110, bending of the articulation section 130, and translation of the closure tube 176, through independent rotation of the drive shafts 224, 244, 264. The base 202 can also include an idle disc 280, which does not rotate or drive any components. A pair of fixed pivot pins 282, 284 can extend unitarily upwardly from disc 280.

As illustrated in FIGS. 14-16, a first helical gear 226 can be fixedly secured to drive shaft 224, such that rotation of the corresponding disc 220 provides rotation of the first helical gear 226. The first helical gear 226 meshes with a second helical gear 230, which is unitarily secured to a sleeve 232. The sleeve 232 is unitarily secured to the outer sheath 112. Thus, rotation of the first helical gear 226 provides rotation of the shaft assembly 110. Rotation of the first helical gear 226 about a first axis is converted into rotation of second helical gear 230 about a second axis, which can be orthogonal to the first axis. A clockwise (CW) rotation of the second helical gear 230 (viewed from the top down) can result in CW rotation of the shaft assembly 110 (viewed from the distal end of shaft assembly 110) toward the proximal end of the shaft assembly 110, depending on the thread orientation of helical gears 226, 230. A counter-clockwise (CCW) rotation of second helical gear 132 (viewed from the top down) results in CCW rotation of the shaft assembly 110 (viewed from the distal end of shaft assembly 110) toward the proximal end of the shaft assembly 110, again depending on the thread orientation of helical gears 226, 230. It should therefore, be understood that shaft assembly 110 can be actuated by rotating drive shaft 224. Other suitable ways in which the shaft assembly 110 can be rotated will be apparent to those of ordinary skill in the art in view of the teachings herein.

As illustrated in FIGS. 14-16, a pair of cylindraceous cams 246, 248 are fixedly secured to the drive shaft 244, such that rotation of the corresponding disc 240 provides rotation of the cams 246, 248. The cams 246, 248 can each be mounted eccentrically to the drive shaft 244, such that the longitudinal axes of the cams 246, 248 are offset from, yet parallel to, the longitudinal axis of the drive shaft 244. In addition, the cams 246, 248 can be offset in an opposing manner, such that the cams 246, 248 laterally protrude relative to the drive shaft 244 in opposite directions. The cams 246, 248 can be positioned to drive the pivot arms 286, 288. The pivot arm 286 can be pivotally coupled with the pivot pin 282; while the pivot arm 288 can be pivotally coupled with the pivot pin 284. The first drive ring 250 can pass through an opening 287 formed through the first drive arm 286; while the second drive ring 251 can pass through an opening 289 formed through the second drive arm 288. Flanges 252, 253 can each have an outer diameter that can be larger than the inner diameter of the corresponding opening 287, 289. The flanges 252, 253 can thus restrict distal movement of the rings 250, 251 relative to respective drive arms 286, 288.

As the drive shaft 244 is rotated, one of the cams 246, 248 will push proximally on the corresponding arm 286, 288, depending on the positioning of these components and the angular position of vcams 246, 248 at the time of rotation. In some instances, vcam 246 can drive the arm 288 proximally, such that the arm 288 pivots CCW (viewed from the top down) about the pin 284. The arm 288 will bear against the flange 253 during such pivoting, thereby pulling the ring 251 and the articulation band 142 proximally. This proximal movement of the articulation band 142 will cause the articulation section 130 to bend, with the end effector 150 being deflected toward the hand 142. This bending of the articulation section 130 will pull the articulation band 140 distally, which will in turn pull the ring 250 and its flange 252 distally. The distal motion of flange 252 will drive arm 286 distally, such that arm 286 pivots CW (viewed from the top down) about the pin 282. The cam 248 can be oriented to permit such distal pivoting of the arm 286. As the drive shaft 244 continues to rotate, or if drive shaft 244 is rotated in the opposite direction, the above pushing and pulling will eventually be reversed. In other words, the cam 248 can drive the arm 286 proximally while the cam 246 can permit the arm 288 to pivot distally during bending of the articulation section 130 to provide deflection of the end effector 150 toward the band 140. It should therefore be understood that articulation section 130 may be actuated by rotating drive shaft 244. Other suitable ways in which the articulation section 130 can be actuated will be apparent to those of ordinary skill in the art in view of the teachings herein.

As illustrated in FIGS. 14-16, a cylindraceous cam 266 can be fixedly secured to the drive shaft 264, such that rotation of the corresponding disc 260 can provide rotation of the cam 266. The cam 266 can be mounted eccentrically to the drive shaft 264, such that the longitudinal axis of the cam 266 can be offset from yet parallel to the longitudinal axis of the drive shaft 264, the cam 266 can be disposed in an oblong opening 272 formed through a rack 270, which can be translatable relative to the base 202. The rack 270 includes a laterally extending fork 274. The fork 274 can be disposed in an annular recess 278 of the driving ring 178 which can be secured to the closure tube 176 as noted above. The configuration of the cam 266 and the configuration of the opening 272 can provide a relationship whereby the rack 270 translates longitudinally in response to rotation of the drive shaft 264 and the cam 266. This translation of the rack 270 can provide translation of the closure tube 176 due to the engagement between the fork 274 and the driving ring 178; and the engagement between the driving ring 178 and the closure tube 176. The clamp arm 152 can be selectively driven away from or toward the ultrasonic blade 160 by rotating the drive shaft 264. Other suitable ways in which the clamp arm 152 can be actuated will be apparent to those of ordinary skill in the art in view of the teachings herein.

D. Exemplary Operation

In use, the arm cart 40 can be used to insert the end effector 150 into a patient via a trocar. The articulation section 130 can be substantially straight, and the clamp arm 152 can be pivoted toward the ultrasonic blade 160, when the end effector 150 and part of the shaft assembly 110 are inserted through the trocar. The drive shaft 224 can be rotated through drive features in the dock 72 that are coupled with the corresponding disc 220, to position the end effector 150 at a desired angular orientation relative to the tissue. The drive shaft 244 can then be rotated through drive features in the dock 72 that are coupled with the corresponding disc 240, to pivot or flex the articulation section 130 of the shaft assembly 110 in order to position the end effector 150 at a desired position and orientation relative to an anatomical structure within the patient. The drive shaft 264 can then be rotated through drive features in the dock 72 that are coupled with the corresponding disc 260, to pivot the clamp arm 152 away from the ultrasonic blade 160, thereby effectively opening the end effector 150.

Tissue of the anatomical structure can be then captured between the clamp pad 154 and the ultrasonic blade 160 by rotating the drive shaft 264 to advance the closure tube 176 distally, by actuating drive features in the dock 72 that are coupled with the corresponding disc 260. In some instances, this can involves clamping two layers of tissue forming part of a natural lumen defining anatomical structure (e.g., a blood vessel, portion of gastrointestinal tract, portion of reproductive system, etc.) in a patient. However, it should be understood that embodiments of the instrument 100 can be used on various kinds of tissues and anatomical locations. With tissue captured between the clamp pad 154 and the ultrasonic blade 160, the ultrasonic transducer 120 can be activated to provide ultrasonic vibrations to the ultrasonic blade 160. This can simultaneously sever the tissue and denature proteins in adjacent tissue cells, thereby providing a coagulative effect with relatively little thermal spread.

The above operation of the shaft assembly 110, the articulation section 130, and the end effector 150 can be repeated as many times as desired in various locations within the patient. When the operator wishes to withdraw the end effector 150 from the patient, the drive shaft 244 can be rotated through drive features in the dock 72 that are coupled with the corresponding disc 240, to straighten the articulation section 130. The drive shaft 264 can be rotated through drive features in the dock 72 that are coupled with the corresponding disc 260, to pivot the clamp arm 152 toward the ultrasonic blade 160, thereby effectively closing the end effector 150. The arm cart 40 can be then used to withdraw the end effector 150 from the patient and trocar. Other suitable ways in which instrument 100 can be operable and operated will be apparent to those of ordinary skill in the art in view of the teachings herein.

III. Treatment Protocols for Cutting, Coagulating, and Sealing Tissue

A. Control System

The control system 39 can be configured to implement one or more treatment protocols for cutting, coagulating, and sealing tissue. As discussed in detail below, the control system 39 can be implemented using one or more computer systems, which may also be referred to herein as digital data processing systems and programmable systems.

One or more aspects or features of the control system 39 can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with the user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 19:
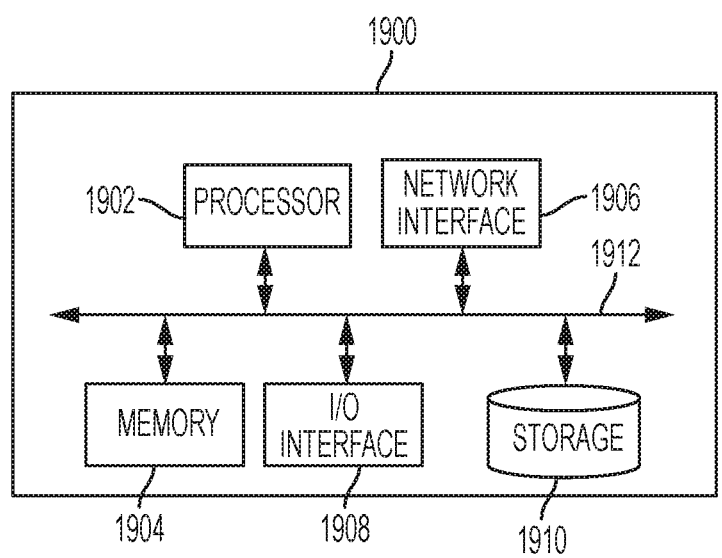
FIG. 19 is a block diagram illustrating an exemplary embodiment of a control system suitable for use with the robotic surgical system of FIG. 1.

An exemplary embodiment of the control system 39 is illustrated FIG. 19 as computer system 1900. As shown, the computer system 1900 includes one or more processors 1902 which can control the operation of the computer system 1900. "Processors" are also referred to herein as "controllers." The processor(s) 1902 can include any type of microprocessor or central processing unit (CPU), including programmable general-purpose or special-purpose microprocessors and/or any one of a variety of proprietary or commercially available single or multi-processor systems. The computer system 1900 can also include one or more memories 1904, which can provide temporary storage for code to be executed by the processor(s) 1902 or for data acquired from one or more users, storage devices, and/or databases. The memory 1904 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 600 can be coupled to a bus system 1912. The illustrated bus system 1912 is an abstraction that represents any one or more separate physical busses, communication lines/interfaces, and/or multi-drop or point-to-point connections, connected by appropriate bridges, adapters, and/or controllers. The computer system 600 can also include one or more network interface(s) 1906, one or more input/output (IO) interface(s) 1908 that can include one or more interface components, and one or more storage device(s) 1910.

The network interface(s) 1906 can enable the computer system 1900 to communicate with remote devices, e.g., motors coupled to the drive system drive discs 220, 240, 260 and/or the generator 300. Such communication can occur over dedicated transmission lines, over a network, and the like. As an example, a network can be any combination of remote connection interfaces, Ethernet adapters, and/or other local area network (LAN) adapters. The IO interface(s) 1908 can include one or more interface components to connect the computer system 1900 with other electronic equipment, such as the sensors located on the motor(s). For non-limiting example, the IO interface(s) 1908 can include high speed data ports, such as universal serial bus (USB) ports, 1394 ports, Wi-Fi, Bluetooth, etc. Additionally, the computer system 1900 can be accessible to a human user, and thus the IO interface(s) 1908 can include displays, speakers, keyboards, pointing devices, and/or various other video, audio, or alphanumeric interfaces. The storage device (s) 1910 can include any conventional medium for storing data in a non-volatile and/or non-transient manner. The storage device(s) 1910 can thus hold data and/or instructions in a persistent state, i.e., the value(s) are retained despite interruption of power to the computer system 1900. The storage device(s) 1910 can include one or more hard disk drives, flash drives, USB drives, optical drives, various media cards, diskettes, compact discs, and/or any combination thereof and can be directly connected to the computer system 1900 or remotely connected thereto, such as over a network. In an exemplary embodiment, the storage device(s) 1910 can include a tangible or non-transitory computer readable medium configured to store data, e.g., a hard disk drive, a flash drive, a USB drive, an optical drive, a media card, a diskette, a compact disc, etc.

The elements illustrated in FIG. 19 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1900 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1900 can also include a web server for generating and/or delivering the web pages to client computer systems.

In an exemplary embodiment, the computer system 1900 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

B. Tissue Treatments Using Ultrasonic Surgical Instruments

Figure 20A:
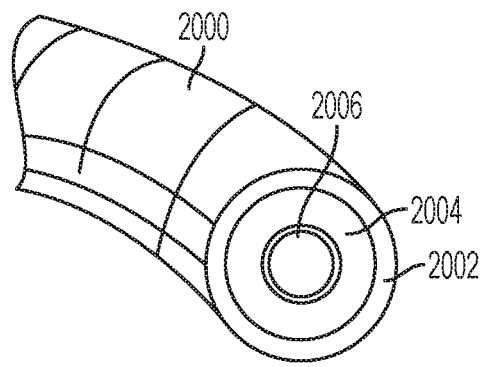
FIG. 20A is a schematic illustration of a vessel such as an artery.
Figure 20B:
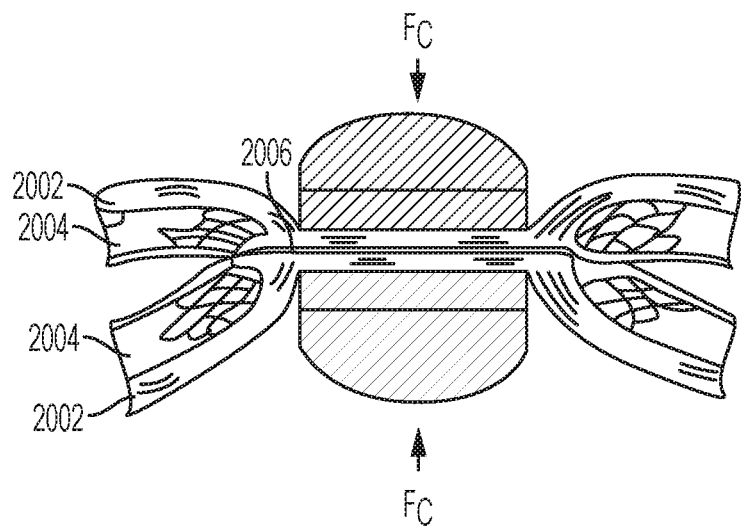
FIG. 20B is a schematic illustration of the vessel of FIG. 20A after compression by an end effector of a surgical instrument.
Figure 20C:
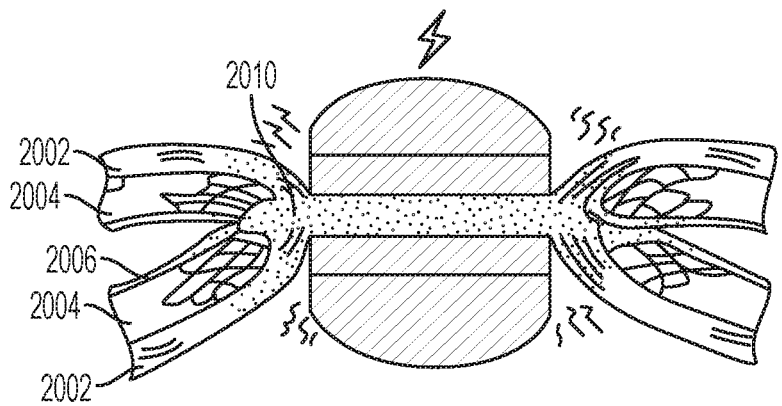
FIG. 20C is a schematic illustration of the vessel of FIG. 20B during application of ultrasonic energy to cut the vessel.

As noted above, cutting, coagulation, and sealing of tissue using ultrasonic surgical instruments can be accomplished by a combination of pressure from an ultrasonic blade and ultrasonic vibrations of the ultrasonic blade. This process is schematically illustrated in FIGS. 20A-20C. FIG. 20A shows a blood vessel 2000 in cross-section before contact with an ultrasonic surgical instrument. As shown, the blood vessel 2000 can include an outer layer or adventita 2002, a middle layer or media 2004, and an inner layer or intima 2006. When a sufficient compressive or clamping force $F_c$ is applied to the blood vessel 2000, the middle layer 2004 can break apart, leaving only the outer layer 2002 and inner layer 2006 intact. Subsequently, while maintaining the clamping force $F_c$, ultrasonic energy can be applied to an ultrasonic blade of the ultrasonic surgical instrument, as further shown in FIG. 20C. Vibration of the ultrasonic blade can transfer mechanical energy to the blood vessel 2000, breaking hydrogen bonds and producing heat by friction. This frictional heat can denature proteins within the blood vessel 2000, forming a coagulum 2010 that can seal the blood vessel 2000. Once the blood vessel 2000 is sealed, vibration of the ultrasonic blade and can also be employed to cut the blood vessel 2000.

a. Tissue Treatment Protocols Inhibiting Tissue Sticking

In general, as discussed above, the end effector 150 can be configured to clamp, cut, and coagulate tissue. As an example, the end effector 150 can be configured to receive tissue between the clamp arm 152 and the ultrasonic blade 160, where the distance separating the clamp arm 152 from the ultrasonic blade 160 in an open position can be dimensioned to receive tissue of predetermined thickness. Movement of the clamp arm 152 towards the ultrasonic blade 160 can apply a clamping force to tissue disposed between the clamp arm 152 and the ultrasonic blade 160, while transmission of ultrasonic energy to the ultrasonic blade 160 (e.g., mechanical vibrations at ultrasonic frequencies) can coagulate and cut the tissue.

One problem encountered during the use of ultrasonic surgical instruments for cutting tissue is sticking of tissue to the ultrasonic blade. When sticking occurs, removal of the ultrasonic blade can cause tissue tearing and additional bleeding. Accordingly, embodiments of the control system 39 can be configured to provide treatment protocols that reduce or eliminate the likelihood of tissue sticking to ultrasonic blades. As discussed in greater detail below, the clamping force can be varied between predetermined levels before or during transmission of ultrasonic energy to the ultrasonic blade 160 to inhibit tissue sticking to the ultrasonic blade 160.

Figure 21:
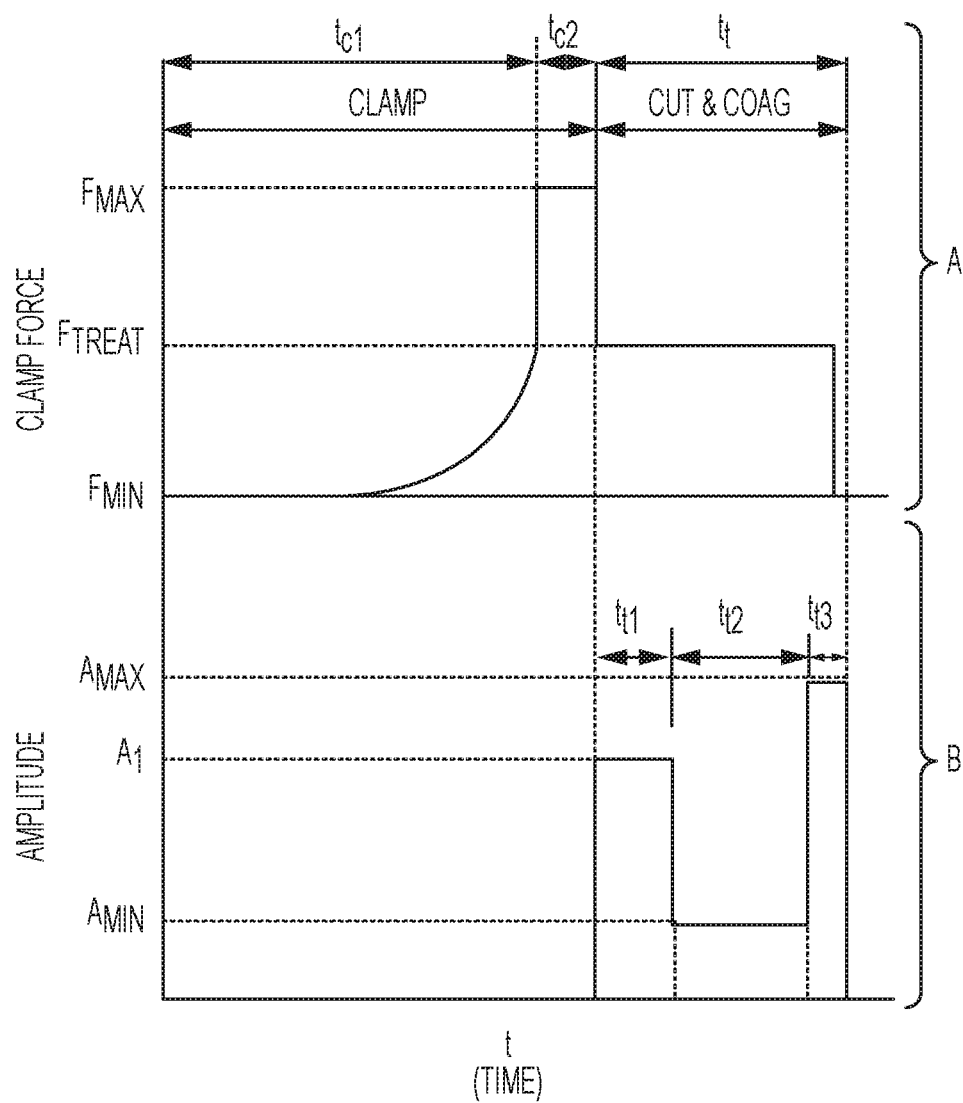
FIG. 21 is a plot of exemplary embodiments of a treatment protocol implemented by the control system of FIG. 19 that is suitable for use with the end effector of FIG. 6 for inhibiting sticking of tissue to the ultrasonic blade; (Part A) clamping forces applied to tissue by the clamping element as a function of time; (Part B) ultrasonic amplitude delivered to the ultrasonic blade as a function of time.

FIG. 21 illustrates one exemplary embodiment of a tissue treatment protocol for clamping, coagulating, and cutting tissue with an ultrasonic surgical instrument (e.g., surgical instrument 100) that can inhibit tissue sticking to the ultrasonic surgical instrument 100. Part A of FIG. 21 presents clamping forces applied to tissue by the clamp arm 152 as a function of time. Part B of FIG. 21 presents corresponding amplitudes of ultrasonic vibrations delivered to the ultrasonic blade 160 as a function of time. As discussed below, the control system 39 can implement the treatment protocol such that a clamping force applied to tissue can be varied before transmission of ultrasonic vibrations to the ultrasonic blade 160 in three control modes.

In a first control mode, a gradually increasing clamping force is applied to tissue disposed between the clamp arm 152 and the ultrasonic blade 160 prior to transmitting ultrasonic energy to the ultrasonic blade 160. The clamping force is increased from a minimum clamping force $F_{min}$ to a maximum clamping force $F_{max}$ over a predetermined first clamping time $t_{c1}$ while the clamp arm is under displacement control. In an embodiment, the minimum clamping force $F_{min}$ can be about zero, the maximum clamping force $F_{max}$ can be selected from the range from about 5 lbs. to about 7 lbs., and the first clamping time $t_{c1}$ can be selected from the range from about 1 sec. to about 4 sec.

A second control mode can occur immediately after the first control mode and it occurs before transmission of ultrasonic vibrations to the ultrasonic blade 160. As shown, the second control mode includes maintaining the maximum clamping force $F_{max}$ for a predetermined second clamping time $t_{c2}$ while the clamp arm is under displacement control. The second clamping time $t_{c2}$ can be selected from the range from about 0.75 sec. to about 2 sec. (e.g., about 1 sec). The relatively high maximum clamping force $F_{max}$ can ensure that the middle layer of tissue (e.g., 2004) separates, as illustrated in FIG. 20B.

A third control mode can occur immediately after the second control mode and it can occur during transmission of ultrasonic vibrations to the ultrasonic blade 160. As shown, the third control mode includes reducing the clamping force to a treatment clamping force $F_{treat}$ that is between the minimum clamping force $F_{min}$ and the maximum clamping force $F_{max}$ (e.g., about half of the maximum clamping force $F_{max}$). The third control mode also includes maintaining the treatment clamping force $F_{treat}$ for a predetermined treatment time $t_t$. In an embodiment, the treatment clamping force $F_{treat}$ can be selected from the range from about 3 lbs. to about 5.5 lbs. and the treatment time $t_t$ can be about 18 sec. The reduction in clamping force from the maximum clamping force $F_{max}$ to the treatment clamping force $F_{treat}$ and maintenance of the treatment clamping force in load control over the duration of the treatment time $t_t$ can ensure that the clamping force is sufficient to ensure good contact between the ultrasonic blade 160 and the tissue without applying a relatively high clamping force that can tend to cause tissue sticking to the ultrasonic blade 160.

During the treatment time $t_t$, a peak amplitude of ultrasonic vibrations transmitted to the ultrasonic blade 160 can be varied between a minimum ultrasonic amplitude $A_{min}$ and a maximum ultrasonic amplitude $A_{max}$. As shown, an ultrasonic amplitude $A_1$, between the minimum ultrasonic amplitude $A_{min}$ and the maximum ultrasonic amplitude $A_{max}$, can be transmitted to the ultrasonic blade 160 immediately after the second clamping time $t_{c2}$ for a first portion $t_{t1}$ of the treatment time $t_t$. The minimum ultrasonic amplitude $A_{min}$ can be transmitted to the ultrasonic blade 160 immediately after the first portion $t_{t1}$ of the treatment time $t_t$ for a second portion $t_{t2}$ of the treatment time $t_t$. In an embodiment, the minimum ultrasonic amplitude $A_{min}$ can be about 50% of $A_{max}$, and the ultrasonic amplitude $A_1$ can be selected from the range from about 80% to about 100% of $A_{max}$. In an embodiment, $A_{max}$ can be about 77 μm. In an embodiment, $t_{t1}$ can be about 1 sec. and $t_{t2}$ can be about 16 sec.

The first and second portions $t_{t1}$ and $t_{t2}$ of the treatment time $t_t$ can extend over the majority of the treatment time $t_t$. The intermediate ultrasonic amplitude $A_1$ and the first portion $t_{t1}$ of the treatment time $t_t$ can be configured to rapidly heat the tissue to a temperature sufficient to form the coagulum 2010 and begin ultrasonic cutting of the coagulum 2010. The minimum ultrasonic amplitude $A_{min}$ and the second portion $t_{t2}$ of the treatment time $t_t$ can be configured to ensure that the extent of the coagulum 2010 is sufficient and continue cutting the tissue.

The maximum amplitude $A_{max}$ can be transmitted to the ultrasonic blade 160 immediately after the second portion $t_{t2}$ of the treatment time $t_t$ for a third portion $t_{t3}$ of the treatment time $t_t$. The maximum ultrasonic amplitude $A_{max}$ and the third portion $t_{t3}$ of the treatment time $t_t$ can be configured to ensure that the tissue is completely cut. In an embodiment, $t_{t3}$ can be about 1 sec.

Figure 22:
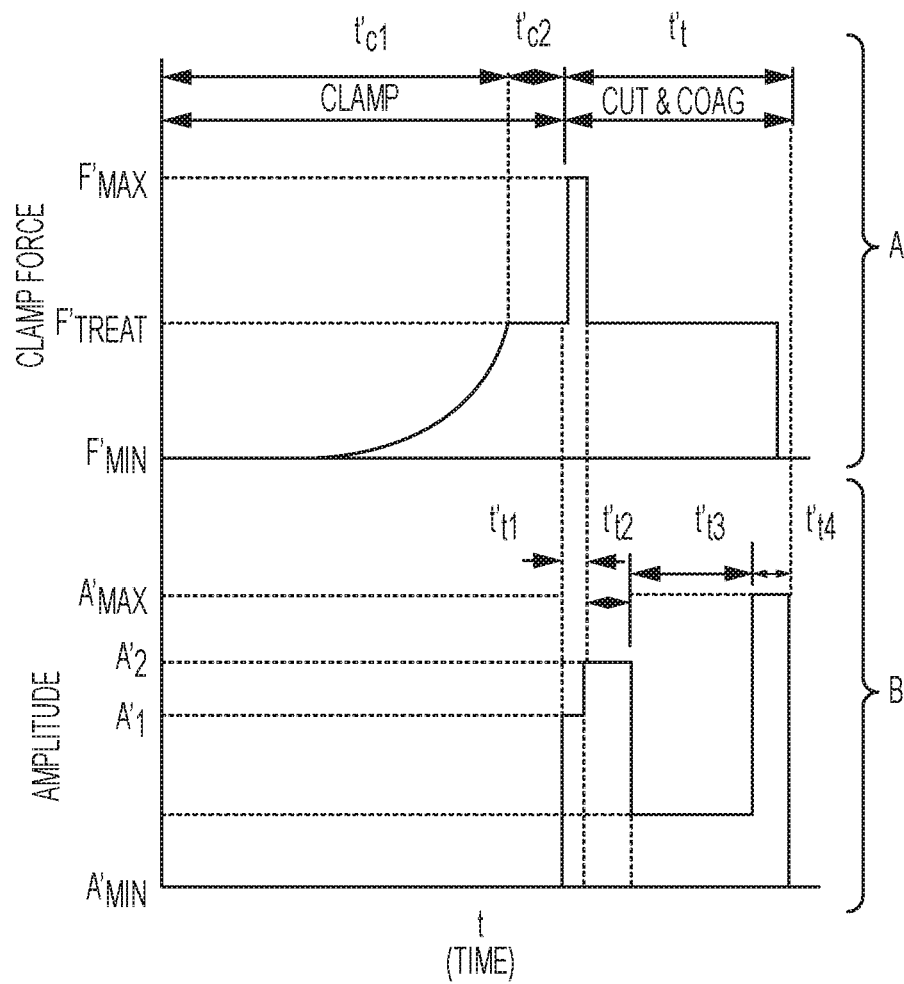
FIG. 22 is a plot of another exemplary embodiment of control of the end effector of FIG. 6 by the control system of FIG. 19 illustrating clamping forces (Part A) and ultrasonic energy amplitude delivered to the ultrasonic blade (Part B) as a function of time.

FIG. 22 illustrates another exemplary embodiment of a treatment protocol for inhibiting tissue sticking to an ultrasonic surgical instrument. Part A of FIG. 22 presents clamping forces applied to tissue by the clamp arm 152 as a function of time. Part B of FIG. 22 presents corresponding amplitudes of ultrasonic vibrations delivered to the ultrasonic blade 160 as a function of time. As discussed below, the control system 39 can implement the treatment protocol such that a clamping force applied to tissue is varied during transmission of ultrasonic vibrations to the ultrasonic blade 160 in four control modes.

In a first control mode, a gradually increasing clamping force is applied to tissue disposed between the clamp arm 152 and the ultrasonic blade 160 prior to transmitting ultrasonic energy to the ultrasonic blade 160. The clamping force can be increased from a minimum clamping force $F'_{min}$ to a treatment clamping force $F'_{treat}$ over a predetermined first clamping time $t'_{c1}$ while the clamp arm is under displacement control. The treatment clamping force $F'_{treat}$ can be a clamping force that is between the minimum clamping force $F'_{min}$ and a maximum clamping force $F'_{max}$. In an embodiment, the minimum clamping force $F'_{min}$ can be about 2.5 lbs., the treatment clamping force $F'_{treat}$ can be selected from the range from about 3 lbs. to about 3.5 lbs., and the maximum clamping force $F'_{max}$ can be about 5.5 lbs.

A second control mode can occur immediately after the first control mode and it can occur before transmission of ultrasonic vibrations to the ultrasonic blade 160. As shown, the second control mode includes maintaining the treatment clamping force $F'_{treat}$ for a predetermined second clamping time $t'_{c2}$ while the clamp arm is under displacement control. The treatment clamping force $F'_{treat}$ can be configured to separate the middle layer of tissue (e.g., 2004), as illustrated in FIG. 20B.

A third control mode can occur immediately after the second control mode and it can occur during a portion of a treatment time $t'_t$ during which ultrasonic vibrations are transmitted to the ultrasonic blade 160. As shown, the third control mode includes increasing the clamping force from the treatment clamping force $F'_{treat}$ to the maximum clamping force $F_{max}$ and maintaining the maximum clamping force $F'_{max}$ for a predetermined first portion $t'_{t1}$ of the treatment time $t'_t$ under load control. In an embodiment, the treatment time $t'_{t1}$ can be about 0.5 sec.).

Concurrently, an ultrasonic vibration amplitude $A'_1$ between a minimum ultrasonic vibration amplitude $A'_{min}$ and a maximum ultrasonic vibration amplitude $A'_{max}$ can be transmitted to the ultrasonic blade 160. The increase in clamping force from the treatment clamping force $F_{treat}$ the maximum clamping force $F_{max}$ and maintenance of the maximum clamping force $F_{max}$ in load control over the first portion of the treatment time $t'_{t1}$ can ensure that the clamping force separates the middle layer 2004. The relatively moderate ultrasonic vibration amplitude can be selected to provide coagulation of tissue while also reducing the likelihood of tissue sticking while the clamping force is high.

A fourth control mode can occur immediately after the third control mode and it can also occur during a portion of a treatment time $t'_t$ during which ultrasonic vibrations are transmitted to the ultrasonic blade 160. As shown, the third control mode includes decreasing the clamping force from the maximum clamping force $F'_{max}$ to the treatment clamping force $F'_{treat}$ and maintaining the treatment clamping force $F'_{treat}$ for a predetermined second portion $t'_{t2}$, third portion $t'_{t3}$, and fourth portion $t'_{t4}$ of the treatment time $t'_t$ under load control. In an embodiment, $t'_{t2}$ can be about 0.75 sec., $t'_{t3}$ can be about 16 sec., and $t'_{t4}$ can be about 1 sec.

Concurrently, the amplitude of ultrasonic vibrations transmitted to the ultrasonic blade 160 can be varied. As an example, an ultrasonic vibration amplitude $A'_2$, greater than the ultrasonic vibration amplitude $A'_1$, can be transmitted to the ultrasonic blade 160 during the second portion $t'_{t2}$ of the treatment time $t'_t$. Subsequently, an ultrasonic vibration amplitude $A'_3$ can be transmitted to the ultrasonic blade 160 during the third portion $t'_{t3}$ of the treatment time $t'_t$, followed by the maximum ultrasonic vibration amplitude $A'_{max}$ during the fourth portion $t'_{t4}$ of the treatment time $t'_t$. In an embodiment, the minimum ultrasonic amplitude $A'_{min}$ can be about 50% of $A'_{max}$, the ultrasonic amplitude $A'_1$ can be about 80% of $A'_{max}$, the ultrasonic amplitude $A'_2$ can be selected from the range from about 85% of $A'_{max}$ to about 90% of $A'_{max}$. In an embodiment, the maximum ultrasonic amplitude $A'_{max}$ can be about 77 µm.

The increase in ultrasonic vibration amplitude from $A'_1$ to $A'_2$ can be configured to ensure that coagulation of the tissue extends a sufficient distance within the tissue to span the region to be separated. The minimum ultrasonic vibration amplitude $A'_{min}$ can be large enough to provide tissue cutting. Thus, the decrease in ultrasonic vibration amplitude from $A'_2$ to $A'_{min}$ can be configured to ensure that tissue sticking does not occur while the ultrasonic blade 160 cuts the tissue. The increase in ultrasonic vibration amplitude from $A'_{min}$ to $A'_{max}$ can be configured to ensure that the tissue is severed by the end of the treatment $t'_t$ time.

b. Tissue Treatment Protocols for Inhibiting Clamp Pad Damage

As noted above, in robotic surgery, a user 12, 12' can have less direct haptic feedback compared to traditional manually-powered surgical instruments. This lack of haptic feedback can result in uncertainty whether tissue transection has completed. Thus, a user 12, 12' can take time to rotate the surgical instrument, while clamped and ultrasonic vibrations are transmitted to the ultrasonic blade 160, to visualize and verify the seal formed by the surgical instrument 100. However, in the circumstance where tissue transection is completed and the clamp arm 152 is fully closed, the clamp pad 154 can contact the vibrating ultrasonic blade 160. If left in contact with the clamp pad 154 for an extended duration, the ultrasonic blade 160 can cut and/or burn the clamp pad 154. Depending upon the severity of damage, it can be necessary to replace the clamp pad 154, incurring time and expense. Accordingly, embodiments of the control system 39 can be configured to inhibit damage to the clamp pad 154 during use of the ultrasonic surgical instrument 100.

As an example, the control system 39 can monitor the clamp force exerted on the tissue (e.g., by sensing the torque applied to motors coupled to the drive system drive discs 220, 240, 260). When cutting and sealing of tissue is complete, the control system 39 can cause an audio and/or visual indication (e.g., an audible tone) to be provided to signal a user 12, 12' that transection is complete and to relax pressure on the ultrasonic blade. As an example, the controller 30 can include one or more audio and/or video components in communication with the control system 39 and configured to provide the audio and/or visual indication (e.g., display 34).

Under the circumstance where the ultrasonic blade 160 is left in contact with the clamp pad 154 for greater than a predetermined time after the audio and/or video indication is provided, the control system 39 can be configured to further adjust at least one of the clamping force and the amplitude of the ultrasonic vibrations transmitted to the ultrasonic blade 160. As an example, when the predetermined time is exceeded, the control system 39 can command the clamp arm 152 lower the clamping force. This can allow a user to continue to transmit ultrasonic vibrations to the ultrasonic blade 160 with a lighter clamping force, improving the feel and/or responsiveness of the user's experience without damaging the clamp pad 154.

c. Tissue Treatment Protocols for Applying Tension to Complete Transection

It can be beneficial when employing ultrasonic surgical instruments, such as surgical instrument 22, to apply tension to complete tissue transection. This tension can accelerate completion of tissue transection, limit heat build-up in the ultrasonic surgical instrument 100, and inhibit damage to the clamp pad (e.g., pad burn) due to relatively quick completion of tissue transection. However, it can be difficult to apply slight tension using robotic surgical instruments, as they can remain perfectly stable. Accordingly, embodiments of the control system 39 can be configured to apply sufficient tension to tissue near the end of tissue transection.

As an example, the control system 39 is configured to monitor the clamping force applied to tissue by the end effector 150 when operating under displacement control. When the tissue nears complete transection, the applied force increases as the clamp pad 154 begins to contact the ultrasonic blade 160. After sensing that the clamping force reaches a predetermined clamping threshold, the control system 39 causes the ultrasonic surgical instrument 100 to apply tension by slight movements away from the tissue (e.g., upwards and backwards). Alternatively or additionally, the control system 39 can reduce the clamping pressure to prevent pad burn and heat accumulation, as discussed above. Either or both of these operations can be performed immediately upon sensing that the clamping force reaches the predetermined clamping threshold or after a predetermined time delay. Furthermore, either or both of these operations can be configurable by the user 12, 12' using the control system 39 and can be activated, turned off, or modified (e.g., the predetermined clamping threshold, the predetermined delay, etc.).

d. Tissue Treatment Protocols for Maintaining Constant Ultrasonic Amplitude

As discussed above, embodiments of the ultrasonic surgical instrument 100 can be configured to allow articulation of the end effector 150, such as bending, using the articulation section 130. As an example, an articulation angle of the end effector 150 with respect to a longitudinal axis of the ultrasonic surgical instrument 100 can be controlled by rotation of the drive shaft 244. However, as the articulation angle increases, ultrasonic vibrations transmitted to the ultrasonic blade 160 can become attenuated. Accordingly, embodiments of the control system 39 are configured to compensate for this attenuation.

In one aspect, the control system 39 is configured to measure the articulation angle of the end effector 150. As an example, the control system 39 can measure upon rotation of the drive shaft 244 in order to measure the articulation angle of the end effector 150. In another aspect, the control system 39 can receive input from a user 12, 12' employing the controller 30 to command articulation of the end effector 150. In response, the control system 39 can be configured to scale the commanded ultrasonic vibration amplitude based upon the measured articulation angle of the end effector 150 in order to compensate for ultrasonic attenuation. The control system 39 can perform this scaling during articulation of the end effector 150.

Figure 23:
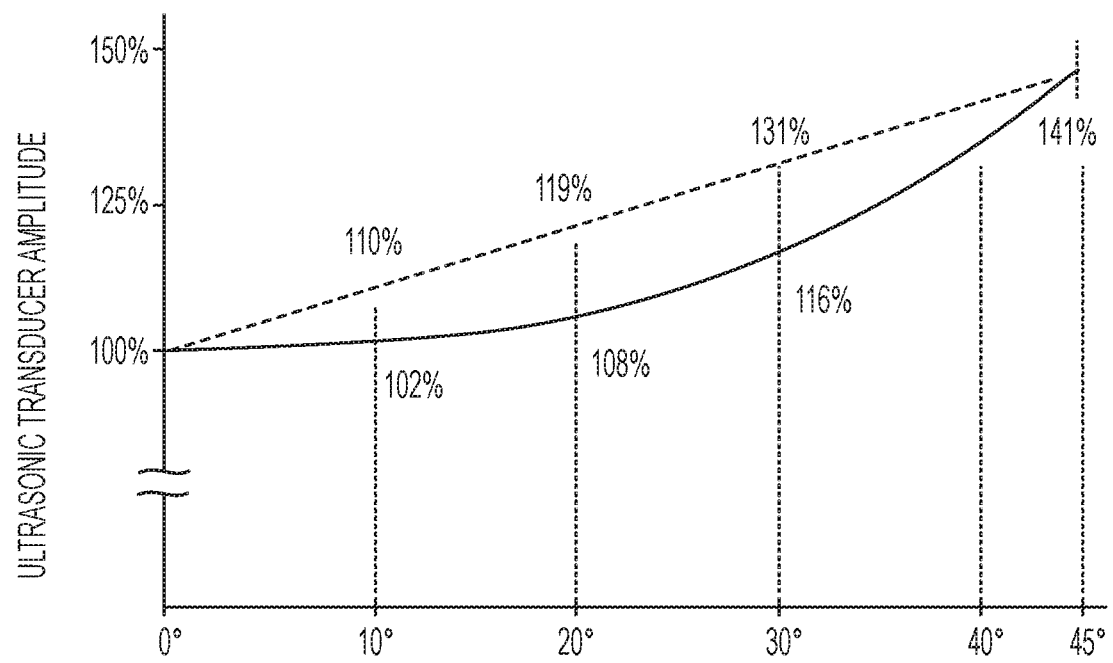
FIG. 23 is a plot of another exemplary embodiment of control of the end effector of FIG. 6 by the control system of FIG. 19 illustrating relative ultrasonic energy amplitude that can be applied to an articulating end effector as a function of articulation angle.

One exemplary scaling relationship between ultrasonic vibration amplitude and articulation angle of the end effector 150 is illustrated in the plot of FIG. 23. As shown, ultrasonic vibration amplitude generally increases as the end effector articulation increases from a minimum articulation angle (e.g., about 0°) to a maximum articulation angle (e.g., about 45°), reflecting a greater degree of ultrasonic attenuation at high articulation angles as compared to low articulation angles. In certain embodiments, a rate of change of the ultrasonic amplitude can increase with articulation angle. As an example, the ultrasonic vibration amplitude can be about 100% at about 0° and the ultrasonic vibration amplitude can be about 141% at an articulation angle of about 45°. In alternative embodiments, the rate of change of the ultrasonic amplitude can be approximately constant (dashed line). That is, the ultrasonic amplitude can be directly proportional to the ultrasonic amplitude.

It should be understood that the relationship between the ultrasonic vibration amplitude and the articulation angle of the end effector 150 can adopt other forms, depending upon the configuration of the ultrasonic surgical instrument 100. The form of this relationship can be determined empirically, theoretically, or combinations thereof.

C. Combination Ultrasonic and Radiofrequency Surgical Instruments

In further embodiments, the surgical instrument 100 can be configured to provide tissue coagulation through application of radiofrequency (RF) energy alone or in combination with ultrasonic vibrations. RF energy is a form of electrical energy that can be in the frequency range of about 200 kilohertz (kHz) to about 1 megahertz (MHz). As discussed in greater detail below, the instrument 100 can transmit low frequency RF energy through tissue, which can cause ionic agitation, or friction, in effect resistive heating, thereby increasing the temperature of the tissue. Because a sharp boundary is often created between the affected tissue and the surrounding tissue, a user 12, 12' can operate with a high level of precision and control, without sacrificing un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen that can shrink when subjected to heat.

In order to facilitate delivery of RF energy to tissue, the generator 300 includes a power source and control module that is configured to provide RF energy to one or more electrodes mounted to the end effector 150. Examples of generators configured to drive the ultrasonic transducer 120 and RF electrodes are discussed in greater detail in U.S. Patent Publication No. 2017/0202609, entitled "Modular Battery Powered Hand-Held Surgical Instrument With Curved End Effectors Having Asymmetric Engagement Between Jaw and Blade," the entirety of which is incorporated by reference.

Figure 24A:
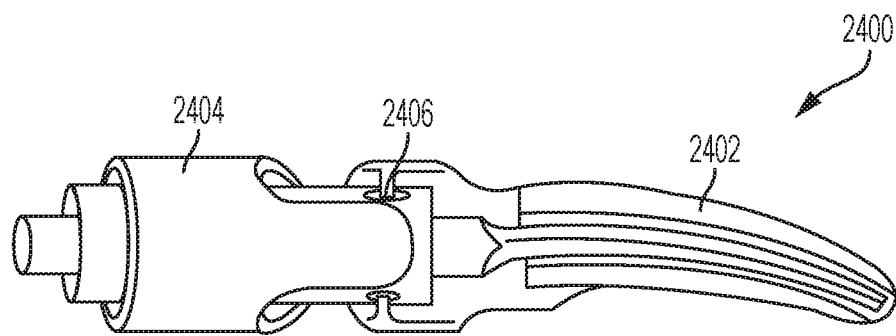
FIG. 24A is a side view of another exemplary embodiment of an end effector including a clamping element, an ultrasonic blade, and one or more radiofrequency (RF) electrodes.

FIG. 24A illustrates a side view of an exemplary embodiment of an end effector 2400 configured to deliver ultrasonic vibrations and RF energy to tissue. The end effector 2400 includes a jaw member 2402 and a shaft 2404. The jaw member 2402 can pivot about pivot point 2406 and define a pivot angle. In certain aspects, the pivot point 2406 can be similar to the pair of arms 156 and the pin 170 discussed above.

Figure 24B:
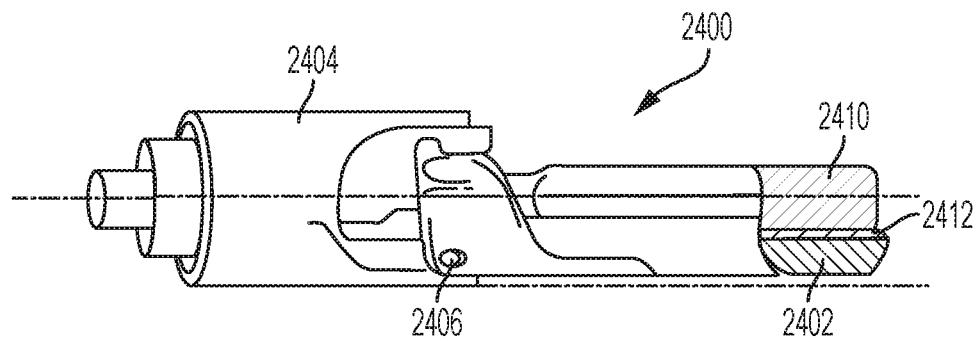
FIG. 24B is another side view of the end effector of FIG. 24A.

FIG. 24B illustrates another side view of the end effector 2400 of FIG. 24A with a partial cut away view to expose the underlying structure of the jaw member 2402 and an ultrasonic blade 2410. The ultrasonic blade 2410 can be the same as ultrasonic blade 160 discussed above. An electrode 2412 is fixedly mounted to the jaw member 2402. The electrode 2412 can be electrically coupled to an RF drive circuit contained within a portion of the generator 300 configured to deliver RF energy to the electrode 2412 (e.g., RF drive circuit 702).

Figure 24C:
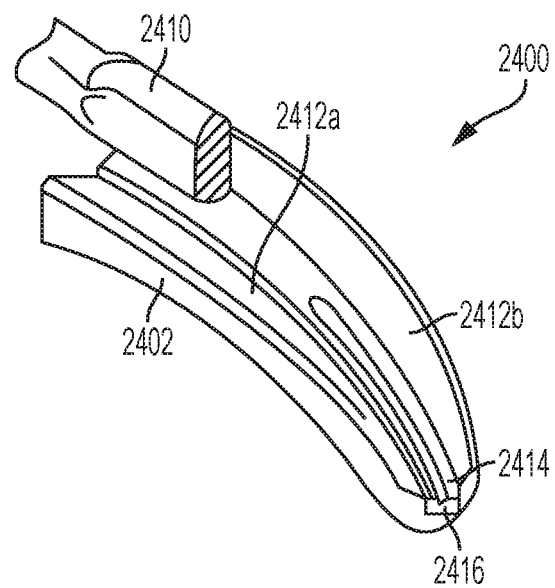
FIG. 24C is a perspective sectional view of the end effector of FIGS. 24A-24B.

The electrode 2412 is configured to apply RF energy to tissue located between the jaw member 2402 and the ultrasonic blade 2410. FIG. 24C is partial sectional view of the end effector 2400 exposing the ultrasonic blade 2410 and an embodiment of the electrode 2412 including right and left electrodes 2412a and 2412b, respectively. The jaw member 2402 and the ultrasonic blade 2410 can be wider at a proximal end and narrower at a distal end. Also, the jaw member 2402 and the ultrasonic blade 2410 can define more curvature at a distal end relative to the proximal end. A soft, electrically insulating pad 2414 can be disposed between the first and second electrodes 2412a, 2412b. In one aspect, the electrically insulating pad 2414 can be located adjacent to a high density polymeric pad 2416 to prevent the ultrasonic blade 2410 from shorting the electrodes 2412a, 2412b. In one aspect, the pads 2414, 2416 can be formed from polytetrafluoroethylene (PTFE) polymers and copolymers. Heat generated by the current flowing through the tissue can form hemostatic seals within the tissue and/or between tissues and thus may be particularly useful for sealing blood vessels, for example.

In an embodiment, the end effector 2400 can be configured for bipolar or monopolar operation. During bipolar operation, current can be introduced into tissue by the electrode 2412 and returned from the tissue by the ultrasonic blade 2410. During monopolar operation, current can be introduced into the tissue by the electrode 2412 and returned through a return electrode (e.g., a ground pad) separately located on a patient's body.

The RF energy can be in a frequency range described in EN 60601-2-2:2009+A11:2011, Definition 201.3.218—HIGH FREQUENCY, the entirety of which is incorporated by reference. For example, the frequency in monopolar RF applications can be typically restricted to less than about 5 MHz. However, in bipolar RF applications, the frequency can adopt any desired value. Frequencies above 200 kHz can be used for monopolar applications in order to avoid the unwanted stimulation of nerves and muscles that can result from the use of low frequency current. Lower frequencies can be used for bipolar applications if a risk analysis shows the possibility of neuromuscular stimulation has been mitigated to an acceptable level. In general, frequencies above 5 MHz can be avoided in order to minimize problems associated with high frequency leakage currents. Higher frequencies can, however, be used in the case of bipolar applications. In certain embodiments, 10 mA can be a lower threshold of thermal effects on tissue. Further discussion of embodiments of the generator 300 and the end effector 2400 can be found in U.S. Patent Publication No. 2017/0202609, entitled "Modular Battery Powered Hand-Held Surgical Instrument With Curved End Effectors Having Asymmetric Engagement Between Jaw and Blade," the entirety of which is incorporated by reference.

a. Treatment Protocols Utilizing Motor Torque for Maintaining Treatment Force and Selective Delivery of RF Energy to Tissue When using electrically-powered surgical instruments for delivery of RF energy to tissue, it can be desirable to inhibit delivery of RF energy to tissue before the clamping force applied to the tissue reaches a predetermined range. When the clamping force is within this range and RF energy is subsequently delivered to the tissue, the outer layer 2002 and inner layer 2006 can be properly sealed even while the tissue thickness dynamically changes (e.g., decreases).

In non-powered surgical instruments, a large wave spring can employed to compensate for variations in tissue thickness to apply the clamping force within the predetermined range. However, in powered surgical instruments, where actuation of the end effector is driven by motors, this spring can be very difficult to control. Accordingly, embodiments of present disclosure can provide powered surgical instruments in which the wave spring is omitted. The control system 39 can be configured to implement treatment protocols that achieve clamping forces within a predetermined range by selectively controlling closure of an end effector under either displacement or load control. In this manner, a user can employ powered surgical instruments for relatively delicate work such as spread dissection and tissue manipulation.

Figure 25:
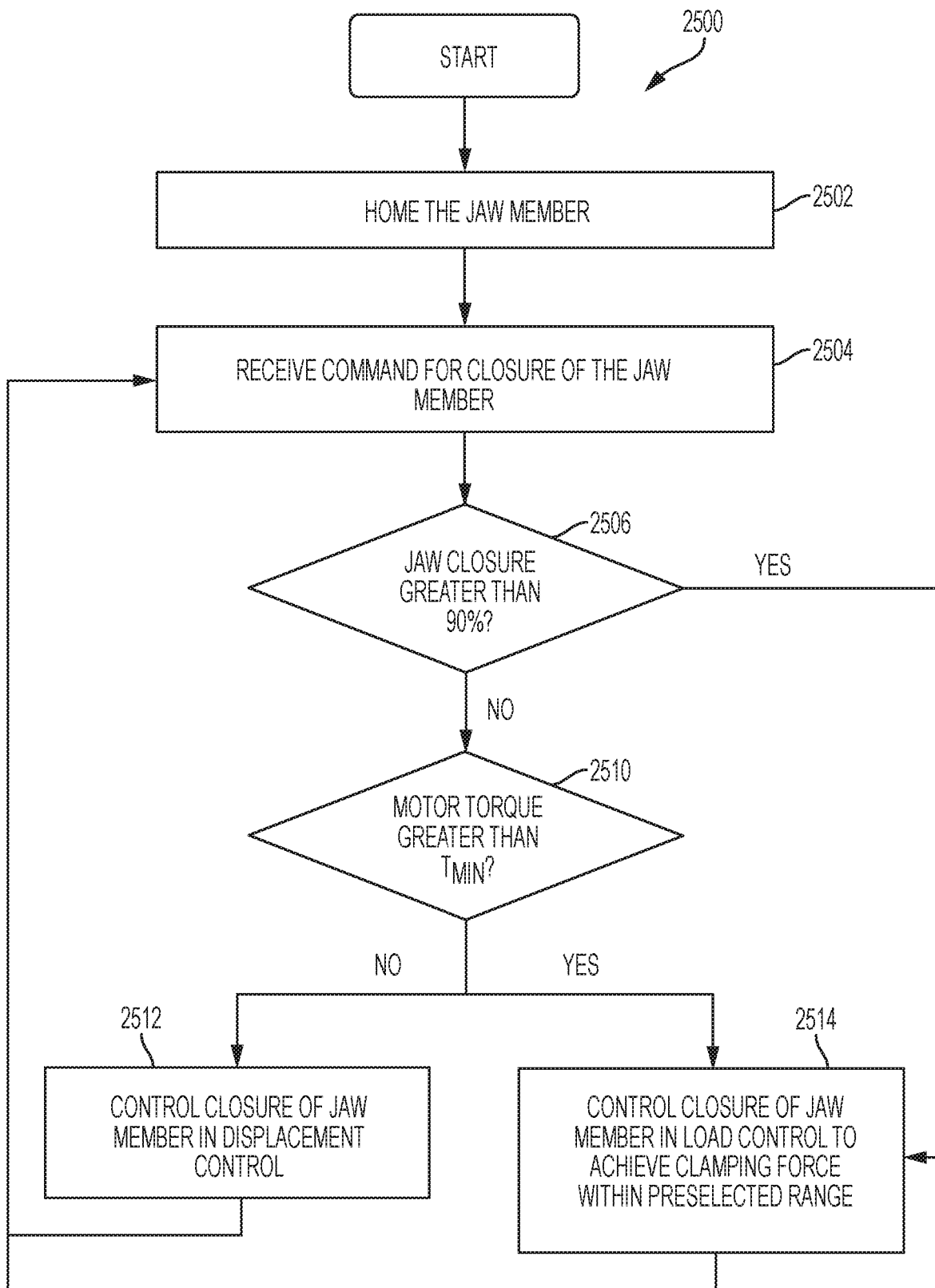
FIG. 25 is a flow diagram illustrating an exemplary embodiment of a method for fine control of closure of end effector of FIGS. 24A-24C implemented by the control system of FIG. 19.

FIG. 25 is a flow diagram illustrating an exemplary embodiment of a method 2500 including operations 2502-2514 for fine control of closure of an end effector to achieve a clamping force within a predetermined range using motors, instead of, for example, a wave spring. Embodiments of the method 2500 are discussed in detail below in the context of the robotic surgical system 10 employing an ultrasonic surgical instrument 100 using the end effector 2400. However, as noted above, the disclosed embodiments can also be utilized with hand-held powered surgical instruments as well. Additional embodiments of the method 2500 can omit one or more of the operations illustrated in FIG. 25 or add additional operations and the operations can be performed in a different order than those illustrated and described without limit.

In operation 2502, the user 12, 12' can employ the controller 30 to command the jaw member 2402 to adopt the home position. In general, the jaw member 2402 is configured to move between an open position and a closed position. In the open position, a degree of closure of the jaw member 2402 can be approximately 0%, while in the closed positon the degree of closure of the jaw member 2402 can be approximately 100%. For ease of reference herein, the open position will be assumed as the home position. However, it will be understood that the open position can be any predefined location between and including the open position and the closed position.

In operation 2504, the user 12, 12' can employ the controller 30 to command the jaw member 2402 to adopt a selected degree of closure.

In general, movement of the jaw member 2402 under position control uses a received position command as a target set point without consideration of the force applied to the tissue as a result of such a movement. Moving the jaw in this manner can be advantageous because when the tissue is relatively thin because a low degree of closure can result in application of clamping force less than a predetermined minimum clamping force $F_{min}$ (e.g., a clamping force lower than desired for delivery of RF energy to the tissue). However, moving the jaw in this manner is not advantageous if the tissue is relatively thick because even a low degree of closure can result in application of a clamping force higher exceeding a predetermined maximum force $F_{max}$ (e.g., a clamping force greater than desired for delivery of RF energy to the tissue). $F_{min}$ and $F_{max}$ therefore represent a desired range of clamping force applied to the tissue for delivery of RF energy to the tissue.

In operations 2506 and 2510, the control system 39 determines whether the received command is executed in position control. As shown, in operation 2506, the control system 39 determines if the degree of closure is less than a threshold closure (e.g., about 90%). If so, the method 2500 moves to operation 2510. In operation 2510, the control system 39 determines if a torque of a motor controlling displacement of the jaw member 2402 is greater than a threshold torque $\tau_{min}$. In this context, torque can be used to approximate a measure clamping force. As an example, an amount of torque applied by a motor controlling displacement of the jaw member 2402 (e.g., a motor operable to rotate the drive shaft 264) can be correlated to the clamping force applied to the tissue by the jaw member 2402. Thus, $\tau_{min}$ can be correlated to $F_{min}$. This torque check can ensure that, even if the degree of closure is relatively low, the clamping does not exceed $F_{max}$. Such a circumstance can arise if the tissue is relatively thick and the jaw member 2402 can contact the tissue with relatively little closure. If the motor torque measured by the control system is less than the threshold torque $\tau_{min}$, representing application of a relatively low clamping force to the tissue, the method 2500 can move to operation 2512, where closure of the jaw member 2402 is controlled under position control.

Alternatively, if either the degree of jaw closure is greater than the threshold torque or the motor torque is greater than the threshold torque $\tau_{min}$, the method 2500 can move to operation 2514. In operation 2514, control of the jaw member 2402 is performed in load control to achieve a clamping force at a preselected level from the range between about $F_{min}$ and $F_{max}$. In load control, the control system 39 employs measurements of the motor torque to control the clamping force at preselected levels from the range between about $F_{min}$ and $F_{max}$, corresponding to $\tau_{min}$ and $\tau_{max}$. As an example, current drawn by the motor operable to rotate the drive shaft 264 can be used to measure its motor torque.

Figure 26:
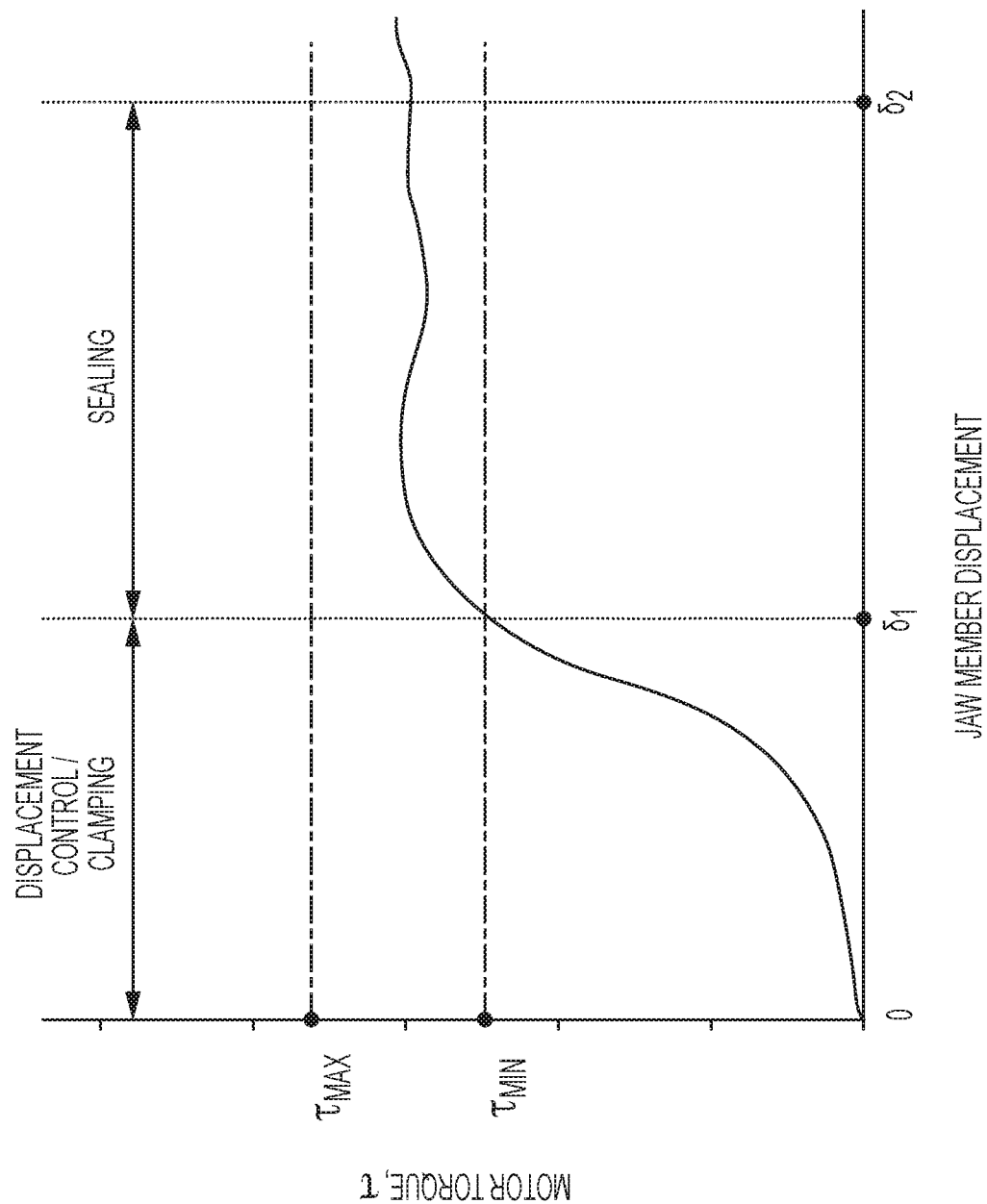
FIG. 26 is a plot of an exemplary embodiment of motor torque as a function of jaw member displacement according to the method of FIG. 25

An exemplary plot of motor torque as a function of displacement of the jaw member 2402 is illustrated in FIG. 26. As shown, for a given tissue, when the motor torque is less than $\tau_{min}$, the jaw member displacement is relatively low (e.g., less than $\delta_1$). As a result, a degree of jaw closure can be below the threshold closure and the threshold torque $\tau_{min}$ and the jaw member can be under displacement control. In this regime, the motor torque can generally rise with increasing jaw member displacement, representing movement of the jaw member 2402 towards the closed position and rising clamping force. As discussed in greater detail below, RF energy delivery to the tissue is inhibited as the clamping force is lower than desired.

However, when the motor torque rises to $\tau_{min}$, control of the displacement of the jaw member 2402 can be performed by the control system 39 under to load control. In this regime, the control system 39 can ignore any displacement set points received from the user 12, 12' and instead closure of the jaw member 2402 can be controlled based upon torque set points (e.g., a torque between the minimum and maximum torques $\tau_{min}$ and $\tau_{max}$) to result in application of a clamping force between $F_{min}$ and $F_{max}$ It can also be desirable to limit application of RF energy to tissue under circumstances where the end effector 2400 does not fully compress tissue disposed between the clamp arm 152 and the ultrasonic blade 160. If relatively high RF energy levels are employed on critical tissue, such as vessels, without substantially full compression, death can result. In non-powered surgical instruments, such functionality can be achieved through a closure switch that confirms the surgical instrument is fully closed.

To provide this functionality in electrically-powered surgical instruments without a switch, the control system 39 uses the degree of jaw closure to determine whether or not a user 12, 12' can deliver relatively high RF energy levels to tissue. In one aspect, when jaw closure is under displacement control, the control system 39 can inhibit delivery of RF energy to the tissue. In another aspect, when jaw closure is under load control and the jaw closure is less than fully closed, the control system can permit delivery of RF energy at less than a predetermined threshold of RF energy. If a user 12, 12' requests delivery of RF energy greater than the predetermined threshold RF energy, the control system 39 can cause a notification (e.g., audio and/or visual) to be provided by the controller 30. In a further aspect, when jaw closure is under load control and the jaw closure is fully closed, the control system can permit delivery of RF energy greater than the predetermined threshold RF energy.

b. Treatment Protocols for Variation of Clamping Force Based Upon Energy Delivered to Tissue In further embodiments, the control system 39 can be configured to vary compressive forces applied to tissue clamped by an end effector based upon the energy being delivered to the tissue (e.g., ultrasonic vibrations, RF energy, and combinations thereof). This flexibility can allow combination powered surgical instruments to perform "feathering" techniques employed to transect large tissues while ensuring that such tissues are cauterized and any blood vessels are properly coagulated and sealed before transection.

In an embodiment, the control system 39 is configured to determine a thickness of tissue to be transected. As discussed in detail below, a determination of the tissue's relative thickness (e.g., relatively thin or relatively thick tissue) can be used to select whether compressive forces are subsequently applied to the tissue under displacement (e.g., velocity) control or under load control during a feathering treatment.

Figure 27:
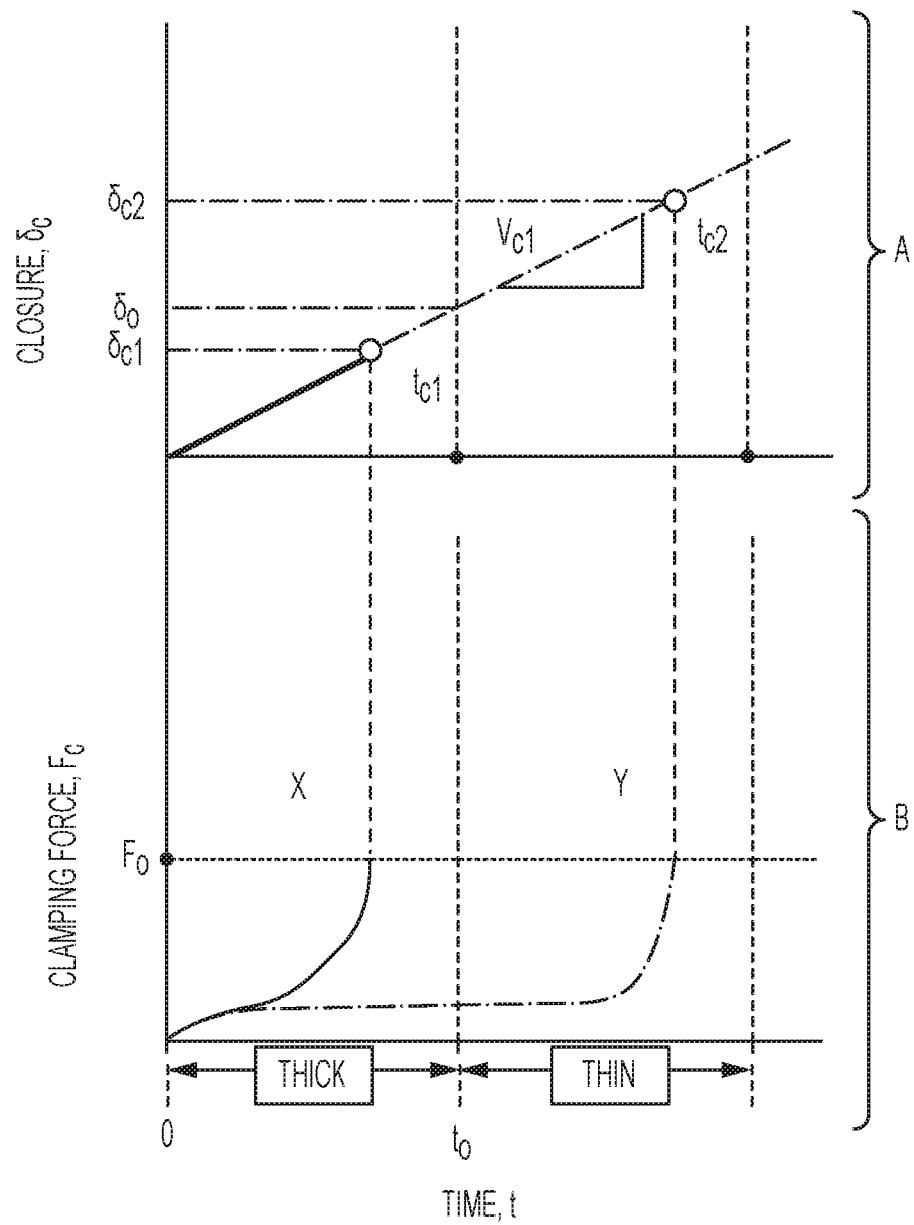
FIG. 27 is a plot of another exemplary embodiment of control of the end effector of FIGS. 24A-24C by the control system of FIG. 19 illustrating displacement of the clamping element (Part A) and clamping force applied to a tissue (Part B) as a function of time.

FIG. 27 is a plot of closing displacement $\delta_c$ of the jaw member 2402 (Part A) and corresponding clamping force $F_c$ (Part B) as a function of time applied to tissue disposed between the jaw member 2402 and the ultrasonic blade 160. With the tissue positioned in this manner, the jaw member 2402 can move towards the closed position under position control at a first clamping velocity $v_{c1}$ greater than a minimum clamping velocity $v_{min}$. As an example, the first clamping velocity $v_{c1}$ can be about 0.03 in./sec. and the minimum clamping velocity $v_{min}$ can be selected from the range from about 0.005 in./sec. to about 0.01 in./sec. In certain embodiments, the first clamping velocity $v_{c1}$ can be constant, as illustrated by the constant slope of the displacement-time trace shown in Part A (top) of FIG. 27.

As the jaw member 2402 contacts the tissue, the compressive force $F_c$ applied to the tissue increases. When the compressive force $F_c$ exceeds a clamping force threshold $F_o$, a closure time $t_c$ is recorded. Assuming that the clamping velocity vii is constant, the corresponding closure displacement $\delta_c$ can also be determined. By comparing the closure time $t_c$ to a threshold time $t_o$ or the closure displacement $\delta_c$ to a threshold displacement $\delta_o$ a relative measure of tissue thickness can be made. As an example, if the closure time $t_c$ is less than the threshold time $t_o$ or the closure displacement $\delta_c$ is less than the threshold displacement $\delta_o$ (Curve X), the tissue is determined to be thick because the jaw member 2402 moves by a relatively small amount to contact the tissue. In contrast, if the closure time $t_c$ is greater than the threshold time $t_o$ or the closure displacement $\delta_c$ is greater than the threshold displacement $\delta_o$ (Curve Y), the tissue is determined to be thin because the jaw member 2402 moves by a relatively large amount to contact the tissue. In certain embodiments, the threshold displacement $\delta_o$ can be about 0.065 in., the thickness $\delta_{c1}$ can be about 0.06 in., and the thickness $\delta_{c2}$ can be about 0.08 in.

Figure 28:
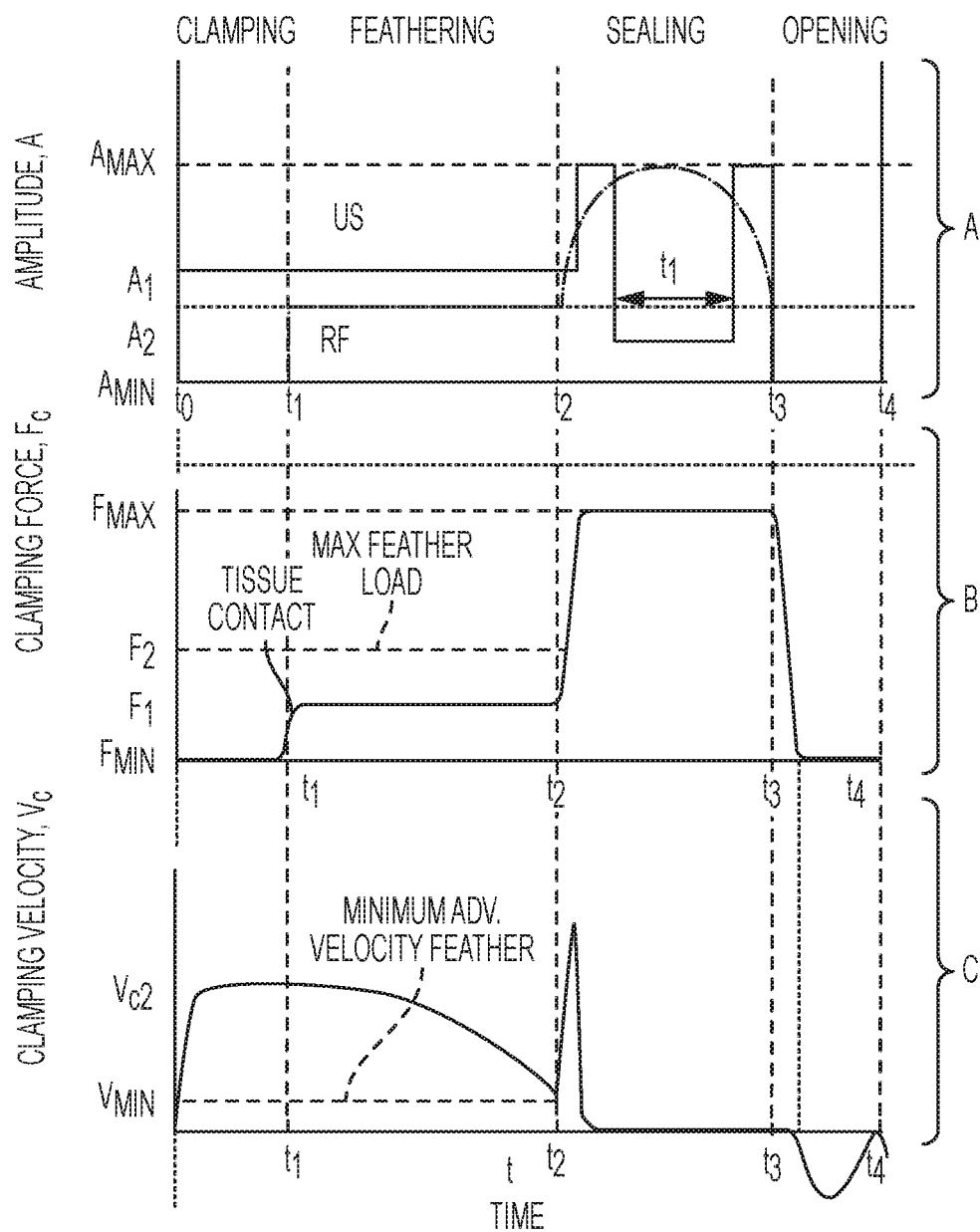
FIG. 28 is a plot of an exemplary embodiment of clamping, feathering, cutting, and opening operations performed by the end effector of FIGS. 24A-24C under control of the control system of FIG. 19; Amplitudes of ultrasonic and radiofrequency energy delivered to the end effector as a function of time (Part A); Clamping forces applied to a tissue by the jaw member under load control as a function of time (Part B), Velocity of the jaw member under load control as a function of time (Part C)

FIG. 28 is a plot illustrating exemplary embodiments of the clamping velocity $v_c$ of the jaw member 2402, the clamping force $F_c$ applied to tissue, and relative amplitudes of various energy delivered to the end effector 2400 (e.g., ultrasonic vibrations and RF energy) as a function of time for a thick tissue. As shown, the tissue can be subjected to a series of tissue treatments including clamping, feathering, and sealing. As discussed in detail below, the clamping treatment is configured to grasp the tissue with the end effector 2400, the feathering treatment is configured to coagulate the tissue, and the sealing treatment is configured to further coagulate the tissue and cut the tissue.

In the embodiment of FIG. 28, the tissue is assumed to be thick and the clamping and feathering treatments are performed under load control. When clamping under load control, the clamping force $F_c$ can begin at approximately zero and it can rise rapidly to a first treatment force $F_1$ once the jaw member 2402 contacts the tissue. The first treatment force $F_1$ can be selected between a minimum clamping force $F_{min}$ and a second treatment force $F_2$. In certain embodiments, the second treatment force can be a local maximum for the clamping force $F_c$ during the clamping and feathering treatments. As an example, the first treatment force $F_1$ can be selected from the range between about 0.25 lbs. to about 0.5 lbs. (e.g., about 0.5 lbs.), and the second treatment force $F_2$ can be selected from the range from about 1 lb. to about 1.5 lbs., the maximum clamping force $F_{min}$, can be about 2.5 lbs.

Delivery of energy to the end effector 2400 during the clamping treatment is also illustrated in FIG. 28. In certain embodiments, delivery of RF energy to the electrode 2412 is omitted during the clamping treatment, while ultrasonic vibrations is transmitted to the ultrasonic blade 2410. As shown, the ultrasonic vibrations can have a first amplitude $A_1$ selected between a minimum ultrasonic amplitude $A_{min}$ and a maximum ultrasonic amplitude $A_{max}$. As an example, $A_{min}$ can be about 25% of $A_{max}$, $A_1$ can be selected from the range from about 60% of $A_{max}$ to about 80% of $A_{max}$.

During the clamping treatment, the clamping velocity $v_c$ can increase from zero to a second clamping velocity $v_{c2}$. As an example, the second clamping velocity $v_{c2}$ can be a local maximum on the clamping velocity during the clamping and feathering treatments and it can be about 0.025 in./sec. In certain embodiments, the second clamping velocity $v_{c2}$ can be the same as the first clamping velocity $v_{c1}$. The jaw member 2402 can move at second clamping velocity $v_{c2}$ throughout the duration of the clamping treatment (e.g., until the clamping force $F_c$ rises to the first treatment force $F_1$ and the feathering treatment begins.

A first exemplary embodiment of the feathering treatment is also illustrated in FIG. 28. In general, the feathering treatment can be configured to coagulate tissue disposed between the jaw member 2402 and the ultrasonic blade 160. As shown in FIG. 28, when the feathering treatment is performed under load control, the clamping force $F_c$ is maintained at about a first treatment force $F_1$. In certain embodiments, the first treatment force $F_1$ is approximately constant through the duration of the feathering treatment. Similarly, the amplitude of ultrasonic vibrations is maintained at about $A_1$ and the RF energy delivered to the ultrasonic blade 160 is maintained at an approximately constant level.

It can also be observed that the clamping velocity $v_c$ can generally decrease with time during the feathering treatment. This reduction in $v_c$ can result from changes in the mechanical properties of the tissue due to coagulation of the tissue by friction (e.g., mechanical vibrations of the ultrasonic blade 2410) and RF energy delivered to the tissue from the electrode 2412. That is, the mechanical properties of the tissue can change over time during the feathering treatment. Accordingly, as time elapses under load control, a clamping velocity $v_c$ can be sufficient to maintain the first treatment force $F_1$. Provided that $v_c$ is greater than a minimum clamping velocity $v_{min}$, the control system 39 can maintain the first treatment force $F_1$ for the duration of the feathering treatment. If the clamping velocity $v_c$ falls to the minimum clamping velocity $v_{min}$, the control system 39 can perform feathering under load control according to a second exemplary embodiment, discussed in greater detail below.

The sealing treatment can follow immediately after the feathering treatment and it can be controlled by the control system 39 under load control. In general, the sealing operation can be configured to both coagulate and cut the tissue clamped by the end effector 2400. The sealing operation begins in response to detection that a trigger condition is satisfied. In one embodiment, the trigger condition can be movement of the jaw member 2402 to a predetermined degree of closure (e.g., the jaw member 2402 moves to a predetermined distance from the ultrasonic blade 2410). The degree of closure of the jaw member 2402 can be monitored by the control system 39 as discussed above. In another embodiment, the trigger condition can be a deviation from a velocity set point by a threshold amount or a clamping force $F_c$ that rises to a predetermined percentage of a maximum clamping force $F_{max}$, as discussed in greater detail below in the context of a third exemplary embodiment of the feathering treatment under displacement (velocity) control.

In the sealing operation, the jaw member 2402 is moved to the closed position and the clamping force increases from $F_1$ to the maximum clamping force $F_{max}$. The clamping velocity $v_c$ can rise sharply to a level greater than the first clamping velocity $v_{c1}$ while the clamping force rises to $F_{max}$ and subsequently decreases to about zero. That is, the jaw member 2402 does not move in closure once the closed position is reached and the maximum clamping force $F_{max}$ is applied to the tissue. As discussed above, full closure of the jaw member 2402 can ensure that the middle layer 2004 of blood vessels are separated. The maximum clamping force $F_{max}$ can be a global maximum force over all tissue treatment operations and it can be selected from the range from about 2.5 lbs. to about 3.6 lbs.

Concurrently, the amplitude of ultrasonic vibrations transmitted to the ultrasonic blade 2410 and the RF energy transmitted to the electrodes 2412 can be varied to facilitate coagulation and cutting of tissue. As shown in FIG. 28, Part A, the amplitude of ultrasonic vibrations briefly increases to the maximum amplitude $A_{max}$ to provide frictional heating for coagulating the tissue. Subsequently, the amplitude of ultrasonic vibrations decreases to a second amplitude $A_2$ greater than the minimum amplitude but less than the first amplitude $A_1$. As an example, $A_2$ can be about 50% of $A_{max}$. This decrease in ultrasonic vibration amplitude can be synchronized with an increase in the amplitude of RF energy to a maximum value. This increase in RF energy can be configured to further promote coagulation of the tissue. Subsequently, the ultrasonic vibration amplitude can increase to the maximum amplitude $A_{max}$ a second time to promote tissue cutting while the amplitude of RF energy decreases to zero.

Following the sealing operation, the jaw member 2402 can open to release the tissue. As shown in FIG. 28, Part B, the clamping force $F_c$ decreases from the maximum clamping force $F_{max}$ to about zero. Concurrently, as shown in FIG. 28, Part C, the velocity of the jaw member 2402 adopts a negative value, representing opening of the jaw.

Figure 29:
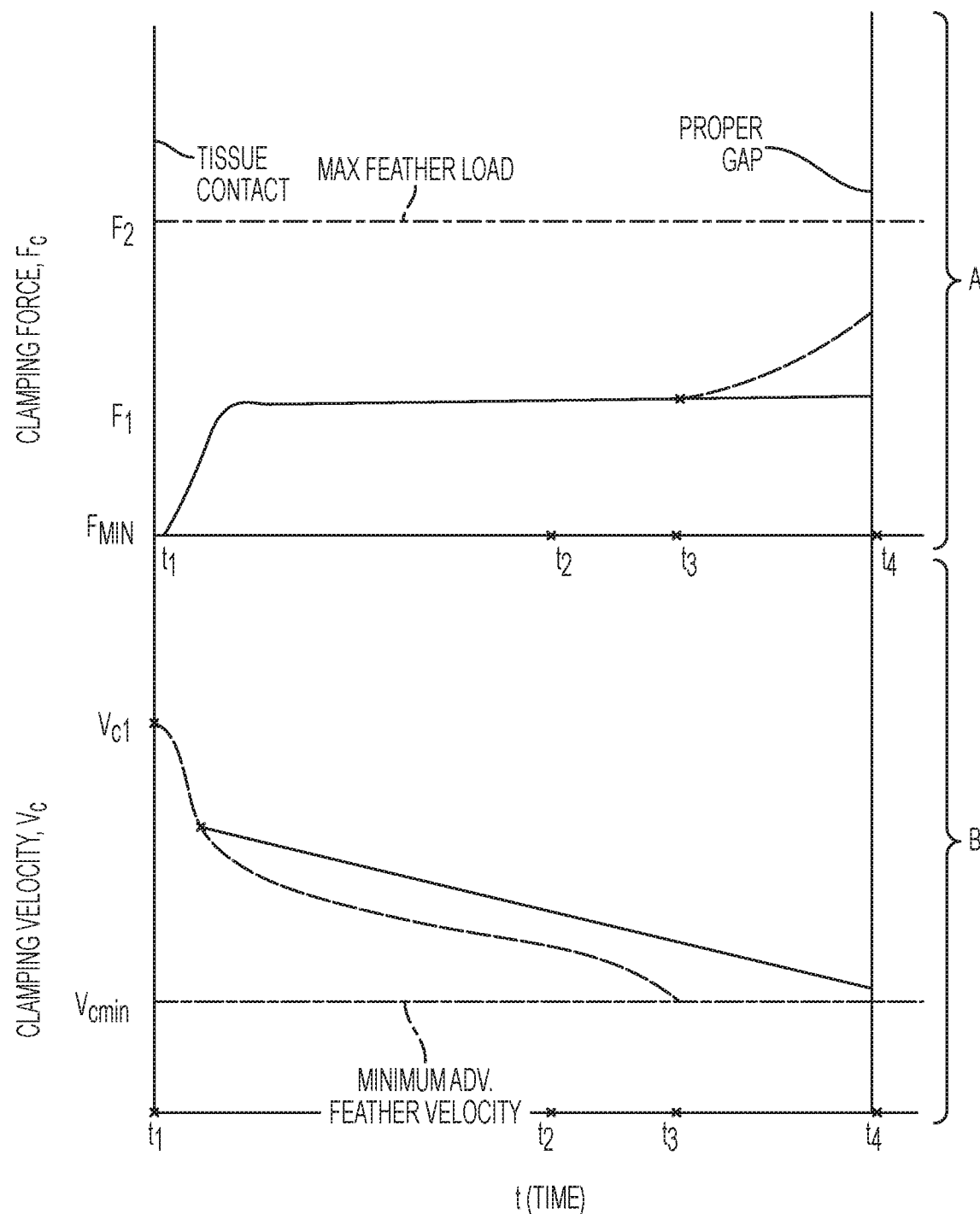
FIG. 29 is a plot of an alternative embodiment of control of the end effector of FIGS. 24A-24C by the control system of FIG. 19; Clamping forces applied to a tissue by the jaw member under load control as a function of time (Part A), Velocity of the jaw member under load control as a function of time (Part B)

A second exemplary embodiment of the feathering treatment under load control is illustrated in FIG. 29. In the first embodiment discussed above (solid lines), the clamping velocity $v_c$ remains above the minimum clamping velocity $v_{min}$. In this second embodiment of the feathering treatment, the clamping velocity $v_c$ falls to a level approximately equal to $v_{min}$. Under this circumstance, instead of maintaining the clamping force $F_c$ at the first treatment force $F_1$ throughout the feathering treatment, when the clamping velocity $v_c$ falls to $v_{min}$, the clamping force is increased to maintain the clamping velocity $v_c$ at least equal to $v_{min}$, as shown in the dashed lines of FIG. 29, Parts A and B. Upon determining that the triggering condition is satisfied, the second embodiment of the feathering treatment ends and the sealing treatment begins, as discussed above.

Figure 30:
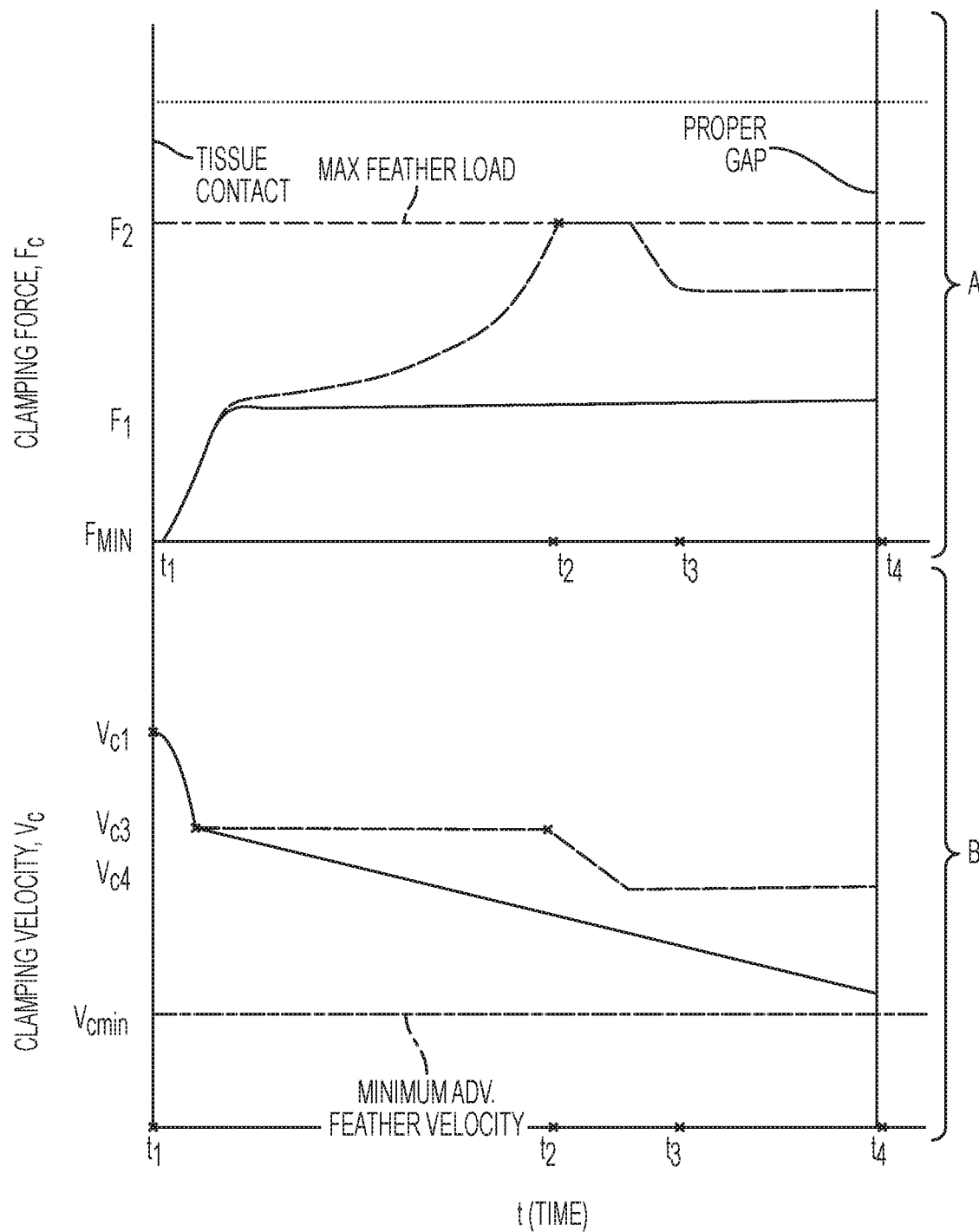
FIG. 30 is a plot of an alternative embodiment of control of the end effector of FIGS. 24A-24C by the control system of FIG. 19; Clamping forces applied to a tissue by the jaw member under position control as a function of time (Part A), Velocity of the jaw member under position control as a function of time (Part B).

A third exemplary embodiment of the feathering treatment under position control is illustrated in FIG. 30. As discussed above, position control can be employed when the tissue is determined to be thin. In the first embodiment under load (solid lines), the clamping velocity $v_c$ is allowed to fall while the first treatment force $F_1$ is maintained. In contrast, this third embodiment of the feathering treatment initially maintains the clamping velocity $v_c$ at a third clamping velocity $v_{c3}$ while the clamping force $F_c$ is allowed to change from the first treatment force $F_1$. The third clamping velocity $v_{c3}$ can be approximately constant. In certain embodiments, the third clamping velocity $v_{c3}$ can be the same as the first clamping velocity $v_{c1}$.

The clamping velocity $v_c$ can be kept constant or changed depending upon the clamping force $F_c$ resulting from $v_{c3}$ during the feathering treatment. If the clamping force $F_c$ remains less than the second clamping force $F_2$, the control system 39 maintains the third clamping force $v_{c3}$ throughout the feathering treatment. However, if the clamping force $F_c$ rises to the level of the second clamping force $F_2$ (e.g., at time $t_2$), the clamping velocity is reduced from the third clamping velocity $v_{c3}$ to a fourth clamping velocity $v_{c4}$ that is greater than the minimum clamping velocity $v_{min}$. The fourth clamping velocity $v_{c4}$ can be reached at time $t_3$ be sufficient to maintain the clamping force $F_c$ at a level less than the second treatment force $F_2$ (e.g., between the first treatment force $F_1$ and the second treatment force $F_2$) until the end of the feathering treatment at time $t_4$. Upon determining that the triggering condition is satisfied, the second embodiment of the feathering treatment can end and the sealing treatment can begin. In an embodiment, the time duration between time $t_2$ and time $t_3$ can be from the range from about 0.5 sec. to about 1.5 sec. In another embodiment, the time duration between time $t_3$ and time $t_4$ can be from the range from about 1 sec. to about 4 sec.

As discussed above, the trigger condition can be a deviation from a velocity set point by a threshold amount. This trigger condition can be satisfied by deviation of the clamping velocity $v_c$ from either the third clamping velocity $v_{c3}$ or the fourth clamping velocity $v_{c4}$ by a predetermined threshold clamping velocity $\Delta v_c$.

In another embodiment, the trigger condition can be the clamping force $F_c$ rising to a predetermined percentage of the maximum clamping force $F_{max}$.

III. Miscellaneous

It should be understood that any of the versions of instruments described herein can include various other features in addition to or in lieu of those described above. By way of example only, any of the instruments described herein can also include one or more of the various features disclosed in any of the various references that are incorporated by reference herein.

While the examples herein are described mainly in the context of electrosurgical instruments, it should be understood that various teachings herein can be readily applied to a variety of other types of devices. By way of example only, the various teachings herein can be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to an electrosurgical instrument, it should be understood that the teachings herein can be readily applied to an ENSEAL® Tissue Sealing Device by Ethicon Endo-Surgery, Inc., of Cincinnati, Ohio. In addition or in the alternative, it should be understood that the teachings herein can be readily combined with the teachings of one or more of the following: U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007 the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013, the disclosure of which is incorporated by reference herein; and/or U.S. Pub. No. 2013/0023868, entitled "Surgical Instrument with Contained Dual Helix Actuator Assembly," published Jan. 31, 2013, the disclosure of which is incorporated by reference herein. Other suitable ways in which the teachings herein can be applied to an electrosurgical instrument will be apparent to those of ordinary skill in the art in view of the teachings herein.

In versions where the teachings herein are applied to a surgical stapling instrument, it should be understood that the teachings herein can be combined with the teachings of one or more of the following, the disclosures of all of which are incorporated by reference herein: U.S. Pat. Nos. 7,380,696; 7,404,508; 7,455,208; 7,506,790; 7,549,564; 7,559,450; 7,654,431; 7,780,054; 7,784,662; and/or 7,798,386. Other suitable ways in which the teachings herein can be applied to a surgical stapling instrument will be apparent to those of ordinary skill in the art in view of the teachings herein.

It should also be understood that the teachings herein can be readily applied to any of the instruments described in any of the other references cited herein, such that the teachings herein can be readily combined with the teachings of any of the references cited herein in numerous ways. Other types of instruments into which the teachings herein can be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above can be designed to be disposed of after a single use, or they can be designed to be used multiple times. Versions can, in either or both cases, be reconditioned for reuse after at least one use. Reconditioning can include any combination of the steps of disassembly of the device, followed by cleaning or replacement of particular pieces, and subsequent reassembly. In particular, some versions of the device can be disassembled, and any number of the particular pieces or parts of the device can be selectively replaced or removed in any combination. Upon cleaning and/or replacement of particular parts, some versions of the device can be reassembled for subsequent use either at a reconditioning facility, or by a user immediately prior to a procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, versions described herein can be sterilized before and/or after a procedure. In one sterilization technique, the device is placed in a closed and sealed container, such as a plastic or TYVEK bag. The container and device can then be placed in a field of radiation that can penetrate the container, such as gamma radiation, x-rays, or high-energy electrons. The radiation can kill bacteria on the device and in the container. The sterilized device can then be stored in the sterile container for later use. A device can also be sterilized using any other technique known in the art, including but not limited to beta or gamma radiation, ethylene oxide, or steam.

Having shown and described various embodiments of the present invention, further adaptations of the methods and systems described herein can be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical system, comprising:
    a surgical tool including a shaft and an end effector formed at a distal end thereof, the end effector having a clamping element and an ultrasonic blade, the clamping element being movable relative to the ultrasonic blade to clamp and treat tissue disposed between the clamping element and the ultrasonic blade;
    a closure mechanism configured to selectively move the clamping element towards the ultrasonic blade from an open configuration to a closed configuration at a predetermined clamping velocity ($v_c$); and
    a control system configured to:
        maintain $v_c$ at a first clamping velocity ($v_{c1}$) greater than a minimum clamping velocity ($v_{min}$) until a predetermined clamping force threshold ($F_o$) is achieved;
        determine a closure parameter including at least one of an amount of time required to reach $F_o$ and an amount of displacement of the clamping element required to achieve $F_o$;
        determine a tissue characteristic based upon the closure parameter; and
        deliver energy to the ultrasonic blade to treat tissue in a feathering treatment according to a feathering treatment protocol based upon the determined tissue characteristic.

2. The system of claim 1, wherein $F_o$ is a force resulting from contact of the clamping element with a tissue disposed between the clamping element and the ultrasonic blade.

3. The system of claim 1, wherein the feathering treatment is effective to coagulate a tissue disposed between the clamp arm and the ultrasonic blade.

4. The system of claim 1, wherein the tissue characteristic is a thickness of a tissue disposed between the clamping element and the ultrasonic blade.

5. The system of claim 4, wherein the tissue thickness is less than a predetermined thickness and the control system is configured to operate in the feathering treatment protocol by:
    maintaining $v_c$ at a third clamping velocity ($v_{c3}$) while a clamping force applied to tissue disposed between the clamp arm and the ultrasonic blade is less than a predetermined second treatment force ($F_2$); and
    decreasing $v_c$ from $v_{c3}$ to a fourth clamping velocity ($v_{c4}$) for the remainder of the feathering treatment in response to the clamping force rising to $F_2$, wherein $v_{c4}$ is configured to maintain the clamping force below $F_2$.

6. The system of claim 5, wherein $v_{c3}$ and $v_{c4}$ are each approximately constant.

7. The system of claim 4, wherein the tissue thickness is greater than a predetermined thickness and the control system is configured to operate in the feathering treatment protocol by applying a clamping force to tissue disposed between the clamp arm and the ultrasonic blade at an approximately constant first treatment force ($F_1$).

8. The system of claim 7, wherein the control system is configured to:
    allow $v_c$ to decrease to a level approximately equal to $v_{min}$; and
    increase the clamping force to a level between $F_1$ and a less than a second treatment force ($F_2$) for the remainder of the feathering treatment.

9. The system of claim 7, wherein $F_1$ is based upon the determined tissue characteristic.

10. The system of claim 1, further comprising an electrode configured to deliver radiofrequency energy to a tissue disposed between the clamping element and the ultrasonic blade.

11. The system of claim 10, wherein the control system is configured to deliver at least one of ultrasonic energy to the ultrasonic blade and radiofrequency energy to the electrode according to a sealing treatment protocol occurring after the feathering treatment for coagulating and cutting a tissue disposed a tissue disposed between the clamping element and the ultrasonic blade.

12. The system of claim 11, wherein the control system is further configured to perform the sealing treatment in response to detection that a preselected trigger condition is satisfied.

13. The system of claim 12, wherein trigger condition is movement of the clamping element to a predetermined distance from the ultrasonic blade.

14. The system of claim 12, wherein the trigger condition is deviation of $v_c$ from a velocity set point by a predetermined velocity threshold.

15. The system of claim 12, wherein the trigger condition is application of a clamping force at a predefined amount of a maximum clamping force $F_{max}$.

16. A method for treating tissue, comprising:
actuating a motor of a surgical tool including a shaft and an end effector, the end effector formed at a distal end of the shaft and having a clamping element and an ultrasonic blade coupled to an ultrasonic transducer, the clamping element being moveable relative to the ultrasonic blade to a tissue clamping position between an open position and a closed position of the clamping element at a predetermined clamping velocity ($v_c$);
maintaining $v_c$ at a first clamping velocity ($v_{c1}$) greater than a minimum clamping velocity ($v_{min}$) until a predetermined clamping force threshold ($F_o$) is achieved;
determining a closure parameter including at least one of an amount of time ($t_c$) required to reach $F_o$ and an amount of displacement of the clamping element $\delta_c$ required to achieve $F_0$;
determining a tissue characteristic based upon the closure parameter; and
delivering energy to the ultrasonic blade to treat tissue in a feathering treatment according to a feathering treatment protocol based upon the determined tissue characteristic.

17. The method of claim 16, wherein $F_o$ is a force resulting from contact of the clamping element with a tissue disposed between the clamping element and the ultrasonic blade.

18. The method of claim 16, wherein the feathering treatment is effective to cauterize a tissue disposed between the clamp arm and the ultrasonic blade.

19. The method of claim 16, wherein the tissue characteristic is a thickness of a tissue disposed between the clamping element and the ultrasonic blade.

20. The method of claim 19, further comprising:
determining the tissue thickness to be less than a predetermined thickness;
maintaining $v_c$ at a third clamping velocity ($v_{c3}$) while a clamping force applied to tissue disposed between the clamp arm and the ultrasonic blade is less than a predetermined second treatment force ($F_2$); and
decreasing $v_c$ from $v_{c3}$ to a fourth clamping velocity ($v_{c4}$) for the remainder of the feathering treatment in response to the clamping force rising to $F_2$, wherein $v_{c4}$ is configured to maintain the clamping force below $F_2$.

* * * * *